(12) United States Patent
Kuehne et al.

(10) Patent No.: US 8,242,105 B2
(45) Date of Patent: Aug. 14, 2012

(54) STRUCTURAL MIMETICS OF PROLINE-RICH PEPTIDES AND THE PHARMACEUTICAL USE THEREOF

(75) Inventors: Ronald Kuehne, Berlin (DE); Hartmut Oschkinat, Berlin (DE); Christoph Brockmann, Berlin (DE); Hans-Guenther Schmalz, Bruehl (DE); Jan Zaminer, Wuerzburg (DE)

(73) Assignee: Forschungsverbund Berlin E.V., Berlin (DE)

( * ) Notice: Subject to any disclaimer, the term of this patent is extended or adjusted under 35 U.S.C. 154(b) by 302 days.

(21) Appl. No.: 12/442,681

(22) PCT Filed: Sep. 25, 2007

(86) PCT No.: PCT/DE2007/001768
§ 371 (c)(1),
(2), (4) Date: Oct. 6, 2009

(87) PCT Pub. No.: WO2008/040332
PCT Pub. Date: Apr. 10, 2008

(65) Prior Publication Data
US 2011/0034438 A1  Feb. 10, 2011

(30) Foreign Application Priority Data

Sep. 25, 2006 (EP) .................................. 06090178
Sep. 25, 2006 (EP) .................................. 06090179
Nov. 29, 2006 (DE) ........................ 10 2006 057 070
May 7, 2007 (EP) .................................. 07090095

(51) Int. Cl.
*A61K 31/55* (2006.01)
*C07D 223/00* (2006.01)
(52) U.S. Cl. .................................. 514/212.06; 540/484
(58) Field of Classification Search ............. 514/212.06; 540/484
See application file for complete search history.

(56) References Cited

U.S. PATENT DOCUMENTS
6,372,735 B1 * 4/2002 Ohtsuka et al. .......... 514/212.06

FOREIGN PATENT DOCUMENTS
EP  1 077 218  2/2001
WO  2006/092722  9/2006

OTHER PUBLICATIONS
Manzoni et al. CAS: 143: 60209, 2005.*
* cited by examiner

*Primary Examiner* — Rei-tsang Shiao
(74) *Attorney, Agent, or Firm* — Joyce von Natzmer; Agris & von Natzmer LLP

(57) ABSTRACT

The invention relates to compounds of general formula (I), which can be used particularly as structural mimetics of proline-rich peptides and are therefore capable of binding PRM binding domains (proline-rich motif binding domains) of proteins. The invention also relates to the use of said compounds as pharmaceutical active agents and the use of these pharmaceutical active agents for treating bacterial diseases, neurodegenerative diseases and tumors.

26 Claims, 5 Drawing Sheets

STRUCTURAL MIMETICS OF PROLINE-RICH PEPTIDES AND THE PHARMACEUTICAL USE THEREOF

This is the U.S. national stage of International application PCT/DE2007/001768, filed Sep. 25, 2007 designating the United States and claiming priority to European Applications EP 0609078.2, filed Sep. 25, 2006; EP 06090179.0, filed Sep. 25, 2006; and EP 07090095.6, filed May 7, 2007 and German application DE 10 2006 057 070.7, filed Nov. 29, 2006.

The invention relates to compounds which can be used particularly as structural mimetics of proline-rich peptides and are therefore capable of binding PRM binding domains (proline-rich motif binding domains) of proteins. The invention also relates to the use of said compounds as pharmaceutical active agents and the use of these pharmaceutical active agents for treating bacterial diseases, neurodegenerative diseases and tumors.

Peptides and proteins are essential constituents of organisms and have a wide variety of functions. While proteins especially assume biocatalytic functions (enzymes) and also serve as important tissue components, peptides assume important functions in the organism, especially in the form of hormones, neurotransmitters and neuromodulators. As a result of binding to membranous receptors and cell-physiological secondary reactions mediated thereby, peptides influence cell-cell communication and regulate a variety of vital processes such as metabolism, immune defense, digestion, respiration, sensation of pain, reproduction, behavior, electrolyte metabolism and others.

Regarding the prior art, there is therefore a need to clarify the precise interrelations in an organism and also provide a necessary basis for the treatability of pathogenic conditions. With increasing understanding of biological processes on a molecular level, the interconnection between biology and chemistry has also increased, supported by the great progress in analytical methods and computer-aided theoretical methods. These are important preconditions for successful identification of lead structures in drug design. Nevertheless, the actual objective, i.e. simple and efficient de novo design of active substances, is still far away. On the contrary, huge efforts in empirical research are normally required in order to synthesize libraries of possible target substances from natural structures and optimize them for a particular effect. In addition to the large amount of time and enormous cost, it has frequently been found that active substances developed with the aid of computers achieve the desired effect in real, highly complex biological systems (e.g. humans) only to an insufficient extent or have intolerable side effects.

Peptidomimetic components and the preparation of biologically active derivatives comprising the RGD sequence have been described in the prior art. These cyclic peptidomimetic components have an azabicycloalkane structure and can be used in the treatment of angiogenetic phenomena. They have particularly good properties as antagonists of certain integrins (WO 2006/092722, WO 2005/042531, EP 1 077 218).

SUMMARY OF THE INVENTION

In view of this background, the development of active substances, especially peptidic or peptidomimetic ones, is still a great challenge, which also applies to synthetic aspects, because, in the wide-ranging interdisciplinary interplay, it is not least the organic chemistry with its capabilities and limitations that determines the access to the desired target molecules. These molecules must be synthesized with the least possible number of steps and, as a rule, in a stereoselective manner, so that advanced and improved synthetic methods are steadily required in order to achieve this objective not only in a laboratory but also with respect to future uses on an industrial scale.

The object of the invention was therefore to provide compounds that could be used as mimetics for proline-rich peptides, especially if the latter have a PPII-helical conformation. The proline-proline dipeptide units, especially those with a PPII-helical conformation, can preferably act as ligands for so-called PRM-binding domains (PRM=proline-rich motifs).

Surprisingly, the problem according to the invention is solved by providing a compound in accordance with the general formula

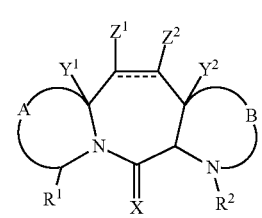

1 with a saturated or unsaturated central seven-membered ring, wherein
X is O and/or S;
A, B are ring bridges;
$Y^1$, $Y^2$ are H, alkyl, fluoroalkyl, aryl and/or heteroaryl;
$Z^1$, $Z^2$ are H; carbonyl; OH; O-alkyl; O-acyl; $NR^1R^2$ (wherein $R^1$ and/or $R^2$=H, alkyl, acyl, sulfonyl); alkyl; acyl; fluoroalkyl; aryl and/or heteroaryl;
$R^1$ is alkyl, acyl, alkoxycarbonyl, aryloxycarbonyl and/or aminocarbonyl ($CONH_2$, CONHR, CONH-peptidyl, (with R));
$R^2$ is H, alkyl, aryl, alkylcarbonyl, arylcarbonyl, alkoxycarbonyl, aminocarbonyl, aryloxycarbonyl, alkylsulfonyl, arylsulfonyl, aminoacyl and/or peptidyl.

It was completely surprising to find the compounds according to the invention free of the disadvantages of the prior art. Apart from the above-mentioned disadvantages of the prior art, the use of peptidic active substances as medical drugs up to now has been restricted by a number of additional factors:
1) low metabolic stability as a result of proteolysis in the gastrointestinal tract and in serum;
2) poor absorption upon oral ingestion, especially as a result of the high molecular mass;
3) rapid elimination via liver and kidneys; and
4) lack of selectivity as a result of interaction with various receptors.

Surprisingly, the compounds according to the invention can be used as mimetics which, being artificially produced substances, are capable of assuming especially the function of a receptor ligand, mimicking (agonist) or blocking (antagonist) the biological effect of a peptide. Mimetics in the meaning of the invention are chemical compounds that are functionally analog to prolines or proline-rich peptides and therefore interact with the corresponding domains, as would be the case with prolines or proline-rich peptides, and preferably trigger the same effects as prolines or proline-rich peptides.

The terms "functional analogs" or "mimetics" are not relative terms because these expressions have a generally recognized meaning in the art of biology. According to the invention, the terms "functional analogs" or "mimetics" can preferably be understood as equivalents. That is, mimetics—compared to the natural structure—are variants providing essentially the same function in essentially the same way with essentially the same result.

While the principle of providing peptide mimetics is well-known, only a few examples of PPII structure mimetics have been disclosed so far, which, however, exhibit quite a number of drawbacks. Although there have been various approaches of completely or partially replacing the structural motif of the PPII helix with synthetic analogs, it has not been possible—or only to a very limited extent—to investigate the interaction of well-known structures with different protein domains. Also, the prior art teaches a person of average skill in the art that the interaction of proline-rich helices with different protein domains does not have any particular biological importance. It is the merit of the inventors to have shown that such interaction, or modification thereof, is accompanied by numerous diseases such as bacterial or viral infections, neurodegenerative diseases or formation of tumors. A large number of mimetics known in the prior art can only be provided by means of catalysts whose removal from the system frequently is difficult or cannot be achieved at all. Furthermore, it should be noted that well-known products do not have a long shelf-life and are frequently contaminated with products required in synthesis, so that medical uses in particular are impeded or made impossible. In addition, the binding affinity of the mimetics known to date is insufficient.

The interaction of peptide ligands with protein receptors plays an important role in the regulation of biological processes and crucially depends on the peptide geometry. Under physiological conditions, the conformation of a linear peptide is in a dynamic equilibrium as a result of rotation about single bonds, which equilibrium depends on the pH value and temperature. As a consequence, only a low percentage of the biological reactive conformation is present.

The conformation of a peptide backbone is usually described by the three angles $\phi$ (phi), $\psi$ (psi) and $\omega$ (omega). Owing to its partial double bond character, a peptide bond is hindered in its rotation and has a planar geometry, resulting in two preferred conformations: the trans and cis peptide bonds with $\omega=180°$ and $\omega=0°$, respectively, among which the trans conformation is energetically more favorable and therefore prevails.

In a first approximation, the torsion angles $\phi$ and $\psi$ of the amino acid residues are therefore sufficient to describe the conformation of the peptide backbone. The angle $\phi$ describing the rotation about the $N-C_\alpha$ bond is defined by the four atoms $C(=O)-N-C_\alpha-C(=O)$. In the same way, $N-C_\alpha-C(=O)-N$ define the angle $\psi$ describing the rotation about the $C_\alpha-C(=O)$ bond. Although a large number of different combinations of $\phi$ and $\psi$ are possible in theory, specific preferred conformations generally exist in peptides, which depend on size, polarity and charge of the side chains, resulting in formation of the well-known secondary structures such as $\alpha$-helix, $\beta$-pleated sheet, $\beta$-turn, etc.

The Amino Acid Proline as a Component of Peptides

Being the only secondary amino acid, proline assumes a special rank among the twenty naturally occurring amino acids. Cyclization of the $\alpha$-side chain with the amide nitrogen results in a relative restriction of the torsion angle $\phi=(-65°\pm15°)$ as an element of the five-membered ring so that the peptide consequently has less rotational degrees of freedom. On the one hand, double alkylation of the nitrogen gives rise to the fact that the otherwise common amide proton (in the peptide backbone) is missing, consequently ruling out proline as a hydrogen bridge donor, and, on the other hand, the carbonyl group is particularly rich in electrons and therefore a superior hydrogen bridge acceptor compared to other amino acids. As a result of these geometric and electronic properties, proline is not capable of stabilizing an $\alpha$-helix ($\alpha$-helix breaker) and does not form a $\beta$-pleated sheet structure either ($\beta$-pleated sheet breaker), but is rather found in other typical secondary structures, the so-called p-turns and the polyproline helix (PPII helix).

Proline-Rich Motifs and the PPII Helix as a Secondary Structure

Proline-rich amino acid sequences are frequently found in peptides involved in intracellular signal transduction processes. This involves sequences wherein proline is either exclusively or predominantly present (usually four or more proline units in succession).

This induces the characteristic secondary structure, i.e. the polyproline helix or, briefly, PPII helix, which is understood to be an elongated, left-handed helix with torsion angles $\phi=-78°$ and $\psi=+146°$ of the peptide backbone. As a consequence, there is a pseudo-$C_3$-rotational symmetry about the helical axis, with precisely three proline residues per turn in cross-section (see Figures), which is why the proline residues in proline-rich sequences are preferably repeated with a periodicity of at least three (e.g. PxxPxxP or PPxPPxPPx).

In this way, the proline side chains and the carbonyl groups of the peptide backbone are exposed to the solvent at regular intervals. Owing to the absence of intramolecular hydrogen bridges, the carbonyl groups are particularly suited to form intermolecular hydrogen bridges with receptor proteins.

However, the PPII helix structural motif can also be induced in those cases where proline is not exclusively present. In particular, the amino acid Glu frequently occurs in PPII helices and in the proximity thereof, but also Gln, Arg, Ala, Leu, Ser, Asp and His have been found. The preferred binding mode between domain and ligand determines which proline positions must be strictly conserved and which ones may optionally be replaced with other amino acids.

In a preferred embodiment of the invention A and/or B are selected so as to be 5 and/or 6 ring atoms, the ring members represented by A and B being selected from the group comprising C, O, S and/or N atoms. Obviously, it may also be preferred to select the ring bridges A, B in such a way that a 4-, 5- or 6-membered ring is formed, the ring members being constituted of $-CH_2-$, $-O-$, $-S-$ and $-NR-$, with R=H, alkyl, or acyl.

In another preferred embodiment of the invention the compound has the general formula 2:

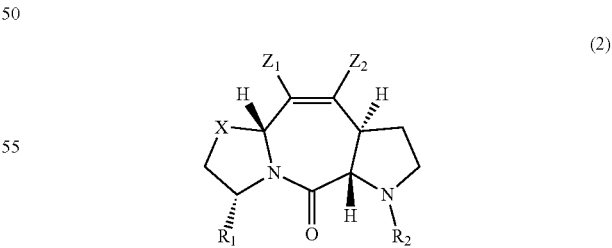

(2)

with $Z^1$, $Z^2$ as represented in structure 1 and with the configuration shown in formula 2;
with $R^1$, $R^2$=alkyl, acyl, hetaryl and/or sulfonyl,
with $X=-CH_2-$, $-O-$, $-S-$ and/or $-NH-$ and $-N(R)-$.

In another preferred embodiment of the invention the compound corresponds to formula 3:

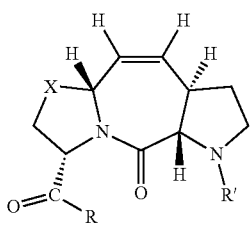

(3)

with X=—CH$_2$—, —O— and/or —S—;
with R=—NHR", —OR", with R"=peptidyl, substituted alkyls and/or hetaryl;
with R'=acyl, peptidyl and/or sulfonyl.

It is particularly preferred that R' in formula 3 be peptidyl.

In a preferred aspect the invention relates to the use of the above-mentioned compounds as pharmaceutical active agents. The use as pharmaceutical active agents relates to the use in surgical, therapeutic or diagnostic methods.

In another aspect the invention relates to a pharmaceutical agent comprising the compounds according to the invention, optionally together with a pharmaceutically tolerable carrier.

Preferred pharmaceutical carriers are e.g. fillers, diluents, binders, humectants, dissolution retarders, disintegrants, absorption enhancers, wetting agents, absorbents and/or lubricants.

In another aspect the invention relates to the use of the compounds according to the invention as ligand for a domain selected from the group comprising Src homology 3 domains, WW domains, Ena/VASP homology 1 domains, GYF domains, UEV domains and/or profilin.

In a preferred fashion, all the above domains interact particularly with proline-rich sequences with affinities between 1 and 500 μM and require additional flanking epitopes in particular embodiments of the invention so as to achieve the necessary specificity. Preferably, binding between ligands, peptide and domain is caused especially via interaction of two preformed hydrophobic surfaces. Advantageously, aromatic amino acids accumulate on the surface of the domain proteins, the residues of which form a hydrophobic binding pocket. Owing to the rigid nature of the PPII helix, the proline-rich peptide ligand has a geometrically fixed, complementary structure that makes contact with the domain surface. Advantageously, hydrophobic contacts are not developed over the entire length of the core motif, but instead the ligand peptide forms a screen-like structure spanning over the domain. Some of the proline residues are received in the hydrophobic binding pocket, thus interacting with the aromatic residues of the domain. Where these contacts are not sufficient to achieve a biologically relevant binding strength, additional stabilizing hydrogen bridges are formed with advantage, which is very well possible by virtue of the electron-rich carbonyl group of proline.

In energetic terms, intermolecular binding is favored owing to the restricted flexibility of the PPII helix because, as a result of the relatively high degree of order, the decrease in entropy during bond formation is smaller compared to a normal linear peptide. To quantify this amount of energy, one might consider a dipeptide xP which has only two of the otherwise usual four degrees of freedom of rotation about the peptide backbone. Each rotational degree of freedom at 300 K corresponds to about 3.5 kJ/mol, so that an energetic advantage of about 7 kJ/mol per xP dipeptide results upon complex formation.

A further increase in affinity is observed as a result of the multiple repeats of proline-rich sequences in a single peptide, e.g. in the bacterial surface protein ActA which binds to the EVH1 domain (Ena/VASP homology 1 domain).

More specifically, domains in the meaning of the invention are Src homology 3 domains, WW domains, Ena/VASP homology 1 domains, GYF domains, UEV domains and/or profilin.

The EVH1 domain is constituted of about 115 amino acids and occurs in a variety of multidomain signalling proteins. Amongst others, these include the family of Ena/VASP proteins which function as molecular adaptors and modulate the actin dynamics of the cytoskeleton. The EVH1 domains are divided into three classes according to their ligand preference. The first class specifically recognizes particularly an FPPPP core motif which is found in all focal adhesion proteins such as vinculin and zyxin as well as in the ActA protein of the intracellular bacterium *Listeria monocytogenes*.

To investigate the processes on a molecular level and the resulting biological mode of function, the three-dimensional domain structure was elucidated and, in addition, the interaction with various ligand peptides was investigated. It was found that the EVH1 domains recognize a consensus core motif, FPxφP, wherein phenylalanine (F) and the two outer proline positions (P) are essential to bond formation and the two inner positions definitely allow variations (x=arbitrary amino acid, φ=hydrophobic amino acid). This can be seen in FIG. 2 wherein the class I EVH1 domain of the human VASP protein was investigated together with a short section from the ActA peptide ($_{332}$SFEFPPPPTEDEL$_{344}$). The central FPPPP motif and an affinity-enhancing EL epitope are in frames and show a clear influence on the binding strength when substituting individual positions with natural amino acids (dark=good binding; bright=no binding).

The possibility of replacing the positions $P_0$ and $P_1$ with other amino acids, with $P_0$ in particular being completely unspecific, can be explained when considering the ligand peptide in the binding mode: while $P_1$ and $P_2$ are received in a hydrophobic binding pocket of the domain, the two central prolines are situated in a screen-like position above the domain and have barely contact with the domain surface. However, the carbonyl group of $P_0$ forms an essential hydrogen bridge to the NH of the tryptophan residue W23 of the EVH1 domain.

Using a series of different test ligand peptides, it was also possible to gain an overview over the binding affinities. The highest observed binding affinity ($K_D$=45 μM) is furnished by the ligand $_{332}$SFEFPPPPTEDEL$_{344}$ (third of the four proline-rich repeats of the ActA protein). In contrast, when reducing the ligand to the core motif FPPPPT, there was no measurable affinity to the VASP/EVH1 domain anymore, while binding to the Mena/EVH1 domain was very weak, but still detectable (417 μM).

In a preferred embodiment of the invention the compounds are used as polyproline mimetics. Advantageously, proline-rich amino acid sequences are found especially in peptides involved in signal transduction processes, particularly in intracellular signal transduction processes. In the meaning of the invention the term "mimetics" can also be understood as "analogs". The compounds according to the invention are preferably used in the treatment of diseases associated with a modification of intracellular signal transduction processes mediated by polyproline helical structures, said diseases being selected from the group comprising bacterial and/or viral infectious diseases, neurodegenerative diseases and/or tumor diseases.

Other diseases in the meaning of the invention that can be treated with the agents according to the invention are selected from the group comprising monkey pox, AIDS, anthrax (*Bacillus anthracis*, milzbrand), avian influenza, borreliosis, *Borrelia recurrentis*, botulism (*Clostridium botulinum*), brucellosis, *Campylobacter* infections, chlamydial infections, cholera (*Vibrio cholerae*), Creutzfeldt-Jakob disease, *Coxiella burnetii* (Q fever), *Cryptosporidium parvuum* (cryptosporidiosis), dengue fever, diphtheria, ebola viral infections, echinococcosis (fox tapeworm, dog tapeworm), EHEC infections (STEC infections, VTEC infections), enterovirus, typhoid fever, (*Rickettsia prowazeckii*), *Francisella tularensis* (tularemia), spring-summer meningoencephalitis (SSME), yellow fever, giardiasis, gonorrhea, flu (influenza), *Haemophilis influenzae*, hantavirus, *Helicobacter pylori*, hepatitis C, hepatitis D, hepatitis E, herpes, HUS (hemolytic uremic syndrome), epidemic keratoconjunctivitis, pertussis, polio (poliomyelitis), infestation with head lice, infestation with itch-mites, Crimean-Congo fever, Lassa fever, food-related diseases, legionnaires' disease, leishmaniosis, lepra, leptospirosis, listeriosis, Lyme disease, *Lymphogranuloma venereum*, malaria (plasmodial infections), Marburg virus infections, measles, melioidosis, meningococcosis, MRSA (staphylococci), mumps, mycosis (fungus infections), new infectious diseases of increasing incidence, norovirus, ornithosis (parrot disease), papilloma virus, paratyphoid fever, plague (*Yersinia pestis*), pneumococcidal infections (*Streptococcus pneumoniae*), smallpox, travel-related infectious diseases, beef tapeworm infection in humans, rotavirus, German measles, RSV infections, salmonellosis, scarlet fever, severe acute respiratory syndrome (SARS), sexually communicable infections, shigellosis, syphilis, tetanus, rabies, toxoplasmosis, trichinosis, tuberculosis, typhoid fever, varicella (chickenpox), variant Creutzfeldt-Jakob disease, viral hemorrhagic fever, West-Nile fever, yersiniosis and/or diseases communicated by ticks.

The invention relates to the use of the agents according to the invention as drugs. In the meaning of the invention the agents according to the invention can therefore be used throughout the entire field of medicine, especially as pharmaceutical agents.

In a preferred fashion the bacterial diseases are diseases associated with and particularly mediated by the following bacteria: legionellas, streptococci, staphylococci, klebsiellas, *Haemophilis influenzae*, rickettsiae (typhoid fever), mycobacteria, mycoplasmas, ureaplasmas, neisseriae (meningitis, Waterhouse-Friedrichsen syndrome, gonorrhea), pseudomonads, bordetellas (pertussis), corynebacteria (diphtheria), chlamydiae, campylobacteria (diarrhea), *Escherichia coli*, proteus, salmonellas, shigellas, yersiniae, vibrions, enterococci, clostridiae, borreliae, *Treponema pallidum*, brucellas, francisellas and/or *Leptospira*, particularly listeriae.

Particularly preferred diseases are those induced by listeriae selected from the group comprising *L. monocytogenes* Sv1/2a, *L. monocytogenes* Sv4b F2365, *L. monocytogenes* Sv4b H7858, 178 contigs, *L. monocytogenes* Sv1/2a F6854, 133 contigs, *L. monocytogenes* Sv4b, *L. monocytogenes* Sv4a, *L. innocua* Sv6a, *L. welshimeri* Sv6b, *L. seeligeri* Sv1/2b and/or *L. ivanovii* Sv5 or essentially based on the above-mentioned preferred listeriae.

The preferred neurodegenerative diseases are selected from the group comprising Alzheimer's disease, Parkinson's disease, Huntington's disease and/or amyotrophic lateral sclerosis (ALS).

Furthermore, neurodegenerative diseases in the meaning of the invention are Alexander's disease, Alpers-Huttenlocher syndrome, Huntington's chorea, Creutzfeldt-Jakob disease, extrapyramidal syndrome, Friedreich's ataxia, corticobasal degeneration, Krabbe's disease, leukodystrophy, Lewy body dementia, mask face, Pick's disease, multiple sclerosis, multisystem atrophy, neurodegenerative iron deposits in the brains, progressive supranuclear gaze palsy, Shy-Drager syndrome, spinocerebellar ataxia, synucleinopathy and/or tropical spastic paraparesis.

Preferred tumor diseases are selected from the group comprising tumor diseases of the ear-nose-throat region, of the lungs, mediastinum, gastrointestinal tract, urogenital system, gynecological system, breast, endocrine system, skin, bone and soft-tissue sarcomas, mesotheliomas, melanomas, neoplasms of the central nervous system, cancerous diseases or tumor diseases during infancy, lymphomas, leukemias, paraneoplastic syndromes, metastases with unknown primary tumor (CUP syndrome), peritoneal carcinomatoses, immunosuppression-related malignancies and/or tumor metastases.

More specifically, the tumors may comprise the following types of cancer: adenocarcinoma of breast, prostate and colon; all forms of lung cancer starting in the bronchial tube; bone marrow cancer, melanoma, hepatoma, neuroblastoma; papilloma; apudoma, choristoma, branchioma; malignant carcinoid syndrome; carcinoid heart disease, carcinoma (for example, Walker carcinoma, basal cell carcinoma, squamobasal carcinoma, Brown-Pearce carcinoma, ductal carcinoma, Ehrlich tumor, in situ carcinoma, cancer-2 carcinoma, Merkel cell carcinoma, mucous cancer, non-parvicellular bronchial carcinoma, oat-cell carcinoma, papillary carcinoma, scirrhus carcinoma, bronchio-alveolar carcinoma, bronchial carcinoma, squamous cell carcinoma and transitional cell carcinoma); histiocytic functional disorder; leukemia (e.g. in connection with B cell leukemia, mixed-cell leukemia, null cell leukemia, T cell leukemia, chronic T cell leukemia, HTLV-II-associated leukemia, acute lymphocytic leukemia, chronic lymphocytic leukemia, mast cell leukemia, and myeloid leukemia); malignant histiocytosis, Hodgkin disease, non-Hodgkin lymphoma, solitary plasma cell tumor; reticuloendotheliosis, chondroblastoma; chondroma, chondrosarcoma; fibroma; fibrosarcoma; giant cell tumors; histiocytoma; lipoma; liposarcoma; leukosarcoma; mesothelioma; myxoma; myxosarcoma; osteoma; osteosarcoma; Ewing sarcoma; synovioma; adenofibroma; adenolymphoma; carcinosarcoma, chordoma, craniopharyngioma, dysgerminoma, hamartoma; mesenchymoma; mesonephroma, myosarcoma, ameloblastoma, cementoma; odontoma; teratoma; thymoma, chorioblastoma; adenocarcinoma, adenoma; cholangioma; cholesteatoma; cylindroma; cystadenocarcinoma, cystadenoma; granulosa cell tumor; gynadroblastoma; hidradenoma; islet-cell tumor; Leydig cell tumor; papilloma; Sertoli cell tumor, theca cell tumor, leiomyoma; leiomyosarcoma; myoblastoma; myoma; myosarcoma; rhabdomyoma; rhabdomyosarcoma; ependymoma; ganglioneuroma, glioma; medulloblastoma, meningioma; neurilemmoma; neuroblastoma; neuroepithelioma, neurofibroma, neuroma, paraganglioma, non-chromaffin paraganglioma, angiokeratoma, angiolymphoid hyperplasia with eosinophilia; sclerotizing angioma; angiomatosis; glomangioma; hemangioendothelioma; hemangioma; hemangiopericytoma, hemangiosarcoma; lymphangioma, lymphangiomyoma, lymphangiosarcoma; pinealoma; cystosarcoma phylloides; hemangiosarcoma; lymphangiosarcoma; myxosarcoma, ovarial carcinoma; sarcoma (for example, Ewing sarcoma, experimentally, Kaposi sarcoma and mast cell sarcoma); neoplasms (for example, bone neoplasms, breast neoplasms, neoplasms of the digestive system, colorectal neoplasms, liver neoplasms, pancreas neoplasms, hypophysis neoplasms, testicle neoplasms, orbital neoplasms, neoplasms of the head and neck, of the central nervous system, neoplasms of the hearing organ, pelvis, respiratory tract and urogenital tract); neurofibromatosis and cervical squamous cell dysplasia.

In another preferred embodiment the cancerous disease or tumor is selected from the group of tumors of the ear-nose-throat region, comprising tumors of the inner nose, nasal sinus, nasopharynx, lips, oral cavity, oropharynx, larynx, hypopharynx, ear, salivary glands, and paragangliomas, tumors of the lungs comprising non-parvicellular bronchial carcinomas, parvicellular bronchial carcinomas, tumors of the mediastinum, tumors of the gastrointestinal tract, comprising tumors of the esophagus, stomach, pancreas, liver, gallbladder and biliary tract, small intestine, colon and rectal carcinomas and anal carcinomas, urogenital tumors comprising tumors of the kidneys, ureter, bladder, prostate gland, urethra, penis and testicles, gynecological tumors comprising tumors of the cervix, vagina, vulva, uterine cancer, malignant trophoblast disease, ovarial carcinoma, tumors of the uterine tube (Tuba Faloppii), tumors of the abdominal cavity, mammary carcinomas, tumors of the endocrine organs, comprising tumors of the thyroid, parathyroid, adrenal cortex, endocrine pancreas tumors, carcinoid tumors and carcinoid syndrome, multiple endocrine neoplasias, bone and soft-tissue sarcomas, mesotheliomas, skin tumors, melanomas comprising cutaneous and intraocular melanomas, tumors of the central nervous system, tumors during infancy, comprising retinoblastoma, Wilms tumor, neurofibromatosis, neuroblastoma, Ewing sarcoma tumor family, rhabdomyosarcoma, lymphomas comprising non-Hodgkin lymphomas, cutaneous T cell lymphomas, primary lymphomas of the central nervous system, Hodgkin's disease, leukemias comprising acute leukemias, chronic myeloid and lymphatic leukemias, plasma cell neoplasms, myelodysplasia syndromes, paraneoplastic syndromes, metastases with unknown primary tumor (CUP syndrome), peritoneal carcinomatosis, immunosuppression-related malignancy comprising AIDS-related malignancy such as Kaposi sarcoma, AIDS-associated lymphomas, AIDS-associated lymphomas of the central nervous system, AIDS-associated Hodgkin's disease and AIDS-associated anogenital tumors, transplantation-related malignancy, metastasized tumors comprising brain metastases, lung metastases, liver metastases, bone metastases, pleural and pericardial metastases, and malignant ascites.

In another preferred embodiment the cancerous disease or tumor is selected from the group comprising cancerous diseases or tumor diseases such as mammary carcinomas, gastrointestinal tumors, including colon carcinomas, stomach carcinomas, pancreas carcinomas, colon cancer, cancer of the small intestine, ovarian carcinomas, cervical carcinomas, lung cancer, prostate cancer, renal cell carcinomas and/or liver metastases.

Viral diseases in the meaning of the invention are selected from the group comprising influenza, rhinitis, cough, measles, mumps, German measles, infectious erythema, three-day fever, chickenpox, Pfeiffer's glandular fever, SARS, cytomegaly, diarrhea, hepatitis, polio, herpes labialis, warts, rabies, Lassa fever, Ebola, Marburg fever, hantavirus fever, SSME, RSSE, louping ill encephalitis, Powassan encephalitis, Kyasanur forest fever, Omsk hemorrhagic fever, Colorado tick fever, yellow fever, dengue fever, Japanese encephalitis, West-Nile fever, Chikungunya fever, O'nyong-nyong fever, Rift Valley fever, sand fly fever, Ross River fever, Sindbis fever, Mayaro fever, Murray Valley encephalitis, St. Louis encephalitis, Rocio encephalitis, California encephalitis, Bunyamwera fever, Oropouche fever, AIDS, herpes genitalis and/or herpes simplex, and in a preferred fashion the viral hepatitis diseases are selected from the group comprising hepatitis A, hepatitis B, hepatitis C, hepatitis D, hepatitis E, hepatitis F, hepatitis G and/or autoimmune hepatitis and/or asymptomatic or symptomatic HIV infections.

HIV infections may give rise to the disease of AIDS. In the meaning of the invention, AIDS is characterized or classified by a clinical picture selected from the group comprising (a) asymptomatic or symptomatic HIV infections;

(b) bacillary angiomatosis, inflammations of the small pelvis, especially during complications of a tube or ovarian abscess, extended or relapsing herpes zoster, thrombocytopenic purpura, long-lasting fever or diarrhea lasting longer than one month, listeriosis, oral hairy leukoplakia, oropharyngeal candidoses, vaginal candidoses, chronic or difficult to treat, cervical dysplasias, in situ carcinoma, peripheral neuropathy and/or (c) candidoses of the respiratory tract or esophagus, cytomegaly virus infections, CMV retinitis, HIV-related encephalopathy, herpes simplex with chronic ulcer (>1 month) or herpes simplex-related bronchitis, pneumonia or esophagitis, chronic histoplasmosis, intestinal isosporosis, Kaposi's sarcoma, disseminated or extrapulmonal coccidiomycosis, extrapulmonal cryptococcosis, chronic intestinal cryptosporidiosis, immunoblastic, primarily cerebral or Burkitt lymphoma, extrapulmonal mycobacteria, pneumocystic pneumonia, relapsing bacterial pneumonia, progressive multifocal leukoencephalopathy, relapsing *salmonella* septicemia, tuberculosis, cerebral toxoplasmosis, Wasting syndrome and/or invasive cervical carcinoma.

Treatment in the meaning of the invention is prophylaxis, therapy, follow-up and/or aftercare of diseases.

The agent according to the invention can be employed alone or in combination with other agents against enveloped as well as non-enveloped viruses. Enveloped viruses are preferably:

Double-Stranded DNA Viruses=dsDNA
Family Poxyiridae
    Subfamily Chordopoxyirinae
        Genus Orthopoxvirus
            Orthopox variola virus=smallpox virus—smallpox
            Orthopox alastrim virus—whitepox
        Genus Parapoxvirus
            Parapox ovis virus=Orf virus—Orf=sheeppox, in animals, transmittable to humans
        Genus Molluscipoxvirus
            Molluscum contagiosum virus—epithelial molluscum (Molluscum contagiosum)
Family Herpesviridae
    Subfamily Alphaherpesvirinae
        Genus Simplexvirus
            Herpes simplex virus 1 (HSV 1)=human herpes virus 1 (HHV 1)—herpes simplex, herpes labialis, aphthous stomatitis
            Herpes simplex virus 2 (HSV 2)=human herpes virus 2 (HHV 2)—herpes simplex, herpes genitalis
            Herpes B virus=(Herpesvirus simiae)
        Genus Varicellovirus
            Varicella zoster virus (VZV)=human herpes virus 3 (HHV 3)—chickenpox=varicella (herpes zoster), shingles
            pseudorabies virus—mad itch=scratching pest, transmittable to humans Subfamily Betaherpesvirinae
  Genus Cytomegalovirus
    Human cytomegaly virus=human cytomegaly virus (HCMV)=human herpes virus 5 (HHV 5)—cytomegaly
  Genus Roseolovirus
    Human herpes virus 6 (HHV 6)—three-day fever
    Human herpes virus 7 (HHV 7)—three-day fever
Subfamily Gammaherpesvirinae
  Genus Lymphocryptovirus
    Epstein-Barr virus (EBV)=human herpes virus 4 (HHV 4) Pfeiffer's glandular fever, Burkitt lymphoma
  Genus Rhadinovirus
    Human herpes virus 8 (HHV 8)—Kaposi's sarcoma
Family Hepadnaviridae
  Genus Orthohepadnavirus
    Hepatitis B virus (HBV)—hepatitis B
Single(+)-Stranded RNA Viruses=ss(+)RNA
Family Togaviridae
  Genus Alphaviruses—arbovirosis pathogen
    Chikungunya virus (CHIKV)—Chikungunya fever
    O'nyong-nyong virus (ONNV)—O'nyong-nyong fever
  Genus Rubiviruses
    Rubivirus=German measles virus=rubellavirus—German measles
Family Flaviviridae
  Genus Hepacivirus
    Hepatitis C virus (HCV)—hepatitis C
    GB virus C (no significant morbidity)
  Genus Flavivirus
    West-Nile virus—West-Nile fever
    Dengue virus—dengue fever
    Yellow fever virus—yellow fever
    Louping ill virus—louping ill encephalitis
    St. Louis encephalitis virus—St. Louis encephalitis
    Japanese B encephalitis virus—Japanese encephalitis
    Powassan virus—Powassan encephalitis
    RSSE virus—RSSE=Russian spring-summer encephalitis
    SSME virus SSME=spring-summer meningoencephalitis
Family Coronaviridae—gastrointestinal inflammations
  Genus Coronavirus
    SARS-associated corona virus (SARS-CoV)—SARS=atypical pneumonia
    Human corona virus 229E (HCoV 229E)—cold
    Human corona virus OC43 (HCoV OC43)—cold
  Genus Torovirus—gastroenteritis
Family Retroviridae=single(+)-stranded RNA viruses with dsDNA intermediate:
  Subfamily Orthoretrovirinae
    Genus Deltaretrovirus
      Human T cell lymphotropic virus type I (HTLV I)—leukemia
      Human T cell lymphotropic virus type II (HTLV II)—leukemia
    Genus Lentivirus
      Human immunodeficiency virus type 1 (HIV-1)—AIDS
      Human immunodeficiency virus type 2 (HIV-2)—AIDS
Single(−)-Stranded RNA Viruses=ss(−)RNA
Family Arenaviridae
  Genus Arenavirus
    Lassa virus—Lassa fever
    Lymphocytic choriomeningitis virus (LCMV)—choriomeningitis
    Tacaribe virus
    Junin virus—Junin fever (Argentinean hemorrhagic fever)
    Machupo virus—Machupo fever (Bolivian hemorrhagic fever)
Family Bornaviridae
  Genus Bornavirus
    Virus of Borna's disease—in horses, possibly transmittable to humans, affective disorders
Family Bunyaviridae—Arbovirosis pathogen
  Genus Orthobunyavirus
    Bunyamwera virus (serogroup)
    California encephalitis virus (serogroup)—encephalitis
  Genus Phlebovirus
    Rift Valley fever virus—3 subtypes, Rift Valley fever
    Sandfly fever virus—sandfly fever
    Subtype Toscana virus—Pappataci fever
  Genus Nairovirus
    Krim Congo fever virus (serogroup):
      Subtype Krim Congo hemorrhagic fever virus—Krim Congo fever
      Subtype Hazara virus
      Subtype Khasan virus
  Genus Hantavirus
    Hantaan virus (4 subtypes)—hemorrhagic fever, nephritis
    Seoul virus (serogroup)—hemorrhagic fever
    Prospect-Hill virus (2 subtypes)—hemorrhagic fever
    Puumala virus (serogroup)—hemorrhagic fever, pneumonia, nephritis
    Dobrava-Belgrade virus—hemorrhagic fever
    Tula virus—hemorrhagic fever
    Sin-Nombre virus (serogroup)—hemorrhagic fever with severe pulmonary edema
Family Filoviridae
  Genus Marburg virus
    Lake Victoria-Marburg virus (serogroup)—Marburg fever (hemorrhagic fever)
  Genus Ebolavirus
    Zaire Ebola virus (serogroup)—ebola (hemorrhagic fever)
    Sudan Ebola virus—ebola (hemorrhagic fever)
    Ivory Coast Ebola virus—Ebola (hemorrhagic fever)
Family Orthomyxoviridae
  Genus Influenza virus A—influenza
    Influenza virus A variant (H1N1)—influenza
    Influenza virus A variant (H3N2)—influenza (avian) influenza virus A variant (H5N1), highly pathogenic avian influenza virus (HPAIV)—avian influenza, in animals, also transmittable to humans, but no human-to-human transmission
  Genus Influenza virus B—influenza
    Influenza virus B/Victoria line—influenza
    Influenza virus B/Yamagata line—influenza
  Genus Influenza virus C—influenza
Family Paramyxoviridae
  Subfamily Paramyxovirinae
    Genus Avulavirus
      Parainfluenza virus (1,3)—parainfluenza
    Genus Morbillivirus
      Measles virus—measles
    Genus Rubulavirus
      Parainfluenza virus (2,4)—parainfluenza
      Mumps virus—mumps Subfamily Pneumovirinae
  Genus Pneumovirus
    Respiratory syncytical virus (RSV)—infection of the respiratory tract
  Genus Metapneumovirus
    Human metapneumovirus (HMPV)—infection of the respiratory tract
Family Rhabdoviridae
  Genus Vesiculovirus
    Vesicular stomatitis Indiana virus (VSV)—Stomatitis vesicularis (pustular inflammation of the oral mucosa), in animals, also transmittable to humans
  Genus Lyssavirus
    Rabies virus (RABV) (formerly genotype 1)—rabies, in animals, also transmittable to humans
    Mocola virus (MOKV) (formerly genotype 3)—rabies, in animals, also transmittable to humans
    Duvenhage virus (DUVV) (formerly genotype 4)—rabies, in animals, also transmittable to humans
    European Bat Lyssa virus 1+2 (EBLV 1, 2) (formerly genotypes 5 and 6)—rabies, in animals, also transmittable to humans
    Australian Bat Lyssa virus (ABLV) (formerly genotype 7)—rabies, in animals, also transmittable to humans
Non-Enveloped Viruses are in Particular:
Double-Stranded DNA Viruses=dsDNA
  Adenoviridae
    Human adenoviruses A-F (51 subtypes)—rhinitis, colds, diarrhea
  Papovaviridae
    Papovavirus
      Human papilloma virus
        Miscellaneous human papilloma viruses (HPV)—warts
        Condyloma virus 6 (HPV 6)—figwarts
        Condyloma virus 11 (HPV 11)—figwarts
        Human papilloma virus, low-risk types (HPV 40, 42, 43, 44, 54, 61, 70, 72, 81 and GP6108; high-risk types (HPV 16, 18, 31 and 33, but also 35, 39, 45, 51, 52, 56, 58, 59, 68, 73 and 82) cervical carcinoma
      Polyomavirus
Single-Stranded DNA Viruses=ssDNA
  Parvoviridae
    Parvovirinae
      Dependovirus
        Adeno-associated virus 2 (AAV 2)
        Adeno-associated virus 3 (AAV 3)
        Adeno-associated virus 5 (AAV 5)
      Erythrovirus
        Parvovirus B19-infectious erythema
Double-Stranded RNA Viruses=dsRNA
  Reovirus
    Rotavirus—gastroenteritis, diarrhea
    Orbivirus
      Colorado tick virus—Colorado tick fever
      Epizootic hemorrhagic disease virus (EHDV)—enzootic hemorrhage of deer
Single(+)-Stranded RNA Viruses=ss(+)RNA
  Picornaviridae
    Rhinovirus
      Human rhinovirus (HRV), 1A, 1B-100—rhinitis, colds
    Aphthovirus
      Foot-and-mouth disease virus—foot-and-mouth disease in animals, transmittable to humans even in mild form
    Enterovirus
      Poliovirus (1-3)—polio
      Coxsackie virus A 1-22, 24 (CVA 1-22, 24)—colds, viral meningitis, myocarditis
      Coxsackie virus B 1-6 (CVB 1-6) colds, viral meningitis, myocarditis
      Echoviruses—colds, gastroenteritis=diarrhea, meningoencephalitis
      Human enteroviruses—colds, gastroenteritis=diarrhea
      SVD viruses (vesicular swine disease)
    Cardiovirus
      Encephalomyocarditis virus (EMCV)—encephalomyocarditis
      Mengovirus—encephalomyocarditis
      Theiler murine encephalomyelitis virus (TMEV)—encephalomyelitis
      Vilyuisk human encephalomyelitis virus (VHEV)—encephalomyelitis
    Hepatovirus
      Hepatitis A virus (HAV)—hepatitis A
  Hepeviridae
    Hepevirus
      Hepatitis E virus (HEV)—hepatitis E
  Caliciviridae
    Calicivirus
      SRSV=small rounded structured viruses
      Norwalk virus—gastroenteritis, diarrhea
      Norovirus—gastroenteritis, diarrhea
      Sapovirus—gastroenteritis, diarrhea
      Vesivirus
      Lagovirus
  Astroviridae
    Astrovirus
      Human Astrovirus—gastroenteritis, diarrhea In a preferred embodiment the agent according to the invention may comprise an additional agent selected from the group comprising abacavir, acyclovir, adefovir, amantadine, amprenavir, atazanavir, codofovir, darunavir, delavirdine, didanosine, docosanol, emtricitabine, efavirenz, enfuvirtide, entecavir, famciclovir, foscamet, fomivirsen, fosamprenavir, ganciclovir, gardasil, idoxuridine, imiquimod, indinavir, interferon, lamivudine, lopinavir, nevirapine, nelfinavir, oseltamivir, penciclovir, peramivir, ribavirin, rimantadine, ritonavir, saquinavir, stavudine, tenofovir, tipranavir, trifluridine, tromantadine, valaciclovir, valganciclovir, vidarabine, viramidine, zalcitabine, zanamivir and/or zidovudine.

The invention also relates to a set (kit) consisting of separate packages of:
a) an effective amount of the composition according to the invention and/or pharmaceutically useful derivatives, solvates and/or stereoisomers thereof as well as mixtures thereof with other or additional agents at any ratio, and
b) an effective amount of another drug. The set includes suitable containers such as boxes, single flasks, bags or ampoules. For example, the set can include single ampoules, each one containing an effective amount of the composition according to the invention and/or pharmaceutically useful derivatives, solvates and/or stereoisomers, including mixtures thereof at any ratio, as well as an effective amount of another medical active agent in dissolved or lyophilized form. Furthermore, the set may include information e.g. in the form of a package insert for combining the contents of the kit. Said information may also comprise a representation of a therapeutic regimen or the like.

In the foregoing description of the pharmaceutical compositions containing a preferred compound, the equivalent expressions "administration", "administration of", "administering" and "administering a." are used in relation to these pharmaceutical compositions. In the present context, these expressions are intended to mean providing a pharmaceutical composition according to the invention on any route of administration described herein to a patient in need of treatment, the active agent being a preferred compound or a prodrug, a derivative or a metabolite thereof which is suitable for the treatment of a disease, pathological disorder mediated by or associated with viral infection, or such an affection, in such a patient. The present invention therefore encompasses any other compound capable of directly or indirectly providing a preferred compound when administered to a patient. Such compounds are known as prodrugs, and there exist many established procedures for producing such prodrug forms of preferred compounds.

When treating the above-mentioned diseases it is particularly preferred that the pharmaceutical agent including the compounds according to the invention is prepared and/or used in the form of a gel, poudrage, powder, tablet, sustained-release tablet, premix, emulsion, brew-up formulation, drops, concentrate, granulate, syrup, pellet, bolus, capsule, aerosol, spray and/or inhalant.

In a preferred fashion the pharmaceutical agent comprising the compounds according to the invention is present in a preparation at a concentration of from 0.1 to 99.5, preferably from 0.5 to 95.0 and more preferably from 20.0 to 80.0 wt. %.

The preparation is preferably administered orally, subcutaneously, intravenously, intramuscularly, intraperitoneally and/or topically.

The pharmaceutical agent including the compounds according to the invention is preferably employed in total amounts of from 0.05 to 500 mg per kg, more preferably from 5 to 100 mg per kg body weight per 24 hours.

In a preferred fashion, contacting is effected orally, via injection, topically, vaginally, rectally and/or nasally.

There is a continuous demand for compounds which influence binding of structures including the above-mentioned domains (in the meaning of the invention the following domains are envisaged in particular: Src homology 3 domains, WW domains, Ena/VASP homology 1 domains, GYF domains, UEV domains and/or profilin) and the ligands thereof. It would therefore be desirable to provide the new compounds for testing in in vitro tests as well which, for example, could be used in pharmacological screening tests for specific lead compounds.

In another preferred embodiment the agents according to the invention are also provided as diagnostic agents comprising the agents of the invention and a detectable label conjugated with the agent directly, indirectly or via complex formation. The diagnostic agents can be used to detect the presence of Src homology 3 domains, VW domains, Ena/VASP homology 1 domains, GYF domains, UEV domains and/or profilin of a generic or specific type in cells, tissues or organs in vitro or in vivo. For in vivo uses, the diagnostic agent is administered enterally, parenterally, or on another route predetermined by the requirements of the particular application, preferably mixed with a pharmaceutically tolerable carrier.

In a special embodiment a test based on a fusion protein is used, for example, which comprises an agent according to the invention, e.g. incorporated in a peptide, and includes a substrate for e.g. deregulated or activated Src or a protein having any other of the above-mentioned domains (WW, Ena/VASP homology 1, GYF, UEV domains and/or profilin). For example, a sample to be tested for infection with a particular virus can be collected from a patient and incubated with an effective amount of the fusion protein. Subsequent analysis as to the degree of substrate conversion allows potential detection of a viral infection in the individual. Consequently, the presence of a virus causing expression of e.g. deregulated or activated Src can be indicated by unusually high levels of e.g. Src which are detected via high quantities of converted substrate.

The invention also relates to a kit comprising at least one of the compounds according to the invention and/or one of the pharmaceutical agents according to the invention, optionally together with information concerning handling or combining the contents of the kit, e.g. an instruction leaflet or an internet address referring to homepages including further information, etc. For example, the information concerning handling the kit may comprise a therapeutic regimen for the above-mentioned diseases, particularly the preferred diseases. Also, the information may comprise details referring to the mode of use of the products according to the invention in diagnosing the above-mentioned diseases. The kit according to the invention may also be used in basic research.

Accordingly, the invention also relates to the use of the kit in the prophylaxis and/or therapy of neurodegenerative diseases, bacterial infectious diseases or tumor diseases.

The invention also relates to the use of the agents according to the invention for screening for peptide binders. A person of average skill in the art is familiar with screening methods using peptide mimetics.

The agents according to the invention can also be incorporated as building blocks in peptides, especially e.g. in immobilized peptides. In particular, such immobilized peptides can be used in diagnostics with advantage. For example, the immobilized peptides can be immobilized on gold by immobilizing the agents of the invention on gold particles. The immobilized or non-immobilized peptides or other molecules comprising the agents according to the invention as building blocks can be used e.g. for screening for substances involved in protein-protein interactions or peptide-peptide interactions. A preferred use, for example, is use of the peptides comprising the agents according to the invention or use of the agents according to the invention in combination with carbohydrates or lipids in affinity columns. Those skilled in the art will also be familiar with other possible ways of achieving immobilization. Immobilization in the meaning of the invention involves various methods of fixing the agents according to the invention, which can be achieved particularly by exposure to biological, chemical or physical action. For example, the agents according to the invention can be fixed by binding to a carrier, but also by crosslinking, inclusion, or by incorporating in microcapsules. In the event of binding to a carrier, e.g. in a microtiter plate or a chromatographic column, fixing is effected by adsorption, ionic binding or covalent binding. The agents according to the invention can be fixed via spacers or antibodies. In the event of inclusion in a semipermeable membrane, fixing takes place in the form of inclusion in gels, microcapsules or fibers.

Using the above-mentioned affinity columns, it is possible to detect interacting reactants by determining proteins which interact as specific binders. Of course, it is also possible to incorporate the agents according to the invention in non-peptidic structures such as esters or sulfonamides, sugars or other organic or inorganic compounds. In a preferred fashion this results in organic modules which can be used for screening for specific binders.

For example, it may be preferred to combine the agents according to the invention with other substances such as disclosed in WO 2007/021661, for example. The combination of compounds disclosed therein with the agents according to the invention results in new combination molecules which exhibit surprising properties. Surprisingly, the new combination molecules are highly useful as targets in screening assays. Such applications can be utilized e.g. in a screening for components which interact e.g. with the SH3 domain or modulate, especially inhibit, protein interactions if at least one of the above-mentioned domains is involved. A person skilled in the art will be familiar with possible ways of combining or associating the agents according to the invention especially with substances of WO 2007/021661 in accordance with claims 1 to 11 or in accordance with 41 to 44 or other disclosed compounds, so that use particularly in screening assays is possible. For example, claim 1 of WO 2007/021661 discloses the position of an amino acid or analogous peptide mimetic. This position can be occupied by at least one of the agents according to the invention or by a compound comprising the compounds according to the invention. In a preferred fashion the agents according to the invention can be used as scaffolds, e.g. in substances included in a library, for example, or in structure-optimized targets. The new combination molecules can be used as ligands for SH3 or FYN domains. In addition to the agents according to the invention, combinations thereof and compounds in accordance with WO 2007/021661 can be used to influence the activity of proteins comprising a SH3 domain or including an EVH1, GYF, WW or a UEF and/or profilin domain. In this context the SH3 domain is preferably part of a protein kinase, for example, and in another preferred embodiment the protein kinase is a member of the Src family.

Members of the Src family are, for example, FYN, Src, Fgr, Yes, Yrk, Lyn, Hck, Lck or Blk. The agents according to the invention as well as the combination molecules comprising the same can be used in the treatment of diseases wherein e.g. members of the Src family or proteins with the above-mentioned domains are involved. More specifically, these include in particular cardiovascular diseases, inflammatory diseases, immune diseases, bone diseases, diseases with a proliferative background such as, in particular, cancerous diseases, neurological diseases, neurodegenerative diseases, ischemia, especially following stroke, disorders in angiogenesis, allergies, arthritis or infectious diseases. Therefore, the invention also relates to a library, especially a library that can be used for combinatory screening methods, which comprises the agents according to the invention or molecules comprising the same. Using these libraries, it is possible e.g. to detect candidate molecules which bind to SH3 domains or to other of the above-mentioned domains.

SH3 domains can be detected in a variety of proteins, including but not limited to Abl, Src, Grb2, PLCδ, PLCγ, Ras-GAP, Nck and p85-PI-3' kinase.

The invention also relates to the use of the agents according to the invention in isolated form or of agents combined with organic or inorganic compounds as probes which transport the substances in a directed manner. In this context they can be employed not only as therapeutic agents but also as diagnostic agents. The agents according to the invention can also be used as probes or as drug delivery systems to transport the desired compounds preferably to the above-mentioned domains or allow increased interaction with each other.

The agents according to the invention are ligands or binders for the above-mentioned domains. Surprisingly, the agents according to the invention show a far higher level of affinity to the above-mentioned domains compared to well-known ligands or binders. Apart from the above-mentioned therapeutic uses, the binding or interacting agents according to the invention can also be used in research in a variety of ways, e.g. in providing a method for modulating signal transduction pathways, especially on a cellular level, modelling the activity of oncogenic proteins or other disease-associated structures, or providing lead compounds in addition to the above-mentioned drugs, including the development of diagnostic agents on a laboratory scale. Advantageously, the agents according to the invention exhibit the ability of modulating a large number of proteins, especially those involved in signal transfer. The agents according to the invention, provided they have the above-mentioned domains, also offer the advantage of allowing modulation of wide classes as well as highly specific classes of proteins. Using routine tests, it is therefore possible to select agents according to the invention which are specific for particular domains, thus being capable of modulating the modulation of a particular protein, while having no influence on others bearing similar or identical domains. Of course, the agents according to the invention can also be selected in such a way that both broad and specific classes of domains are influenced by modulating the overall activity of the respective proteins. Consequently, the agents according to the invention also serve as useful lead classes in the production of other e.g. peptidometric active agents modulating extensive classes of proteins involved in signal transduction pathways or in e.g. oncogenesis or neurodegenerative diseases as well as viral and bacterial infectious diseases. Thus, the invention provides new motifs reflecting the variations in selectivity or specificity in binding the above-mentioned domains.

Therefore, the present invention also relates to conjugates of the inventive agents with a second molecule or a second chemical group which may include amino acids, sugars, carbohydrates or inorganic structures. In particular, the second molecule can be any substance that is intended to be administered to the region of the domain of a particular protein. This may also include cells containing said protein. Possible target cells include but are not limited to neural cells, immune cells (e.g. T cells, B cells, natural killer cells and the like), osteoclasts, blood platelets, epidermal cells and the like, said cells expressing particularly the above-mentioned domains or related proteins. In this way it is possible to achieve specific modulation of the activities of proteins having the above-mentioned domains.

The molecules according to the invention or structures comprising the same can be used in a method for modulating the activity e.g. of Src or Src-related proteins, which method comprises administration of a composition comprising an effective amount of the agents according to the invention together with e.g. a carrier. However, modulating the activity not only involves Src but also all those molecules having the above-mentioned domains (Src homology 3 domains, WW domains, Ena/VASP homology 1 domains, GYF domains, UEV domains and/or profilin). In preferred embodiments of the invention the method being considered results in inhibition of the activity of proteins comprising the above-mentioned domains. In other preferred embodiments the method is effective in activating proteins having the above-mentioned domains.

Moreover, the agents according to the invention can be used in other fields such as methods of imaging cells, tissues and organs wherein proteins with the above-mentioned domains are expressed, said methods comprising in particular administration of an effective amount of the inventive composition having the agents according to the invention conjugated with a detectable marker or an imaging agent.

Thus, the invention also provides tests for identifying a compound which influences binding between a first molecule comprising the above-mentioned domains and a second molecule which binds to these domains, the second molecule preferably being an agent according to the invention, the tests comprising incubation of one or more candidate compounds, among which selection of such a compound is desired, with the first molecule and the second molecule under conditions promoting binding and detection of the one or more compounds which influence binding of the first molecule to the second molecule.

The agents according to the invention may also be provided in the form of kits for performing such tests, said kits comprising a first molecule which includes the above-mentioned domains and a second molecule which binds to these domains, the second molecule being an agent according to the invention.

The molecules according to the invention show a wide range of biological activities, comprising enhancement or inhibition (depending on the particular peptide or the nature of the target molecule) of the natural function or biological function of a target molecule of the agents according to the invention.

Another object of the present invention is to provide tests using the new substances of the invention, which tests would allow to determine whether a candidate compound is capable of influencing binding between the above-mentioned domains and a ligand for these domains. A compound having the ability to modify such binding would be useful as agent for modulating the pharmacological activity of structures including the above-mentioned domains. The present invention provides suitable ligands for these domains for use in such tests. Surprisingly, the agents according to the invention were found to be remarkably suitable for use in such tests. Accordingly, the invention also provides methods for the identification of compounds influencing binding of a molecule which comprises the above-mentioned domains and a ligand of the domain, said ligand of the domain being the agent according to the invention. In total, the effect on binding can increase or decrease the binding affinity. In a preferred fashion the effect is an inhibition, e.g. in the form of reduction or loss of binding.

Therefore, the invention also relates to a method of identifying an inhibitor of binding between a molecule comprising the above-mentioned domains and a second molecule comprising at least one agent according to the invention. Said method also comprises incubation of at least one or more compounds, among which an inhibitor/activator is to be selected, with the first molecule and a molecule according to the invention under conditions promoting binding. The method also comprises detection of said one or more compounds inhibiting binding of the first molecule to the molecule according to the invention. Consequently, a test according to the invention would be constituted of at least one molecule comprising one of the above-mentioned domains, at least one of the agents according to the invention, incorporated e.g. in a peptide or other structure, and one candidate compound assumed to have the capability of influencing binding between the first molecule and the ligand according to the invention. In addition, the test may include an agent for the detection of binding between the first molecule and the ligand in accordance with the invention. For example, such agents can be detectable labels linked with the first molecule, the ligand according to the invention or the candidate compound. In a preferred embodiment, a method wherein the test in the meaning of the invention is employed comprises the following steps:

contacting the domain with the agent according to the invention under conditions suitable for binding in the presence of a candidate compound and measuring the extent of binding between the domain and the ligand;

comparing the extent of binding measured in the first step with the extent of binding which is known or has been determined to exist between the domain and the agent according to the invention in the absence of a candidate compound, a difference between the extent of binding measured in the first step and the extent of binding which is known or has been determined to exist between the domain and the agent according to the invention in the absence of a candidate compound indicating that the candidate compound is a compound that influences binding between the molecule comprising the domain and the agent according to the invention.

The method may comprise an additional step which comprises formulating the detected candidate molecule into a pharmaceutically acceptable form.

In all the above-mentioned methods and tests the agents according to the invention can be used as substance components in a library intended e.g. to detect defined targets.

In a likewise preferred fashion the agents according to the invention are used to produce optimized targets, especially targets optimized with respect to their structure, which have the agent according to the invention and, advantageously, a folding that improves the interaction with molecules to be tested.

It will be appreciated that the agents according to the invention can also be combined with other mimetics or peptide mimetics; combinations with amino acids or organic molecules are also advantageous.

The teaching according to the present application is remarkable for the following features:

Departure from conventional technologies

New field of problems

Existence of a long-unsatisfied, urgent need for the solution of the problem solved by the invention Hitherto vain efforts in the art Simplicity of a particular solution indicates inventive activity, especially as it replaces more complicated teachings Development in scientific technology has proceeded in a different direction Achievement that rationalizes development Erroneous ideas in the art on the solution of the problem at issue (prejudice)

Technical progress, e.g. improvement, performance enhancement, lower expense, savings of time, materials, work steps, cost or raw materials difficult to obtain, enhanced reliability, elimination of flaws, superior quality, maintenance freedom, greater efficiency, higher yield, expansion of the technical scope, provision of a further means, creation of a second approach, creation of a new field, first-time solution of a problem, reserve means, alternatives, scope for rationalization, automation and miniaturization, or enrichment of the range of available drugs Fortunate choice out of a variety of possibilities because one has been selected, the result of which has not been predictable, this therefore being a patentable fortunate choice Errors in the technical literature or highly contradictory representation of the subject matter of the invention Young field of technology Combination invention, i.e., several known elements have been combined to achieve a surprising effect Issue of licenses Praise in the art Economic success.

More specifically, the advantageous embodiments of the invention have at least one or more of the above-mentioned advantages.

DETAILED DESCRIPTION OF VARIOUS AND PREFERRED EMBODIMENTS

Figure 1:
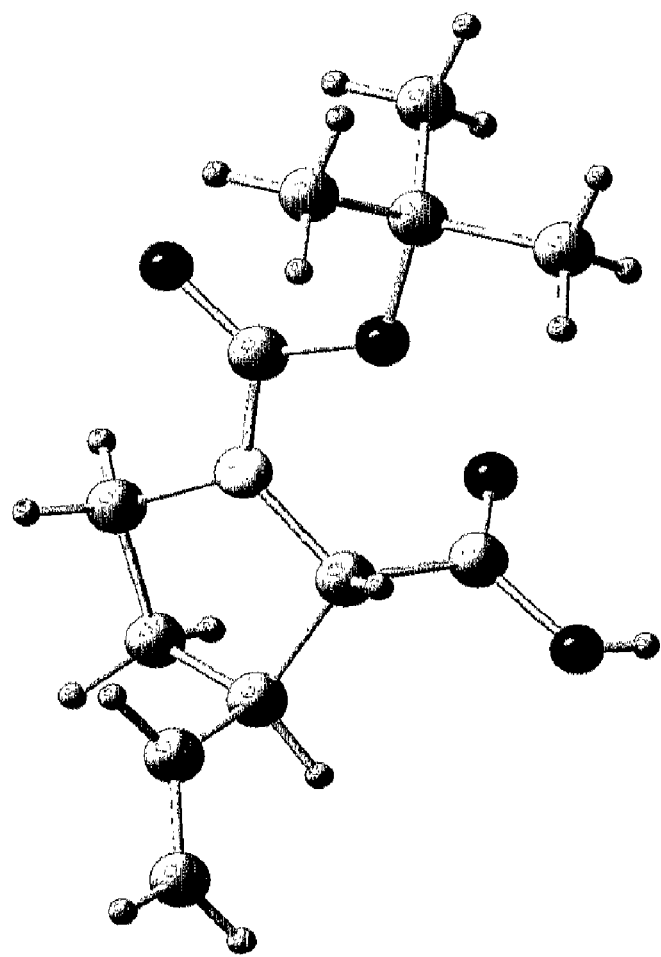
FIG. 1 shows the crystal structure of the N-Boc-protected trans-3-vinylproline 166.

Without intending to be limiting, the invention will be explained in more detail with reference to the synthesis of the diproline mimetic 85.

The motivation was searching for molecules capable of binding to the EVH1 domain with high affinity, thereby replacing the native proline-rich sequences of the ligand peptide as binding partner. On the basis of molecular modelling studies relating to the interaction of ligand peptides with the VASP/EVH1 domain, compound 85 was designed which, being a promising module (dipeptide mimetic), could be incorporated in test peptides to replace two adjacent proline positions of the FPPPP core motif therein. The guidelines of the structural design were (1) a geometrically fixed, helical structure (tricyclic moiety), (2) maximum possible conformity of bond angles and lengths compared to the natural proline-proline dipeptide (in the PPII helical conformation), (3) a central hydrogen bridge acceptor function in the form of a carbonyl group, and (4) an amino acid-like overall structure with an Fmoc-protected N terminus and a free C terminus to make the desired incorporation in peptides methodically simple. These requirements are met by molecule 85 represented below, which is a conformationally restricted analog of two consecutive prolines in the PPII helix. As a result of incorporating the Z-configuration olefin bridge, the proline rings are stabilized in the presumed biologically active conformation, and the central seven-membered ring ensures perfect fixing of the trans amide bond.

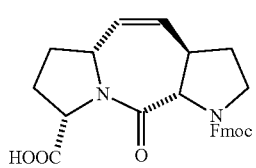

85

To provide this compound in substantial quantities, a practical, stereoselective synthetic pathway had to be developed. To this end, a strategy was chosen wherein the target molecule is convergently broken down to two vinylprolines of the type 100 and 101 (retrosynthetic decomposition of the central seven-membered ring, see Scheme 20). Initially, the vinyl-prolines would be linked via peptide coupling, followed by closing the tricyclic moiety via olefin metathesis. Ring closure metatheses to form seven-membered rings are well-known in the literature. Each of the two differently substituted vinyl proline derivatives 100 and 101 would have to be synthesized in a stereoselective manner. In either case, L-pyroglutamic acid could be used as starting material.

Scheme 20

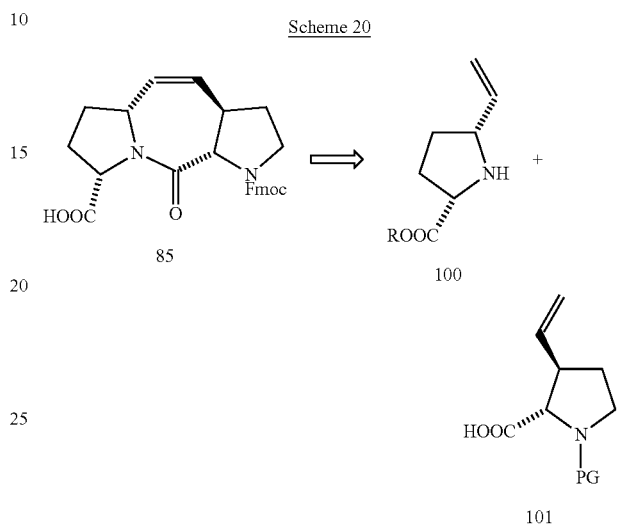

The trans-3-vinylproline 166 with an N-Boc protecting group was used as type 101 component, and the synthesis thereof was initiated by converting L-pyroglutamic acid 133 into building block 136 (Scheme 31).

Scheme 31: Synthesis of building block 136 from L-pyroglutamic acid

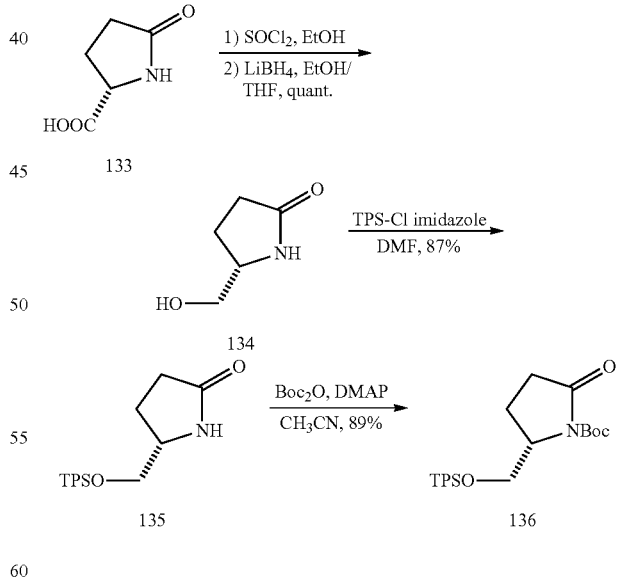

To this end, the acid 133 was initially converted into the ethyl ester, and the reduction thereof with lithium borohydride furnished the highly polar alcohol 134 in quantitative yield. The latter was protected with the stable and sterically demanding tert-butyldiphenylsilyl group (TPS) (87%) intended to largely shield the "underside" of the molecule during the following introduction of the new substituent so as to favor formation of the desired trans configuration. Thereafter, the nitrogen atom in 135 was provided with a Boc protection group (89%), in which case only a catalytic amount of DMAP rather than further stoichiometric addition of base was required according to a modified method. The stable and well-crystallizable intermediate 136 thus produced on a multigram scale was used as a starting basis for the further synthesis of the trans-3-vinylproline 166, using the synthetic concept of Herdeis et al. In accordance with the literature protocol, 136 was deprotonated at the α-position relative to the carbonyl group using the sterically hindered base LiHMDS at −78° C. and converted into the selenyl ether by reacting with phenylselenyl chloride, and the ether was oxidized during work-up of the crude product at −78° C. with hydrogen peroxide (30%) or ozone to form the selenium oxide which should form the enone 18 by elimination upon heating to room temperature (Scheme 41).

Scheme 41: Synthesis of the α,β-unsaturated lactam 18.

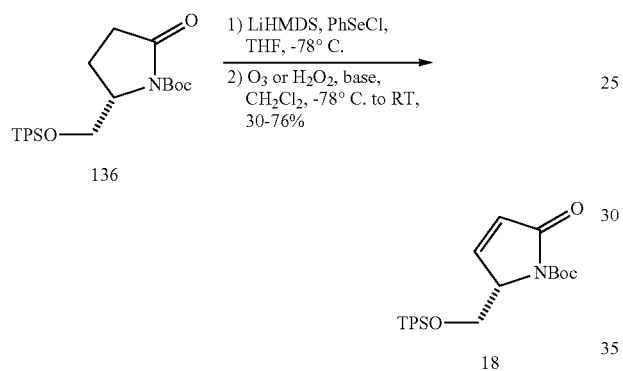

However, despite precise observance of the literature conditions, there were problems in reproducing the results: on the one hand, the yields were not constant and sometimes unsatisfactorily low and, on the other hand, the enone 18 was not obtained in purity grade. (Similarly, the yields achieved in the literature vary strongly, i.e. from 54 to 86% for the same substrate, which can be interpreted as indicative of practical problems.)

Scheme 42: Preparation of the enone 18 with isolation of the intermediate 160.

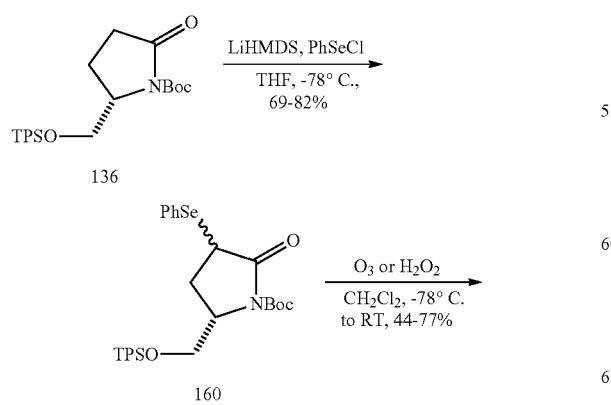

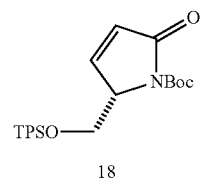

Extensive test experiments were carried out to investigate the matter in detail. To this end, the selenated intermediate 160 was initially isolated and purified by chromatography to remove residues of educt 136 (difficult to remove after elimination) and phenylselenyl chloride (likewise consumes oxidant) (Scheme 42). The yields of resulting intermediate 160 were comparable with the results in the literature (69-82%).

Smooth and quantitative elimination to form the enone 18 was found more problematic so that various possible parameters (solvent, temperature, base, oxidant) were varied. The use of different solvents (ethyl acetate, anhydrous or non-anhydrous dichloromethane) or varying temperatures (−78° C., −10° C., 0° C., differently rapid heating to room temperature or 70° C.) failed to result in a significant change. Above all, the influence of oxidant ($H_2O_2$ at concentrations of 10 to 30%, ozone, MCPBA, sodium periodate, each in varying equivalents) and base (pyridine, sodium acetate, varying equivalents or no addition of base) was tested. The results can be summarized as follows:

Ozone or $H_2O_2$ (25-30%) were found equally suitable as oxidants, and MCPBA could also be used, whereas sodium periodate was not strong enough. However, despite the apparently smooth reaction in the thin-layer chromatogram, some of the isolated yields were considerably lower, and a final clarification of what had happened to the remaining substance was not possible (excess oxidation? decomposition?).

As became apparent, addition of base (as usual in the literature) to slightly increase the yield can be advantageous, but this also favors formation of an isomerization product in varying amounts, the structure of which presumably can be represented as pyrrole derivative 161 (Scheme 43, see also analytical data in Section 7.2.3.18). Similarly, basic work-up of the reaction mixture resulted in increased formation of 161.

Scheme 43: Formation of side product 161 by addition of base in the elimination to form 18.

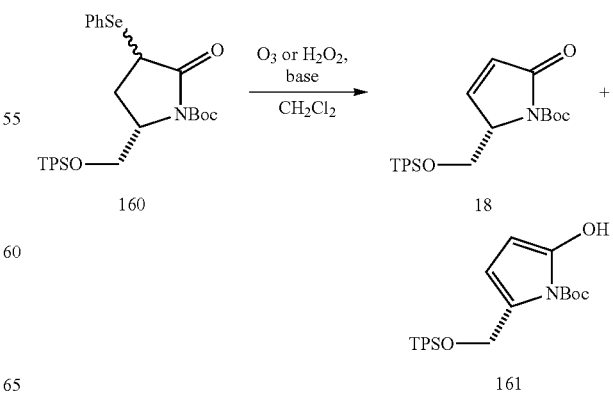

Scheme 44: Addition of vinyl cuprates to the enone 18.

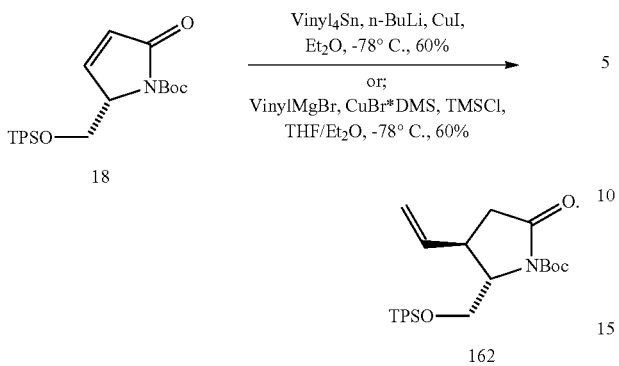

Subsequently, the vinyl group was introduced in the obtained enone 18 by means of 1,4-addition, initially using Gilman cuprates of the type $R_2CuLi$ (Scheme 44). The vinyllithium required for this purpose was obtained from tetravinyltin and n-butyllithium via transmetallation at 0° C. Without isolation, conversion into the divinyl cuprate was effected by adding copper(I) iodide at –20° C., which can be seen by the black coloration of the suspension, followed by addition to the enone by adding a solution of 18 in diethyl ether at –78° C. The addition product 162 was obtained in a yield of 60%, which is in the range of the literature data. Furthermore, and in accordance with the literature, only one diastereomer of the vinyl addition product was found. There was formation of a byproduct to some extent, which had formed as a result of incomplete transmetallation and resulting addition of an n-butyl residue to 18.

To circumvent the use of toxic and expensive tetravinyltin, a Normant cuprate of the type $R_2CuMgBrDMS$ was subsequently used which is readily obtainable by reacting a Grignard compound with CuBrDMS and afforded the 1,4-addition product 162 in comparable yield (60%) but somewhat lower purity.

Scheme 46: Alternative two-step reduction of the carbonyl group.

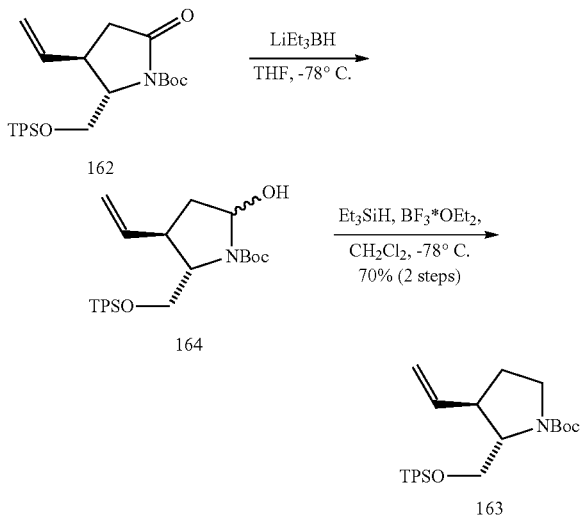

To remove the lactam carbonyl group, a two-step reduction sequence seemed to be appropriate (Scheme 46). Initially, the N-acyllactam 162 was reduced with superhydride to form the α-hydroxycarbamate 164 which subsequently was deoxygenated with triethylsilane (or, alternatively, triphenylsilane) and boron trifluoride to form the secondary, still Boc-protected amine 163 (70%, two steps).

Scheme 47: Completion of the synthesis of the trans-3-vinylproline 166.

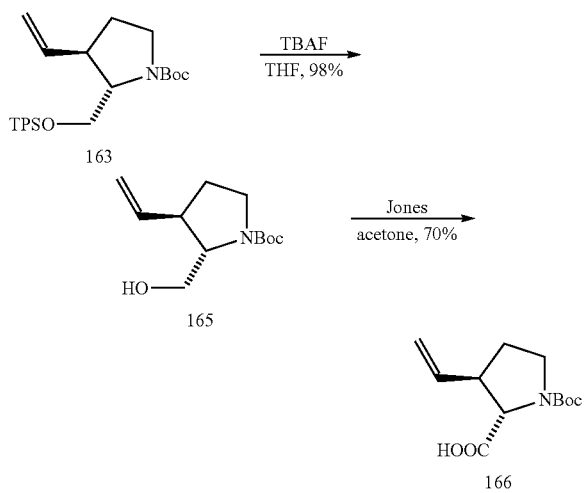

Thereafter, the silyl ether was cleaved with TBAF in THF (98%) and the resulting alcohol 165 was oxidized to form the carboxylic acid (Scheme 47). Here, the conditions of Herdeis et al. were not applicable either, because the vinyl group is not compatible with the conditions of a Sharpless oxidation ($NaIO_4/RuCl_3$). When using the Jones reagent, oxidation to form the carboxylic acid was possible with 70% yield, so that the synthesis of the N-Boc-trans-3-vinylproline 166 was completed. The correct constitution and relative configuration (trans) were confirmed by means of X-ray crystallographic analysis.

FIG. 1 shows the crystal structure of the N-Boc-protected trans-3-vinylproline 166.

To synthesize the second building block, which is a cis-5-vinylproline ester of the type 100, the route of Mulzer and Schülzchen was chosen, but initially using the commercially available L-pyroglutamic acid ethyl ester. The latter was provided with a Boc protecting group, and the protected substrate 167 (Scheme 48) was selectively reduced with DIBAL-H at low temperature to form the α-hydroxycarbamate. No reduction of the ester occurs when slowly adding the reducing agent at low temperature because the carbonyl group of the N-acyllactam reacts preferentially. Following neutral work-up with potassium-sodium tartrate solution, the resulting crude product was converted into the α-methoxycarbamate 168 (mixture of epimers, 90%, two steps), using a catalytic amount of PPTS in methanol.

Scheme 48: Synthesis of the N-Boc-protected 5-vinylproline ethyl ester (mainly cis).

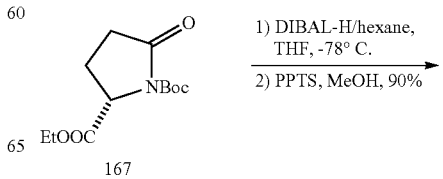

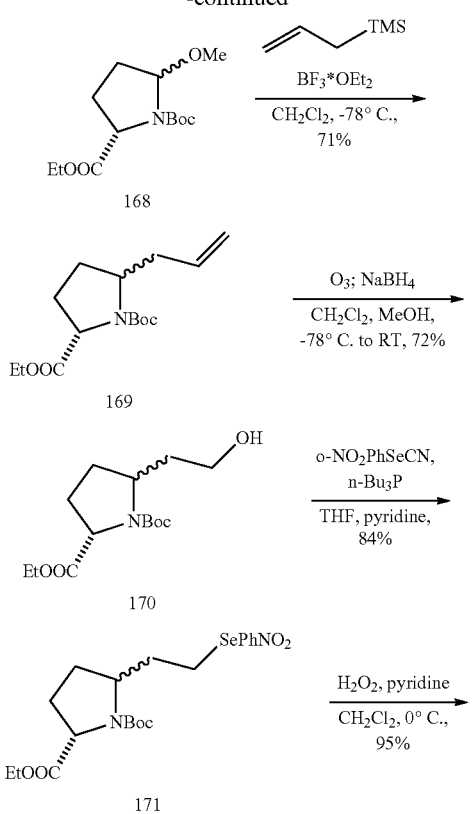

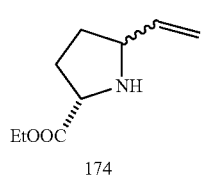

To introduce the second substituent, 168 was reacted with boron trifluoride and allyltrimethylsilane, thus obtaining the allyl substitution product 169 in the form of an unresolvable mixture of diastereomers (cis/trans=4:1, 71% in total). The double bond of 169 was subsequently cleaved by ozonolysis, and the resulting ozonide was reduced with sodium borohydride to form the alcohol 170, where no reduction of the ethyl ester was observed or only in trace amounts (72%). To convert into the olefin 172, the alcohol 170 was reacted according to Grieco et al., using ortho-nitrophenyl selenocyanate and tri-n-butylphosphine, thereby initially obtaining the selenyl ether 171 (84%). Oxidation with $H_2O_2$ (30%) at 0° C. and subsequent elimination afforded the vinylproline 172 in the form of a mixture of diastereomers (95%).

Removal of the Boc protecting group (Scheme 49) was effected by treatment with trifluoroacetic acid (quantitative) or TMSOTf (69%). Following hydrolysis, this resulted in the chromatographable free amine 174 which was obtained in a pure form, but still presented itself as an unresolvable mixture of diastereomers (amount of cis product: 80%).

Using the material thus obtained, further synthesis of the tricyclic diproline mimetics was developed (peptide coupling and subsequent ring closure metathesis). Despite steric hindrance as a result of the two vinyl groups, it was possible to generate the peptide bond under standard conditions in good yield (Scheme 52). To this end, the carboxylic acid 166 was pre-activated with EDAC/HOBt prior to adding the amine 173 and triethylamine as base. The identity of the coupled product was confirmed in a $^1$H-NMR spectrum despite the presence of a mixture of diastereomers and rotamers.

Scheme 52: Peptide coupling of the vinylproline under standard conditions.

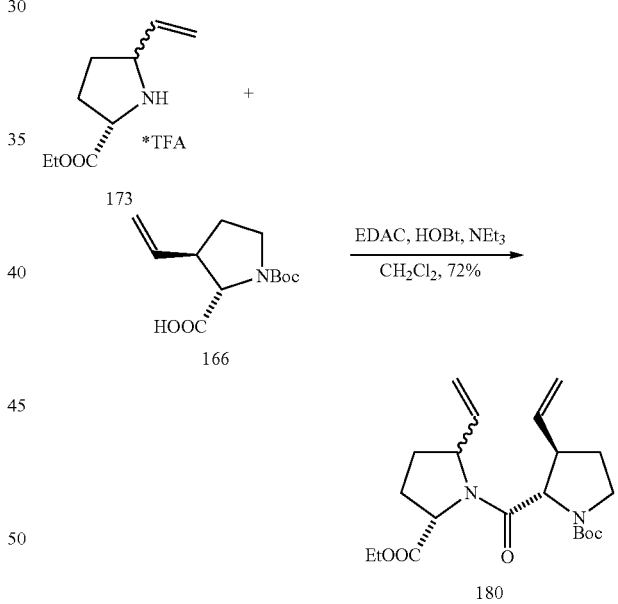

Scheme 49: Synthesis of the cis-5-vinylproline (mixture of diastereomers).

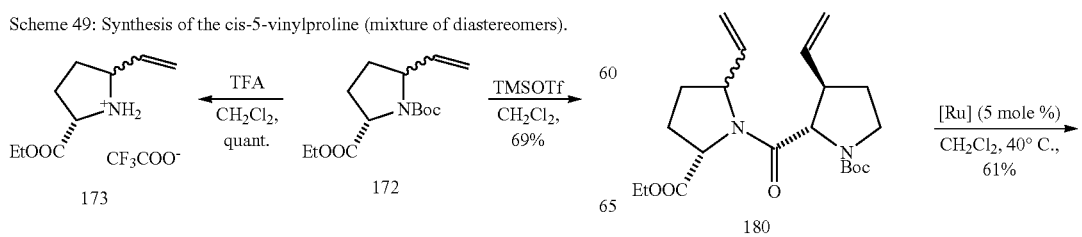

Scheme 53: Ring closure metathesis to form the tricyclic product 181.

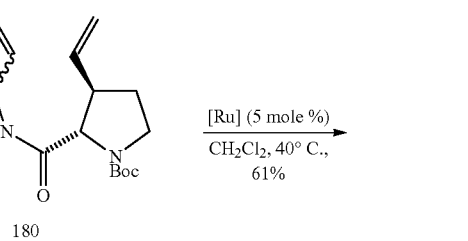

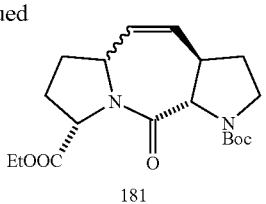

181

To produce the tricyclic 181 by ring closure metathesis, the dipeptide 180 was initially added with Grubbs II catalyst (Scheme 53) (5 mole %), but the conversion was incomplete so that the active and air-stable metathesis catalyst 82 from Blechert et al. was used (for a simple synthesis thereof from Grubbs II catalyst see Scheme 54). Using the latter, the reaction finally proceeded to completeness according to thin-layer chromatogram (isolated yield: 61% on a 10 mg scale). The success of ring closure metathesis was clearly confirmed based on the change of the olefin signals in the $^1$H-NMR spectrum.

Scheme 54: Synthesis of the modified methathesis catalyst 82 according to Blechert et al.

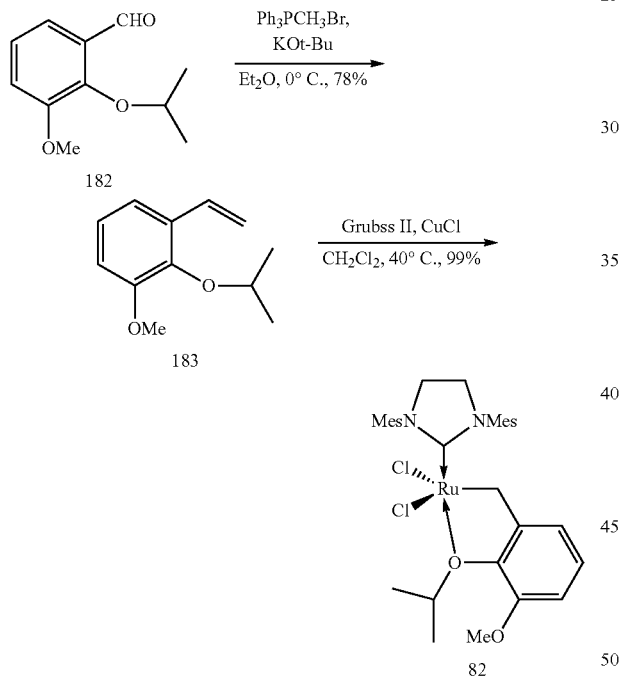

reduction of 44 with DIBAL-H to form the α-hydroxycarbamate and subsequent conversion into the corresponding α-ethoxycarbamate 45 (89%, 2 steps).

Scheme 55: Synthesis of the N-Boc-5-vinylproline tert-butyl ester 185.

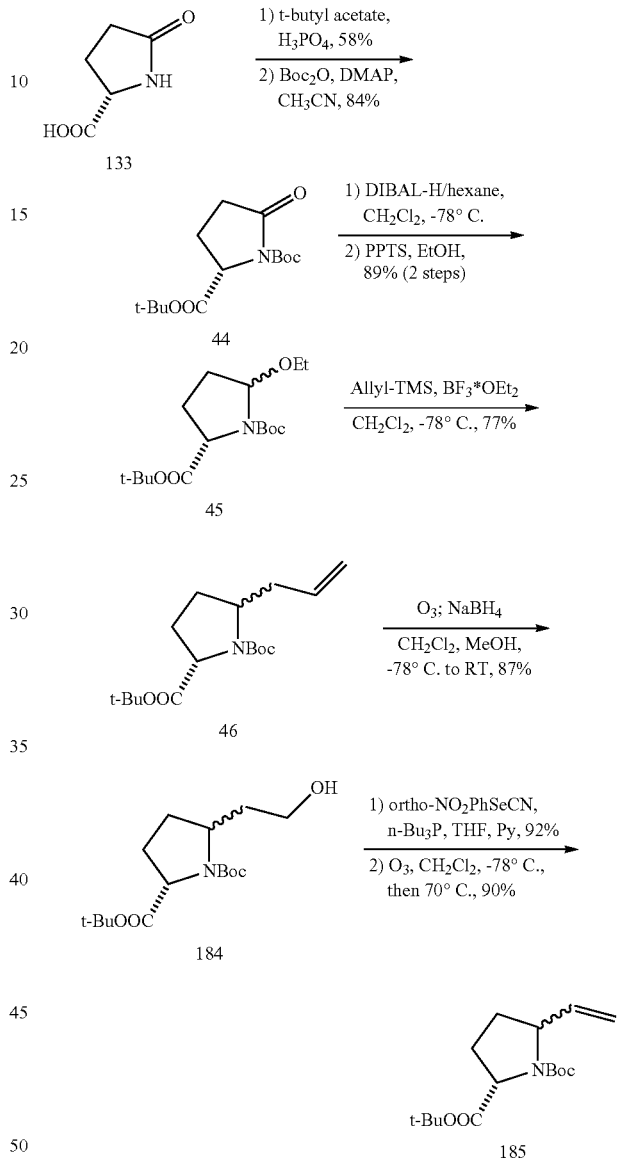

Having achieved successful preparation of the tricyclic product 181 it appeared convenient to synthesize the peptide mimetic 85 with diastereomerically pure components. Separation of the cis/trans isomers of the allyl substitution product according to Mulzer/Schülzchen is possible with the tert-butyl ester 46 by using preparative HPLC, but this option had to be ruled out in the present case for practical reasons. However, separation of 46 by column chromatography after removal of the Boc protecting group has also been described.

Therefore, a synthesis of the tert-butyl ester building block 185 was carried out. To this end, the pyroglutamic acid 133 was converted into the tert-butyl ester (58%) with tert-butyl acetate, using re-esterification under phosphoric acid (60%) catalysis, which ester was provided with a Boc protecting group (84%, Scheme 55). As before, this was followed by As expected, substitution of 45 with allyltrimethylsilane/boron trifluoride resulted in a diastereomeric mixture of the allyl substitution product 46 (77%, cis/trans 75:25) which could not be resolved by column chromatography. Removal of the N-protecting group at this point was not attempted because resolution on a multigram scale would have been complex and the sequence of deprotection—resolution of diastereomers—protection would have involved a detour. Instead, resolution of the diastereomers at the stage of the vinylproline ester 185 was favored because the N-protecting group had to be removed for peptide coupling anyway.

Ozonolysis of 46 and reduction with NaBH$_4$ to form the alcohol 184 (87%) was followed by reaction to form the corresponding selenyl ether which was oxidized with ozone at −78° C., followed by selenium oxide elimination at 70° C.

to furnish the 5-vinylproline tert-butyl ester 185 (92%). It was found that the intensely yellow-colored selenium-containing byproducts were difficult to remove. Despite multiple chromatography using different combinations of eluents, complete removal was not possible, and no colorless product was obtained. However, no significant contamination with nitrophenylselenium species was seen in the $^1$H-NMR spectrum of 185 (i.e. purity>95%). In fact, the remaining intensely yellow impurities could be removed in the next step.

To remove the Boc protecting group, while retaining the likewise acid-labile tert-butyl ester, a differentiation of both protecting groups was required, to which end e.g. TMSOTf, TBSOTf or TMSClO$_4$ have been described in the literature. (Conversely, saponification of esters while retaining the Boc group is also possible, to which end e.g. KOSiMe$_3$ can be used.)

Scheme 56: Preparation of diastereomerically pure cis-5-vinylproline tert-butyl ester 186a.

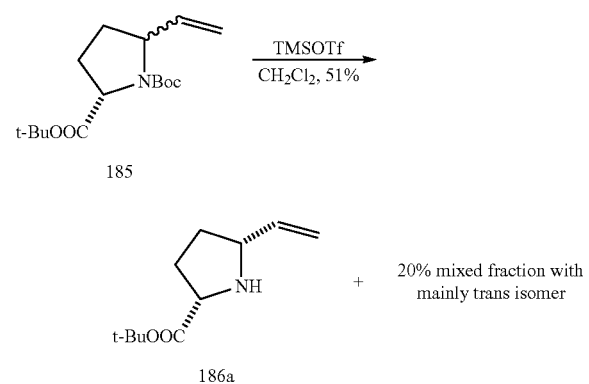

Slow addition of a solution of 185 with an equimolar amount of TMSOTf (1.01 equivalents) resulted in the desired nitrogen deprotection, while retaining the ester function (Scheme 56). Thereafter, the two diastereomers were sufficiently different to allow resolution thereof by careful chromatography, thus obtaining the cis-5-vinylproline ester 186a as a slightly yellowish oil (51%). The relative stereochemistry of the two substituents was confirmed by NOE experiments. The compound underwent gradual epimerization so that the product was immediately reacted further or stored frozen in a benzene matrix.

To synthesize the conformationally fixed diproline peptide mimetic 85, peptide coupling of the diastereomerically pure vinylprolines 166 and 186a under EDAC/HOBt conditions was attempted which, however, furnished only a low yield of the desired product 187 (38%) and a substantial amount of byproduct (24%), the NMR spectra of which could be assigned to an epimerized compound. As described in a different context, the use of triethylamine as base may give rise to epimerization of particular stereocenters, so that it was replaced with DIPEA in the present case. In addition, the more reactive PyBOP was employed as coupling reagent so that preactivation of the carboxylic acid was no longer required. In this way, yields of dipeptide 187 of 81% were achieved, and formation of the epimerization product (although easy to remove) was suppressed (Scheme 57).

Scheme 57: Completion of the synthesis of diastereomerically pure diproline 188.

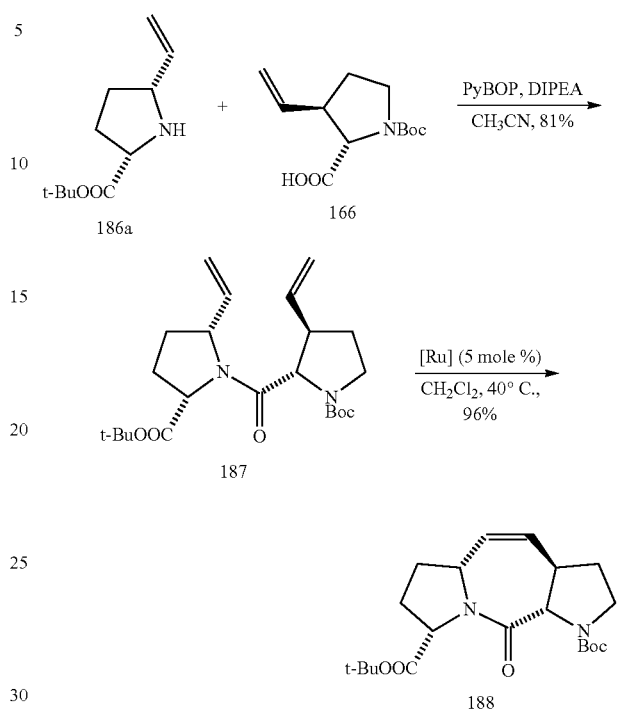

Two different catalysts were tested in the ring closure metathesis to form the tricyclic product 188: the air-stable catalyst 82 according to Blechert et al. and the Grubbs II catalyst 81. Both of these achieved comparable results. Complete conversion of the educt 187 required about 5 mole % of the respective catalyst when reacting overnight (40° C.). Following work-up of the reaction, taking care that any residues of catalyst were removed completely, if possible, high yields of up to 96% were achieved.

Finally, both protecting groups had to be removed and the amine function provided with a Fmoc protecting group so as to make the synthesized tricyclic product 188 useful in a solid-phase peptide synthesis. This is the only N-protecting group of practical significance that can be removed under mild basic conditions, to which end secondary amines such as piperidine, morpholine etc. are normally used. In this way it is possible to generate the unprotected amino function in a solid-phase synthesis without additional production of salts. Increased base instability hampers the use of the Fmoc group in organic synthesis and therefore requires changing the protecting group at a late stage.

Scheme 59: Reprotection of diproline 188 to form the peptide mimetic 85.

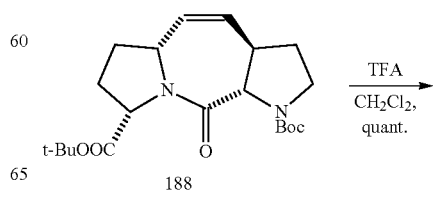

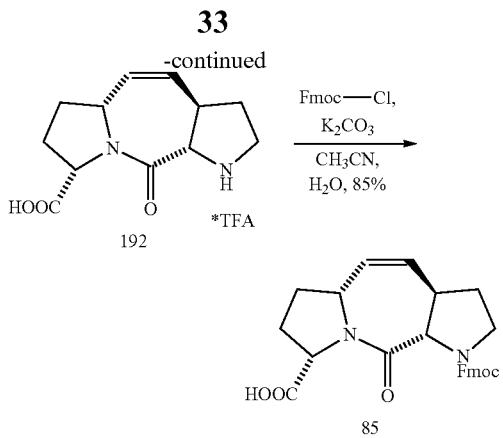

For simultaneous acidic removal of the Boc protecting group and tert-butyl ester, 188 was added with excess trifluoroacetic acid (99%) in dichloromethane and stirred at room temperature (Scheme 59). Concentrating furnished the free amino acid 192 in the form of a yellowish solid (control NMR spectrum in $D_2O$) which was dissolved in an acetonitrile/water mixture and converted into the Fmoc-protected final product 85 under Schotten-Baumann conditions. The product was found to be markedly polar, but nevertheless could be extracted with chloroform from the aqueous phase at pH 4 and subsequently purified by silica gel column chromatography. 85 was obtained in the form of an amorphous off-white solid (85%), the NMR spectrum of which was as expected (see FIG. 2 for 500 MHz $^1$H-NMR spectrum (MeOH-$d^4$), 60:40 mixture of rotamers).

Figure 2:
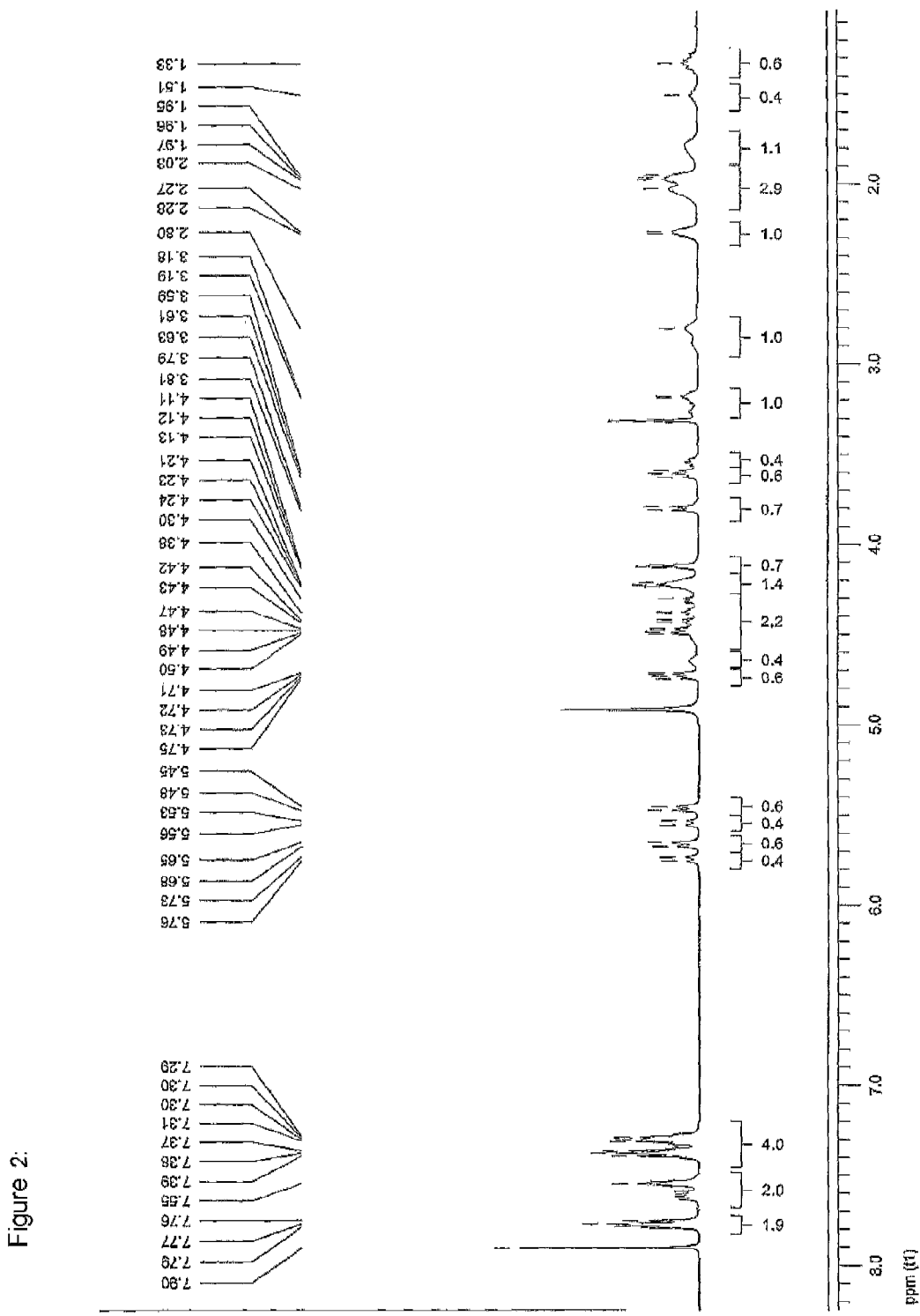
FIG. 2 shows the $^1$H-NMR spectrum of the diproline building block 85 (500 MHz, MeOH-d$^4$, RT).

FIG. 2 shows the $^1$H-NMR spectrum of the diproline building block 85 (500 MHz, MeOH-$d^4$, RT).

Biological Results

A total of about 300 mg of conformationally fixed diproline 85 was synthesized and handed over to the FMP in Berlin-Buch for incorporation in test ligand peptides and biological binding studies. Based on the sequence $_{332}$SFEFPPPPT-EDEL$_{344}$ of the ActA peptide from *Listeria monocytogenes*, which is known to be a strongly binding, native ligand peptide of the EVH1 domain, two test peptides were synthesized up to the end of the present work and investigated for their binding affinity to the VASP/EVH1 receptor, namely, $_{332}$SFEFPppPT-EDEL$_{334}$ (I) and $_{332}$SFEWPppPTEDEL$_{344}$ (II) wherein pp represents the synthetic diproline building block 85. Earlier substitution experiments have shown that replacing phenylalanine (P) with tryptophan (W) results in a significantly higher binding affinity with the VASP/EVH1 domain: $K_D$=13.7 µM for the ligand peptide including the WPPPP core compared to $K_D$=55.1 µM for the ligand including the FPPPP core motif.

Figure 3:
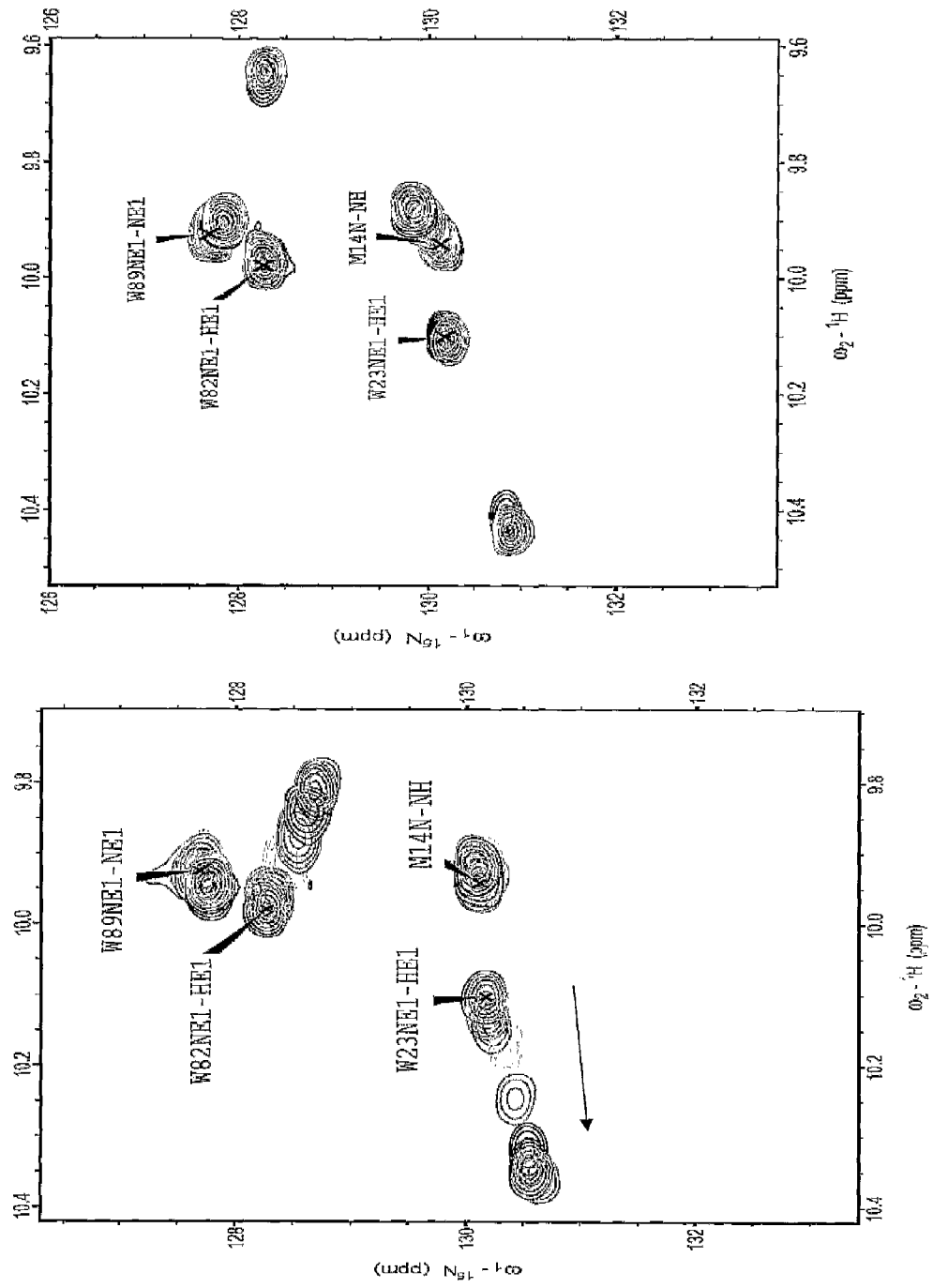
FIG. 3 shows overlay series of two-dimensional $^{15}$N-$^1$H-HSQC-NMR spectra of the VASP/EVH1 domain (600 MHz) under the influence of varying concentrations of ligand peptide I (left) and II (right).

FIG. 3 shows overlay series of two-dimensional $^{15}$N-$^1$H-HSQC-NMR spectra of the VASP/EVH1 domain (600 MHz) under the influence of varying concentrations of ligand peptide I (left) and II (right) as well as a detail representation of cross-peaks between protons and nitrogens of some aromatic side chains, wherein the shift of W23NE1-HE1 with increasing concentration of the ligand peptide I (in direction of the arrow) is particularly illustrative.

The interactions between the EVH1 domain of a completely $^{15}$N-labelled VASP protein and the ligand peptides I and II was elucidated using multidimensional NMR-spectroscopic methods. To this end, the EVH1 domain in a solution was titrated with varying amounts of ligand peptide and investigated by recording $^{15}$N-$^1$H-HSQC-NMR spectra each time. In the event of positive binding interaction, increasing the ligand concentration step by step (10, 20, 50, 100, 200, 500 and 1000 µM) results in a clearly recognizable shift of some domain signals, which can be used to calculate values for the binding constant at a later point in time. The result of the investigations including the ligand peptides I and II can be inferred from the superimposed details of the respective HSQC spectra in FIG. 3. It is especially aromatic amino acid residues of the domain that are involved in the development of the hydrophobic binding interactions ("aromatic groove", cf. Sections 2.4/2.5), so that the shift of the signals can be clearly recognized. In particular, this applies to the NH signal of tryptophan 23 (W23NE1-HE1), as it forms a hydrogen bridge to a carbonyl group of the FPPPP ligand motif.

However, a comparison of the two NMR spectra in FIG. 3 shows that the situation described above is observed only with ligand I (left). A continuous equilibrium, i.e. [EVH1]-ligand (bound)↔[EVH1]+ligand (unbound), is present in solution so that, depending on the rate of interchange of the ligands, different NMR spectra are obtained (in analogy to the signals of —OH and —NH in the one-dimensional range). For ligand I, time-averaged signals from both states are observed, while for ligand II, both states generate separate sets of signals on an NMR time scale. This can be seen particularly clearly by comparing the two NMR spectra with reference to the W23NE1-HEI signal: for ligand I (left), there is a gradual shift of the cross-peak during titration; for ligand II (right), two separate signals that undergo only minor changes, but no "intermediate states" are observed.

When correlating the changes in the chemical shift of the cross-peaks with the binding strength between domain and ligand peptide, it is possible to calculate values for the binding constant by plotting the change in shift Δδ versus the ligand peptide concentration. This was done for I (FIG. 4) and resulted in a somewhat higher binding affinity ($K_D$=20-35 µM) compared to the native peptide sequence ActA ($K_D$=45 µM). As for II, this was not possible due to the situation discussed above.

Figure 4:
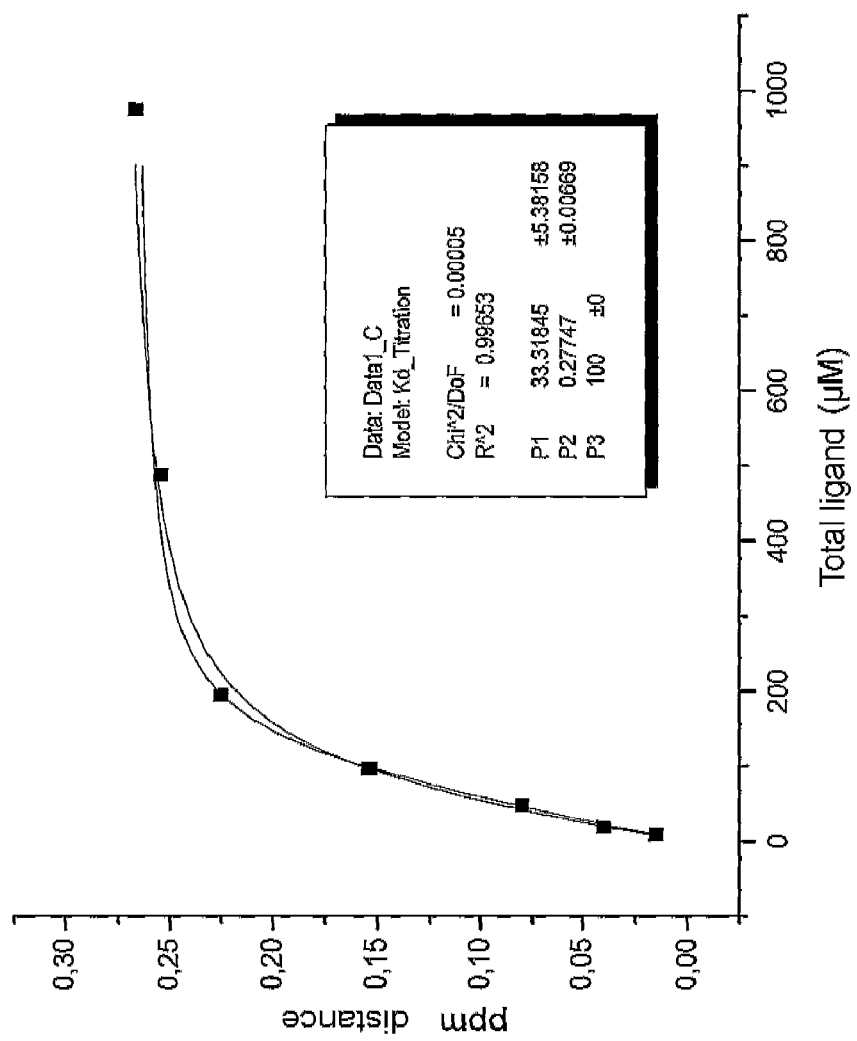
FIG. 4 shows a plot of the change in chemical shift $\Delta\delta$ versus the concentration of ligand peptide I to determine the binding constant $K_D$.

FIG. 4 shows a plot of the change in chemical shift Δδ versus the concentration of ligand peptide I to determine the binding constant $K_D$.

As a supplement to NMR-based elucidation of interactions between peptides and proteins, the Biacore method is also employed as a standard today. In this method the domain protein is immobilized on the surface of a sensor chip, while a solution of ligand peptide flows across the surface. By measuring the surface plasmon resonance that causes the refractive index to change, it is possible to monitor the binding kinetics in real-time so that the association and dissociation constants can also be determined. Especially in those cases where NMR spectroscopy fails to determine a binding constant, as is the case with the ligand peptide II, this is the method of choice. Initial measurements—yet remaining to be verified—furnished the following binding constants: $K_D$=29.3-33.3 µM for ligand peptide I and $K_D$=3.7-12.5 µM for ligand peptide II (the corresponding native peptides: $K_D$=55.1 µM and $K_D$=13.7 µM, respectively).

Specifically, these results are remarkable in that experiments are concerned which have not been described for the EVH1 domain as yet and lead to a number of important findings which can be summarized as follows and form the basis of future research:

1) Incorporation of the synthetically produced tricyclic 85 in different test peptides under standard coupling conditions (DIC/HOBt) of a solid phase peptide synthesis proceeded without problems.

2) Previous predictions stating that the two central proline positions of the F/WPPPP core motif should be replaceable were confirmed.
3) The prediction of a reactive conformation when binding the PPII helix to the EVH1 receptor was confirmed by the good binding affinity of the ligand peptide I, and/or the biologically required conformation and the actual conformation of the tricyclic product 85 were in good agreement.
4) The expected favorable entropy effect as a result of local conformational prefixing of the ligand appears to be confirmed by the ascertained higher binding affinity compared to the native peptide sequence. On the other hand, geometric fixing prevents the approach of ligand and domain protein and thus formation of a bond.

Figure 5:
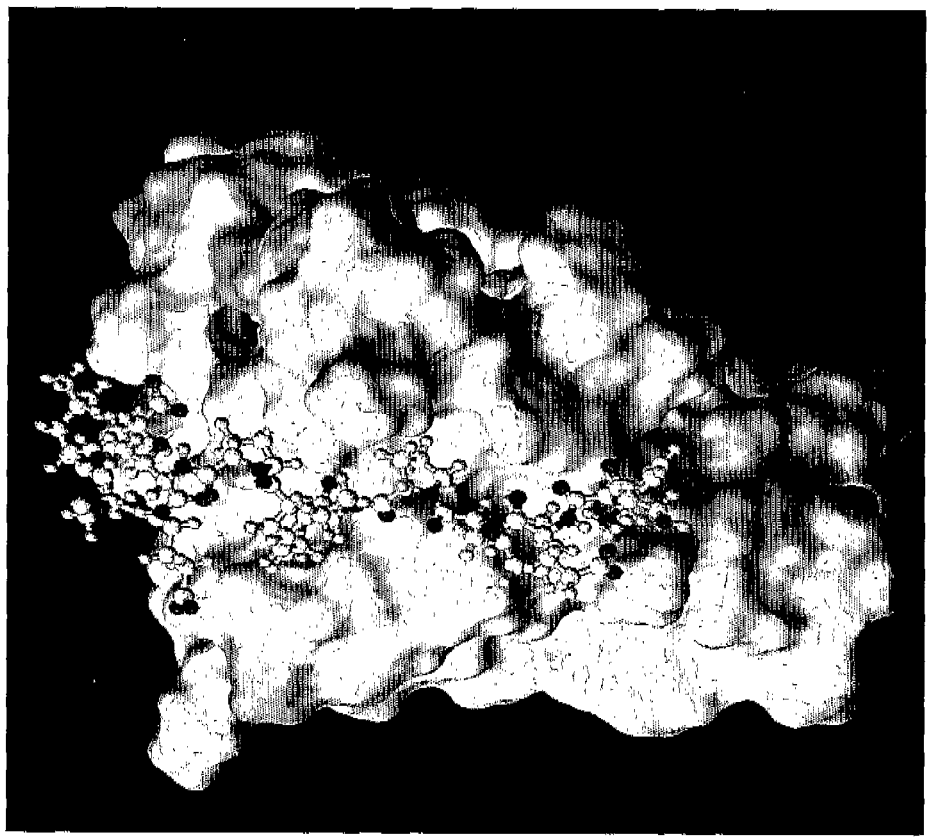
FIG. 5 shows a representation of the VASP/EVH1 domain with the $_{332}$SFEFPppPTEDEL$_{344}$ peptide ligand (molecular modeling representation).

FIG. 5 shows a representation of the VASP/EVH1 domain with the $_{332}$SFEFPppPTEDEL$_{344}$ peptide ligand (molecular modeling representation). The EVH1 domain can be clearly recognized as a "groove" on the surface of the VASP protein, which receives the ligand peptide.

Biological Results and Conclusion

Using the synthetic compound 85, ligand peptides with partially or completely replaced proline sequences were synthesized and investigated for their interaction with the EVH1 domain (pp=building block 85). Incorporation of the mimetic 85 was found to increase the binding affinity of the ligand peptide to the domain. Replacement of all prolines with 2 linked building blocks 85 resulted in ligand peptides with an affinity comparable to that of the native peptide. This is summarized in Table 1 below wherein the binding affinities of the ligand peptides and the basic native peptide ligands are listed. The binding affinities were determined using NMR titration, the kinetic Biacore method, or by means of fluorescence titration. The results are summarized in Table 1.

TABLE 1

Comparison of measured binding affinities (interaction of ligand peptides with the VASP/EVH1 domain in solution).

| Ligand peptide | Binding affinity (NMR) | Binding affinity (Biacore) | Fluorescence titration |
|---|---|---|---|
| SFEFPPPPTEDEL | 45 µM | 55.1 µM | 37 ± 10 µM |
| SFEFPppPTEDEL (I) | 20-35 µM | 29.3-33.3 µM | 47 ± 14 µM |
| SFEFppPPTEDEL | — | — | 82 ± 30 µM |
| SFEFPPppTEDEL | — | — | 26 ± 5 µM |
| SFEFppppTEDEL | — | — | 45 ± 15 µM |
| SFEWPPPPTEDEL | not measurable | 13.7 µM | — |
| SFEWPppPTEDEL (II) | not measurable | 3.7-12.5 µM | — |

Replacement of all prolines with 2 linked building blocks 85 resulted in ligand peptides with an affinity comparable to that of the native peptide. Thus, development of ligand peptides without proline-rich sequences that are bound by PRM-binding domains has been successful for the first time. The successful implementation of the general concept regarding the synthesis and biological use of target structure 85 presents—as a promising basis—a number of further options of addressing relevant protein domains by means of small synthetic molecules, which domains bind polyproline-containing ligands. In addition to varying existing molecular structures, it would also be conceivable to expand this concept to the synthesis of ligands for other domains (Mena-EVH1, WW, SH3 etc.), replacement of proline units other than the two central units in the FPPPP motif, or replacement of PPP or even PPPP motifs with suitable structures produced by organic synthesis.

EXPERIMENTAL SECTION

All reactions with air- or water-sensitive components were carried out under anhydrous conditions. To this end, the glassware to be used was annealed with a Bunsen burner flame under oil pump vacuum (final pressure 0.1-0.5 mbar) and flooded with argon after cooling, using a vacuum-argon double-stopcock glass apparatus. Syringes and cannulas used to transfer reagents and solvents were dried in an oven at 85° C. and repeatedly purged with argon prior to use. Filling solid reagents in reaction flasks was done in an argon countercurrent. Solvents were removed in a rotary evaporator at a water bath temperature of 40° C. and a pressure of 10-1013 mbar. Further drying of substances was effected under oil pump vacuum (0.1-0.5 mbar), normally at room temperature. The chemicals used were commercially purchased from well-known companies such as Merck, Sigma-Aldrich, Fluka, Acros, Lancaster and Strem and usually employed without further purification. The concentration of organometallic reagents was determined according to Paquette et al. by titration versus menthol with phenanthroline as indicator. All solvents used in extraction and purification procedures were distilled prior to use. Anhydrous solvents were obtained according to appropriate methods.

Purification of substances was effected using flash column chromatography over silica gel (Kieselgel 60, 0.040-0.063 mm, Merck) under slight overpressure (0.3-0.5 bar). Analytical thin-layer chromatography (TLC) for reaction monitoring was performed using silica gel plates from Merck (Kieselgel 60F$_{254}$). Interpretation of the chromatograms was carried out under UV light ($\lambda$=254 nm) and by staining with a KMnO$_4$ solution (3 g of KMnO$_4$, 20 g of K$_2$CO$_3$, 5 ml of 5% NaOH, 300 ml of H$_2$O) and subsequent heating with a hairdryer. Analytical high-pressure liquid chromatography (HPLC) was performed using a Knauer system (HPLC Pump K-1001, DAD K-2700 Wellchrom, Lamp K-2701 Wellchrom, Solvent Organizer K-1500), a Merck-Hitachi system (L-4000 A UV detector, D-6200A Intelligent Pump, differential refractometer Ri71), a Merck-Hitachi system (L-7250A Intelligent Pump, L-7455 UV detector), or an Agilent 1100 HPLC-MS system. Further data can be found under the respective measurements.

$^1$H- and $^{13}$C-NMR spectra were recorded at room temperature using the instruments AC 250, DPX 300 and DRX 500 from Bruker. The chemical shifts are given relative to the residual proton content or the resonance of the solvent as internal standard. The signals were assigned by recording suitable 2D experiments (DEPT, APT, H-H COSY, HMQC, HMBC, NOE) and by comparison with analogous compounds. The Mestre C program with included analytical functions was used to interpret the NMR spectra. Numbering in the molecules for signal assignment is largely identical with IUPAC, but may deviate for clarity reasons. Signal multiplicities are given as follows: s=singlet, d=doublet, t=triplet, q=quartet, quint=quintet, br=broad signal, m=multiplet. Due to the hindered rotation of the carbamate protecting groups at room temperature, many compounds were observed as mixture of rotamers and will be described as such (broad peaks or double set of signals in the $^1$H- and $^{13}$C-NMR spectra).

IR spectra were recorded on an FT-IR Paragon 1000 from Perkin-Elmer as ATR (attenuated total reflectance) at room temperature on a ZnSe crystal to which the samples were applied in the form of a solution. The absorption bands are given in wave numbers ($\tilde{v}$ [cm$^{-1}$]) and characterized according to their relative intensity as follows: vs (very strong), s (strong), m (medium), w (weak), br (broad signal).

Mass determinations were performed on MAT Incos 50 Galaxy System (EI) and MAT 900 (ESI, HRMS) instruments from Finnigan. The inlet method (direct inlet probe (DIP) or GC-MS), type of ionization (EI or ESI) and ionization energy in eV are given in brackets. The represented signals relate to the ratio m/z and are given as intensities relative to the base peak (100%).

Optical rotation values were measured on a Polarimeter 343 plus from Perkin-Elmer. The concentration of [α] is given as [g/100 ml] unit, the measuring temperature, wavelength (normally 589 nm, sometimes 546, 405, 365 and 334 nm) and solvent are given each time.

Elemental analyses were performed using an Elementar Vario EL, and the mass percent composition was broken down according to the elements C, H and N. Melting points were determined using a B-545 from Büchi and are uncorrected.

The compounds were named using the Autonom program of the electronic Beilstein data base according to the IUPAC guidelines. Minor deviations from this nomenclature may occur when following the naming of substrates known in the literature or regarding functional groups more important as units (e.g. protecting groups), thereby creating different priorities. Determination of the stereochemistry was done according to the rules of Cahn-Ingold-Prelog. (lit.: R. S. Cahn, C. K. Ingold, V. Prelog, Angew. Chemie 1966, 78, 413)

(2S)-5-Oxopyrrolidine-2-carboxylic acid ethyl ester (203)

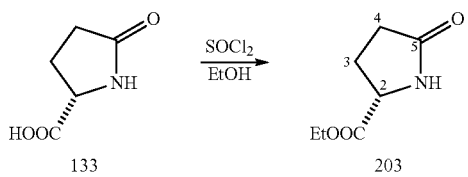

A suspension of 30.0 g of L-pyroglutamic acid 133 (232 mmol) in 100 ml of anhydrous ethanol was slowly added with 20 ml of SOCl$_2$ (274 mmol, 1.2 eq.) at 0° C. and subsequently stirred for 15 h, and the batch was thawed to room temperature to form a clear solution. For work-up, all volatile components were completely removed under vacuum, the remaining residue was subsequently taken up in 500 ml of ethyl acetate and successively stirred over K$_2$CO$_3$ and MgSO$_4$, each time removing the drying agent by suction. Filtration over a small amount of silica gel and solvent removal under vacuum afforded 36.0 g (230 mmol, 99%) of ester 203 in the form of a slightly yellowish, viscous oil.

M (C$_7$H$_{11}$NO$_3$)=157.1672.

R$_f$=0.47 (SiO$_2$, CH$_2$Cl$_2$/MeOH 9:1).

$^1$H-NMR (300 MHz, CDCl$_3$): δ (ppm)=7.04 (br, 1H, NH), 4.10-4.22 (m, 3H, H-2, ester CH$_2$), 2.22-2.48 (m, 3H, H-3$_\alpha$, H-4), 2.07-2.22 (m, 1H, H-3$_\beta$), 1.22 (t, 3H, J=7.1 Hz, ester CH$_3$).

$^{13}$C-NMR (75 MHz, CDCl$_3$): δ (ppm)=178.37 (lactam C=O), 172.10 (ester C=O), 61.58 (ester CH$_2$), 55.59 (CH), 29.33 (CH$_2$, C-4), 24.77 (CH$_2$, C-3), 14.11 (ester CH$_3$).

(5S)-5-Hydroxymethylpyrrolidin-2-one (134)

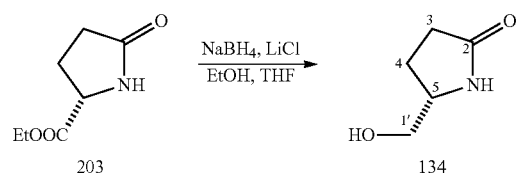

A solution of 36.0 g (230 mmol) of ester 203 in 400 ml of THF was added with 16.0 g of NaBH$_4$ (460 mmol, 2 eq.) and 19.5 g of LiCl (460 mmol, 2 eq.). This was subsequently added with 100 ml of EtOH, and the mixture was stirred overnight. Completion of the reaction was checked by means of TLC (CH$_2$Cl$_2$/MeOH 9:1) (optionally adding some milliliters of water, thereby significantly enhancing the reaction). Once the reaction was completed, 500 ml of 5% citric acid was added (evolution of hydrogen) to form a clear solution. After concentrating to dryness, the white, mucous residue was taken up in a 3:1 mixture of ethyl acetate/methanol and filtered over Celite. Any remaining precipitate was removed by concentrating, taking up the residue in 500 ml of CH$_2$Cl$_2$/MeOH (9:1) and subsequently filtering over silica gel.

After concentrating under vacuum, the crude product was dried under oil pump vacuum at 100° C. for several hours to obtain 25.6 g of pyroglutaminol 134 (169 mmol, 73%) as a colorless glassy solid.

M (C$_5$H$_9$NO$_2$)=115.1305.

R$_f$=0.18 (SiO$_2$, CH$_2$Cl$_2$/MeOH 9:1).

$^1$H-NMR (250 MHz, DMSO-d$^6$): δ (ppm)=7.66 (br, 1H, NH), 5.00 (t, 1H, J=5.4 Hz, OH), 3.50 (m, 1H, H-5), 3.28 (t, 2H, J=5.1 Hz, H-1'), 1.90-2.18 (m, 3H, CH$_2$), 1.69 (m, 1H, CH$_2$).

$^{13}$C-NMR (62.5 MHz, DMSO-d$^6$): δ (ppm)=176.64 (C=O), 64.40 (CH$_2$, C-1'), 55.16 (CH, C-5), 29.54 (CH$_2$, C-4), 22.73 (CH$_2$, C-3).

(5S)-5-(tert-Butyldiphenylsilanyloxymethyl)pyrrolidin-2-one (135)

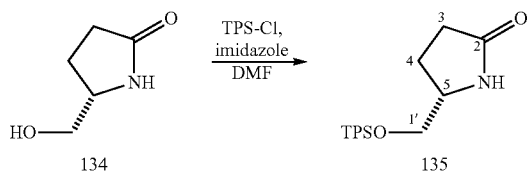

8.40 g of pyroglutaminol 134 (73 mmol) and 9.80 g of imidazole (144 mmol, 2 eq.) were dissolved in 100 ml of DMF (anhydrous) and cooled in an ice bath. This was subsequently added with 18.8 ml of TPS-Cl (73 mmol), and the mixture was stirred at RT overnight. For work-up, the batch was transferred into a separating funnel, diluted with 500 ml of MTBE and 100 ml of water, the phases were separated and the organic phase was dried over MgSO$_4$. Column chromatography (EE/CH 2:1) afforded 22.5 g of silyl ether 135 (64 mmol, 87%) as a colorless oil which gradually solidified to form fine white crystals.

M ($C_{21}H_{27}NO_2Si$)=353.5301.

$R_f$=0.19 ($SiO_2$, EE/CH 2:1).

m.p.: 75° C., lit.: 77-78° C.

$^1$H-NMR (300 MHz, $CDCl_3$): δ (ppm)=7.61-7.64 (m, 4H, PhH), 7.37-7.42 (m, 6H, PhH), 6.19 (br, 1H, NH), 3.78 (ddd, 1H, J=14.8 Hz, J=7.6 Hz, J=4.8 Hz, H-5), 3.60 (dd, 1H, J=10.3 Hz, J=4.2 Hz, H-1'$_α$), 3.51 (dd, 1H, J=10.3 Hz, J=7.2 Hz, H-1'$_β$), 2.27-2.33 (m, 2H, H-3), 2.04-2.20 (dt, 1H, J=12.9 Hz, J=7.8 Hz, H-4$_α$), 1.72 (dddd, 1H, J=13.0 Hz, J=9.1 Hz, J=7.4 Hz, J=5.3 Hz, H-4$_β$), H 4p), 1.03 (s, 9H, Sit-Bu).

$^{13}$C-NMR (75 MHz, $CDCl_3$): δ (ppm)=177.96 (C=O), 135.44, 135.40 ($CH_{ar}$), 132.90, 132.87 ($C_{ar,q}$), 129.81 ($CH_{ar}$), 127.75 ($CH_{ar}$), 67.29 ($CH_2$, C-1'), 55.57 (CH, C-5), 29.70 ($CH_2$, C-3), 26.71 ($CH_3$, Sit-BU), 22.73 ($CH_2$, C-4), 19.09 ($C_q$, Sit-Bu).

IR (ATR): $\tilde{v}$ ($cm^{-1}$)=3211 (br), 3069 (w), 2928 (m), 2855 (m), 1697 (vs), 1587 (w), 1471 (m), 1461 (m), 1426 (s), 1261 (w), 1111 (vs), 1029 (s), 867 (m), 822 (s), 740 (s), 701 (vs).

MS (DIP-EI, 70 eV): m/z (%)=352 ([$M^+$-H], <1), 296 (100), 252 (5), 218 (72), 199 (19), 181 (17), 162 (11), 135 (12), 105 (14), 84 (12), 77 (7), 55 (7).

$[α]_D^{20}$=+15.0° (c=1.245, $CHCl_3$). Lit.: +15.4° (c=0.825, $CHCl_3$).

(5S)-1-(tert-Butoxycarbonyl-5-(tert-butyldiphenylsilanyloxymethyl)pyrrolidin-2-one (136)

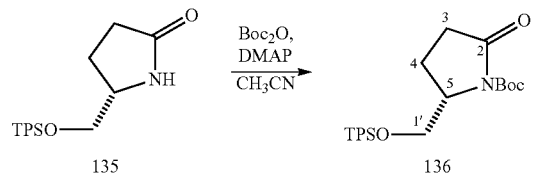

7.47 g of 135 (21.1 mmol) was dissolved in 100 ml of anhydrous acetonitrile, cooled to 0° C. and added with 100 mg of DMAP (0.81 mmol, 3.8 mole %) and 5.0 ml of $Boc_2O$ (23.4 mmol, 1.1 eq.). After stirring for 15 h at RT the, yellow-orange solution was concentrated to dryness, taken up in a mixture of cyclohexane/ethyl acetate (3:1) and filtered over a short silica gel column. Reconcentrating afforded a yellowish solid residue which was recrystallized from $Et_2O$/pentane, thereby obtaining 8.57 g of 136 (18.9 mmol, 89%) as colorless crystals.

M ($C_{26}H_{35}NO_4Si$)=453.6459

$R_f$=0.30 ($SiO_2$, EE/CH 1:3).

m.p.: 106-108° C. Lit.: 110° C.

$^1$H-NMR (500 MHz, $CDCl_3$): (mixture of rotamers) δ (ppm)=7.58-7.63 (m, 4H, $H_{ar}$r), 7.34-7.42 (m, 6H, $H_{ar}$r), 4.19 (tdd, 1H, J=8.2 Hz, J=4.1 Hz, J=2.2 Hz, H-5), 3.87 (dd, 1H, J=10.5 Hz, J=4.2 Hz, H-1'$_α$), 3.68 (dd, 1H, J=10.5 Hz, J=2.4 Hz, H-1'$_β$), 2.77 (td, 1H, J=17.6 Hz, J=10.4 Hz, H-3$_α$), 2.41 (ddd, 1H, J=17.6 Hz, J=9.2 Hz, J=2.8 Hz, H-3$_β$), 2.05-2.18 (m, 2H, H-4), 1.41 (s, 9H, Ot-Bu), 1.02 (s, 9H, SitBu).

$^{13}$C-NMR (125 MHz, $CDCl_3$): (mixture of rotamers) δ (ppm)=174.93 (lactam C=O), 149.72 (Boc C=O), 135.48, 135.44 ($CH_{ar}$), 132.99, 132.58 ($C_{q,ar}$), 129.82, 129.81 ($CH_{ar}$), 127.81, 127.77 ($CH_{ar}$), 82.62 ($C_q$, OtBu), 64.90 ($CH_2$, C-1'), 58.74 (CH, C-5), 32.26 ($CH_2$, C-3), 27.94 ($CH_3$, OtBu), 26.74 ($CH_3$, SitBu), 21.05 ($CH_2$, C-4), 19.12 ($C_q$, SitBu).

IR (ATR): $\tilde{v}$ ($cm^{-1}$)=3069 (w), 2957 (m), 2929 (m), 2856 (m), 1785 (s), 1747 (s), 1708 (s), 1588 (w), 1471 (m), 1426 (m), 1365 (s), 1308 (vs), 1286 (s), 1254 (s), 1150 (vs), 1106 (vs), 1076 (s), 1031 (s), 997 (m), 898 (m), 860 (m), 846 (m), 821 (s), 742 (vs), 700 (vs), 615 (s).

MS (DIP-EI, 70 eV): m/z (%)=438 ([$M^+$-$CH_3$], <1), 401 (<1), 380 (1), 340 (15), 296 (33), 218 (100), 199 (12), 181 (14), 162 (8), 135 (15), 105 (12), 84 (11), 57 (25).

$[α]_D^{20}$=−37.2° (c=0.995, $CHCl_3$). Lit.: −38.4° (c=1.30, $CHCl_3$).

(2R/S,5S)-1-(tert-Butoxycarbonyl)-5-(tert-butyl-diphenylsilanyloxymethyl)-2-hydroxypyrrolidine (204)

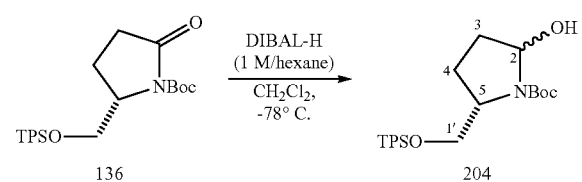

A solution of 3.00 g of 136 (6.61 mmol) in 15 ml of anhydrous $CH_2Cl_2$ was cooled to −78° C. in an annealed three-necked flask equipped with a dropping funnel and added dropwise with 12.5 ml of DIBAL-H (12.5 mmol, 2.2 eq., 1 M/hexane). After stirring for two hours at −78° C., the reaction was terminated by adding 1 ml of isopropanol, added with 20 ml of K—Na tartrate solution (1.77 M) and slowly thawed to room temperature. After separating the two phases, the aqueous phase was additionally extracted with 3×50 ml of MTBE, and the combined organic phases were dried over $MgSO_4$. After filtration over a short silica gel column (eluted with EE/CH 1:3), the filtrate was concentrated to obtain 204 as a slightly yellowish oil which was further reacted without purification. Yield: 2.92 g (6.41 mmol, 97%).

M ($C_{26}H_{37}NO_4Si$)=455.6618.

$R_f$=0.37 ($SiO_2$, EE/CH 1:3).

$^1$H-NMR (250 MHz, $CDCl_3$): (mixture of diastereomers/rotamers) δ (ppm)=7.57-7.70 (m, 4H, $H_{ar}$), 7.30-7.45 (m, 6H, $H_{ar}$), 5.46 (br, 1H, H-2), 3.20-4.05 (m, 4H, H-5, H-1', OH), 1.40-2.50 (m, 4H, H-3, H-4), 151.49, 1.32 (2 s, 9H, OtBu), 1.04 (s, 9H, SitBu).

$^{13}$C-NMR (62.5 MHz, $CDCl_3$): (mixture of diastereomers/rotamers) δ (ppm)=154.85, 154.55, 153.17 (Boc C=O), 135.43 ($CH_{ar}$), 133.30, 133.16, 132.94 ($C_{q,ar}$), 129.62 ($CH_{ar}$), 127.64 ($CH_{ar}$), 82.78, 82.44, 82.18 (CH, C-2), 80.19, 80.05 ($C_q$, OtBu), 64.51, 64.22, 64.07, 63.31 ($CH_2$, C-1'), 58.71, 58.40 (CH, C-5), 33.00, 31.19 ($CH_2$, C-3/C-4), 28.24 ($CH_3$, OtBu), 26.78 ($CH_3$, SitBu), 25.67, 25.31, 24.03 ($CH_2$, C-3/C-4), 19.17, 18.81 ($C_q$, SitBu).

IR (ATR): $\tilde{v}$($cm^{-1}$)=3442 (br), 3064 (w), 2955 (m), 2928 (m), 2854 (m), 1679 (vs), 1587 (w), 1471 (m), 1425 (s), 1389 (vs), 1364 (vs), 1255 (m), 1163 (vs), 1104 (vs), 1024 (s), 996 (s), 965 (s), 902 (s), 851 (s), 822 (s), 806 (s), 775 (s), 735 (vs), 698 (vs).

(2R/S,5S)-1-(tert-Butoxycarbonyl)-5-(tert-butyl-diphenylsilanyloxymethyl)-2-methoxypyrrolidine (59)

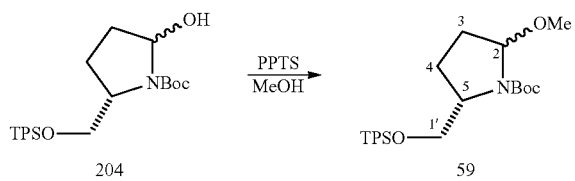

A solution of 2.92 g of 204 (6.41 mmol) in 10 ml of anhydrous MeOH was added with 100 mg of PPTS (0.40 mmol, 6.2 mole %) and stirred at RT overnight. After checking completion of the reaction by means of TLC (EE/CH 1:7), the solution was concentrated, the remaining residue taken up in 25 ml of ethyl acetate and filtered over a small amount of silica gel. The filtrate was concentrated and further purified using silica gel column chromatography (EE/CH 1:7), thereby obtaining 2.98 g of 59 (6.34 mmol, 99%) as a colorless oil.

M ($C_{27}H_{39}NO_4Si$)=469.6884.

$R_f$=0.29/0.33 (SiO$_2$, EE/CH 1:7, diastereomers).

$^1$H-NMR (300 MHz, CDCl$_3$): (mixture of diastereomers/rotamers) δ (ppm)=7.58-7.70 (m, 4H, H$_{ar}$), 7.2-7.45 (m, 6H, H$_{ar}$), 5.21 (br, 0.7H, -2), 5.05 (d, 0.2H, J=4.3 Hz, H-2), 4.93 (d, 0.1H, J=4.4 Hz, H-2), 3.42-4.04 (m, 3H, H-5 and H-1'), 3.37 (s, 0.4H, OCH$_3$), 3.32 (s, 0.3H, OCH$_3$), 3.25 (s, 2.3H, OCH$_3$), 2.00-2.30 (m, 2H, H-3), 1.65-2.00 (m, 2H, H-4), 1.46, 1.32, 1.28 (s/br/s, 9H in total, OtBu), 1.04 (s, 9H, SitBu).

$^{13}$C-NMR (75 MHz, CDCl$_3$): (mixture of diastereomers/rotamers) δ (ppm)=155.14, 154.15, 153.73 (C=O), 135.50 (CH$_{ar}$), 133.79, 133.67, 133.48, 133.31 (C$_{q,ar}$), 129.64, 129.50, 127.57 (CH$_{ar}$), 90.17, 89.77, 89.61 (CH, C-2), 79.85, 79.59 (C$_{q,Boc}$), 66.54 (br, CH$_2$, C-1'), 63.88, 63.76 (CH$_2$, C-1'), 59.15, 58.18 (CH, C-5), 56.35, 55.82, 55.11 (CH$_3$, OCH$_3$), 31.59 (br, CH$_2$, C-3), 28.29, 27.38 (CH$_3$, OtBu), 26.80 (CH$_3$, SitBu), 25.68, 25.43 (CH$_2$, C-4), 19.29 (C$_q$, SitBu).

IR (ATR): ν̃ (cm$^{-1}$)=3069 (w), 3044 (w), 2955 (m), 2927 (m), 2855 (m), 2342 (w), 1959 (w), 1891 (w), 1809 (w), 1696 (vs), 1588 (w), 1471 (m), 1452 (m), 1426 (s), 1364 (vs), 1320 (m), 1255 (m), 1164 (s), 1104 (vs), 1028 (m), 996 (m), 9191 (m), 885 (m), 849 (m), 822 (s), 805 (m), 774 (m), 738 (s), 700 (vs).

MS (DIP-EI, 70 eV): m/z (%)=454 ([M$^+$-CH$_3$], <1), 410 (<1), 396 (<1), 324 (21), 280 (100), 260 (6), 248 (13), 234 (19), 199 (19), 184 (13), 135 (24), 114 (21), 100 (20), 68 (35), 57 (85).

(5S)-1-(tert-Butoxycarbonyl)-5-(tert-butyldiphenylsi-lanyloxymethyl)-2-oxo-3,4-dihydropyrrole (18)

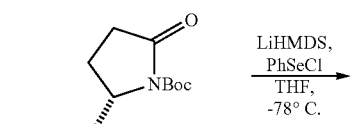

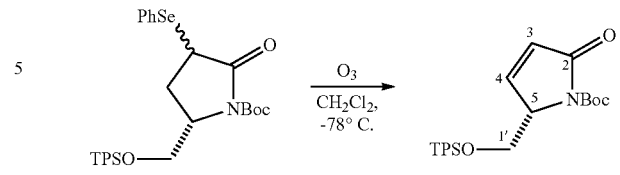

A solution of 10.0 g of 136 (22.0 mmol) in 50 ml of THF was cooled to −78° C., added dropwise with 24.0 ml of LiHMDS (24.0 mmol, 1 M/THF, 1.1 eq.) and stirred for 1 h. Thereafter, a solution of 7.37 g of PhSeCl (38.5 mmol, 1.75 eq.) in 30 ml of THF was added dropwise and stirred for 2 h. After addition of 100 ml of saturated NH$_4$Cl solution, the batch was allowed to come to RT, diluted with 300 ml of MTBE and washed with 50 ml of saturated NH$_4$Cl solution and 50 ml of saturated NaCl solution. The organic phase was dried over MgSO$_4$, filtered from the drying agent and concentrated. Column chromatography over silica gel (EE/CH 1:8) afforded 10.5 g of the selenyl ether 160 (17.3 mmol, 78%) as a yellowish oil.

The latter was taken up in 250 ml of CH$_2$Cl$_2$, cooled to −78° C. and treated with ozone. The reaction was terminated as soon as a blue color began to develop, excess ozone was removed by purging with oxygen, and the reaction was thawed to RT overnight. After concentrating to dryness, the residue was purified using silica gel column chromatography (EE/CH 1:3) to obtain 5.24 g (11.6 mmol, 67%) of the enone 18 as a yellowish oil which gradually solidified.

M ($C_{26}H_{33}NO_4Si$)=451.6301.

$R_f$=0.23 (EE/CH 1:3).

m.p.: 94° C. Lit.: 96° C.

$^1$H-NMR (250 MHz, CDCl$_3$): (mixture of rotamers) δ (ppm)=7.54-7.65 (m, 4H, H$_{ar}$), 7.30-7.47 (m, 6H, H$_{ar}$), 7.25 (dd, 1H, J=6.1 Hz, 2.1 Hz, H-3), 6.15 (dd, J=6.1 Hz, 1.7 Hz, 1H, H-4), 4.63 (ddd, 1H, J=8.0 Hz, J=3.5 Hz, J=1.8 Hz, H-5), 4.10 (dd, 1H, J=9.7 Hz, 3.5 Hz, H-1'$_\alpha$), 3.80 (dd, 1H, J=9.8 Hz, 6.5 Hz, H-1'$_\beta$), 1.41 (s, 9H, O-tBu), 1.01 (s, 9H, Si-tBu).

$^{13}$C-NMR (62.5 MHz, CDCl$_3$): (mixture of rotamers) δ (ppm)=169.46 (C=O, C-2), 149.29, 149.21 (C=O, Boc), 135.45 (CH$_{ar}$), 132.90 (C$_{q,ar}$), 132.64 (CH$_{ar}$), 129.60 (CH$_{olef}$, C-4), 127.81 (CH$_{ar}$), 127.34 (CH$_{olef}$, C-3), 82.88 (C$_{q,Boc}$), 63.44 (CH, C-2), 62.98 (CH$_2$, C-1'), 28.11 (CH$_3$, OtBu), 26.70 (CH$_3$, SitBu), 19.24 (C$_q$, SitBu).

IR (ATR): ν̃ (cm$^{-1}$)=3069 (w), 2930 (m), 2856 (m), 1780 (vs), 1742 (vs), 1709 (vs), 1588 (w), 1472 (w), 1427 (w), 1353 (s), 1319 (vs), 1255 (m), 1160 (s), 1112 (vs), 1044 (m), 981 (w), 821 (m), 740 (m), 702 (vs), 616 (m), 609 (m).

MS (DIP-EI, 70 eV): m/z (%)=378 ([M$^+$-OtBu], 2), 338 (30), 294 (14), 263 (5), 216 (100), 199 (14), 181 (11), 135 (28), 105 (10), 91 (5), 77 (4), 57 (29).

$[α]_D^{20}$=−121.1° (c=0.63, CHCl$_3$). Lit.: −124° (c=0.23, CHCl$_3$).

1-(tert-Butoxycarbonyl)-5-(tert-butyldiphenylsilanyloxymethyl)-2-hydroxypyrrole (161) byproduct of selenium oxide elimination)

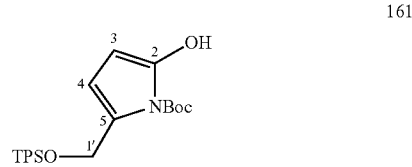

161

$R_f$=0.21 (SiO$_2$, EE/CH 1:3).

$^1$H-NMR (250 MHz, CDCl$_3$): 7.56-7.62 (m, 4H, H$_{ar}$), 7.31-7.44 (m, 6H, H$_{ar}$), 6.88 (d, 1H, J=6.1 Hz), 6.11 (d, 1H, J=6.1 Hz), 4.54 (br, 1H, OH), 4.21 (d, 1H, J=10.2 Hz, H-1'$_\alpha$), 3.84 (d, 1H, J=10.2 Hz, H-1'$_\beta$), 1.51 (s, 9H, OtBu), 1.00 (s, 9H, SitBu).

$^{13}$C-NMR (62.5 MHz, CDCl$_3$): 166.96 (C$_q$), 149.93 (C$_q$), 149.30 (CH$_{olef}$), 135.22 (CH$_{ar}$), 135.16 (CH$_{ar}$), 132.35 (C$_{q,ar}$), 129.69 (CH$_{ar}$), 129.65 (CH$_{ar}$), 127.53 (CH$_{ar}$), 127.24 (CH$_{ar}$), 91.97 (C$_q$), 83.30 (C$_q$), 64.62 (CH$_2$, C-1'), 27.82 (CH$_3$, OtBu), 26.35 (CH$_3$, SitBu), 18.88 (C$_q$, SitBu).

IR (ATR): ṽ (cm$^{-1}$)=3433 (br), 2955 (w), 2928 (w), 2853 (w), 1772 (m), 1753 (m), 1721 (m), 1694 (m), 1469 (w), 1426 (m), 1367 (m), 1329 (s), 1252 (m), 1164 (s), 1112 (vs), 1021 (m), 919 (w), 820 (s), 741 (m), 700 (vs).

(4R,5S)-1-(tert-Butoxycarbonyl)-5-(tert-butyldiphenylsilanyloxymethyl)-2-oxo-4-vinylpyrrolidine (162)

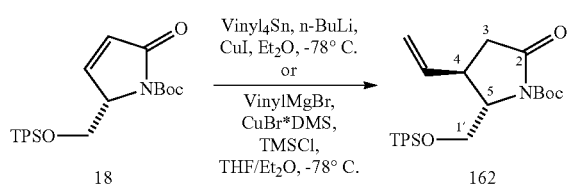

Method A:

A solution of 0.14 ml of tetravinyltin (0.77 mmol, 3.5 eq.) in 2 ml of anhydrous Et$_2$O was added with 1.99 ml of n-BuLi (3.08 mmol, 1.54 M/hexane, 14 eq.) at 0° C. and stirred for one hour. This was subsequently added with 293 mg of anhydrous CuI (1.54 mmol, 7 eq.) at −20° C. to form a black suspension which was cooled to −78° C., followed by dropwise addition of a solution of 100 mg of enone 18 (0.22 mmol) in 2 ml of Et$_2$O. After 2 hours, 2 ml of saturated NH$_4$Cl solution was added dropwise and the reaction mixture was allowed to come to RT. Addition of 15 ml of MTBE and 5 ml of water was followed by filtration over Celite in a separating funnel, the organic phase was washed with 2×3 ml of saturated NH$_4$Cl solution and 3 ml of saturated NaCl solution, dried over MgSO$_4$ and concentrated. Silica gel chromatography (EE/CH 1:7) afforded 64 mg of the addition product 162 (0.13 mmol, 60%) as a colorless oil.

Method B:

A solution of 81.90 ml of vinylmagnesium bromide (81.90 mmol, 1 M/THF, 10 eq.) in 80 ml of anhydrous Et$_2$O was added with 8.41 g of anhydrous CuBr.DMS (40.95 mmol, 5 eq.) at −20° C. to form a black suspension. After 15 min, this was cooled to −78° C., and a solution of 3.70 g of enone 18 (8.19 mmol) in 30 ml of anhydrous Et$_2$O and 2.07 ml of TMSCl (16.38 mmol, 2 eq.) were added. After 2 hours, this was added with 70 ml of saturated NH$_4$Cl solution, and the reaction mixture was heated to RT. Following addition of 300 ml of MTBE and 20 ml of water, the batch was filtered over Celite in a separating funnel, the organic phase was washed with 3×50 ml of saturated NH$_4$Cl solution and 10 ml of saturated NaCl solution, so that the blue color completely disappeared, dried over MgSO$_4$ and concentrated. Column chromatography over silica gel (EE/CH 1:7) afforded 2.30 g (4.79 mmol, 59%) of the vinyl addition product 162 as a yellowish oil.

M (C$_{28}$H$_{37}$NO$_4$Si)=479.6832.

$R_f$=0.32 (EE/CH 1:5).

$^1$H-NMR (300 MHz, CDCl$_3$): (mixture of rotamers) δ (ppm)=7.60 (m, 4H, PhH), 7.40 (m, 6H, PhH), 5.85 (ddd, 1H, J=17.4 Hz, J=8.8 Hz, J=4.6 Hz, CH$_{olef}$), 5.06 (dd, 2H, J=14.2 Hz, J=3.0 Hz, (CH$_{2,olef}$), 3.91 (m, 2H, H-5, H-1'$_\alpha$), 3.72 (dd, 1H, J=11.9 Hz, 3.7 Hz, H-1'$_\beta$), 2.97 (m, 2H, H-3, H-4), 2.31 (td, 2H, J=13.6 Hz, J=6.2 Hz, H-3), 1.41 (s, 9H, OtBu), 1.03 (s, 9H, SitBu).

$^{13}$C-NMR (75 MHz, CDCl$_3$): (mixture of rotamers) δ (ppm)=173.73 (lactam C=O), 149.72 (Boc C$_q$), 139.12 (CH$_{olef}$), 135.50 (CH$_{ar}$), 132.93, 132.56 (C$_{q,ar}$), 129.82, 129.67 (CH$_{ar}$), 127.75, 127.62 (CH$_{ar}$), 115.16 (CH$_{2,olef}$), 82.77 (Boc C$_q$), 64.25 (CH, C-5) 163.84 (CH$_2$, C-1'), 37.84 (CH$_2$, C-3), 36.94 (CH, C-4), 28.32, 27.88 (CH$_3$, OtBu), 26.71 (CH$_3$, SitBu), 19.09 (C$_q$, SitBu).

IR (ATR): ṽ (cm$^{-1}$)=3070 (w), 2955 (m), 2929 (m), 2856 (m), 1787 (s), 1750 (vs), 1711 (vs), 1640 (w), 1588 (w), 1471 (m), 1426 (m), 1391 (m), 1366 (s), 1307 (vs), 1256 (s), 1152 (vs), 1111 (vs), 1062 (m), 1026 (m), 997 (w), 970 (m), 920 (m), 872 (m), 847 (m), 821 (m), 778 (w), 740 (s), 701 (vs), 615 (m).

MS (DIP-EI, 70 eV): m/z (%)=420 ([M$^+$-tBu-2H], <1), 401 (2), 394 (3), 366 (40), 322 (11), 272 (4), 244 (100), 224 (4), 199 (8), 181 (8), 162 (6), 135 (13), 105 (7), 57 (43).

[α]$_D^{20}$=−21.9° (c=0.71, CHCl$_3$). Lit.: −23° (c=0.21, CHCl$_3$).

(2S,3R)-1-(tert-Butoxycarbonyl)-2-(tert-butyldiphenylsilanyloxymethyl)-3-vinylpyrrolidine (163)

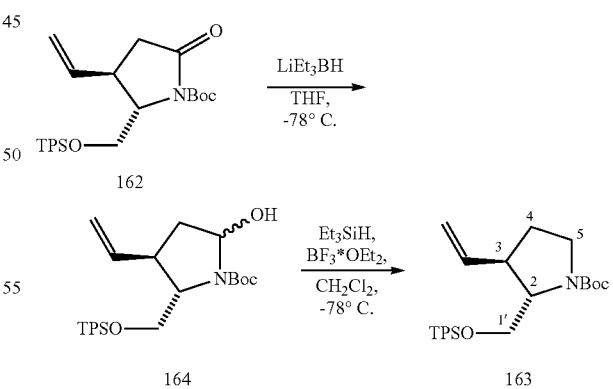

4.90 g of 162 (10.21 mmol) was dissolved in 30 ml of anhydrous THF and cooled to −78° C., followed by dropwise addition of 12.20 ml of LiEt$_3$BH (12.20 mmol, 1.2 eq., 1 M/THF). After one hour, this was added with 10 ml of K—Na tartrate solution (1.77 M), and the batch was allowed to come to RT. For work-up, 50 ml of MTBE was added, the aqueous phase was extracted with 2×10 ml of MTBE and the combined organic phases were dried over MgSO$_4$. Removal of solvent in vacuum afforded crude 164 as a colorless oil which was dried under oil pump vacuum.

The crude 164 was taken up in 30 ml of anhydrous CH$_2$Cl$_2$, cooled to −78° C., added with 3.20 ml of Et$_3$SiH (20.14 mmol, 2 eq.) and 2.80 ml of BF$_3$.OEt$_2$ (22.10 mmol, 2.2 eq.) and stirred for two hours. Following addition of 10 ml of saturated NaHCO$_3$ solution, the reaction mixture was heated to RT. The batch was diluted with 100 ml of MTBE, the organic phase was washed with 10 ml of saturated NH$_4$Cl solution and dried over MgSO$_4$. After concentrating, the residue was purified using silica gel column chromatography (EE/CH 1:15), thereby obtaining 3.10 g of 163 (6.66 mmol, 65%) as a colorless oil.

M (C$_{28}$H$_{39}$NO$_3$Si)=465.6997.

Rf=0.23 (SiO$_2$, EE/CH 1:15).

$^1$H-NMR (500 MHz, CDCl$_3$): (mixture of rotamers) δ (ppm)=7.61-7.71 (m, 4H, H$_{ar}$), 7.30-7.45 (m, 6H, H$_{ar}$), 5.79 (qd, 1H, J=17.6 Hz, J=9.6 Hz, (CH$_{olef.}$), 5.07 (m, 2H, CH$_{2,olef.}$), 4.09 (d, 0.4H, J=6.4 Hz, CH$_2$, H-1'$_\alpha$), 3.50-3.56 (m, 3.6H, H-2, H-5$_\alpha$, H-1'$_\beta$), 3.35 (td, 1H, J=11.0 Hz, J=6.9 Hz, H-5$_\beta$), 3.11 (m, 1H, H-3), 2.08 (qt, 1H, J=13.0 Hz, J=6.5 Hz, H-4$_\alpha$), 1.72 (td, 1H, J=13.3 Hz, J=7.0 Hz, H-4$_\beta$), 1.45, 1.31 (2 s, 9H, OtBu), 1.04, 1.03 (2 s, 9H, SitBu).

$^{13}$C-NMR (125 MHz, CDCl$_3$): (mixture of rotamers) δ (ppm)=154.13 (C=O), 139.69, 139.54 (CH$_{olef.}$), 135.40 (CH$_{ar}$), 133.61, 133.38, 133.24 (C$_{q,ar}$), 129.52 (CH$_{ar}$), 127.53 (CH$_{ar}$), 114.80, 114.56 (CH$_{2,olef.}$), 79.05, 78.75 (Boc C$_q$), 63.40, 63.29 (CH, C-2), 63.14, 61.84 (CH$_2$, C-1'), 46.58, 45.87 (CH$_2$, C-5), 44.74, 43.98 (CH, C-3), 30.46, 29.51 (CH$_2$, C-4), 28.30, 28.15 (CH$_3$, OtBu), 26.73 (CH$_3$, SitBu), 19.16 (C$_q$, SitBu).

IR (ATR): $\tilde{v}$ (cm$^{-1}$)=3070 (w), 3047 (w), 2960 (m), 2928 (m), 2856 (m), 1693 (vs), 1640 (w), 1588 (w), 1471 (m), 1426 (m), 1391 (s), 1364 (s), 1344 (w), 1255 (w), 1171 (s), 1111 (vs), 1029 (w), 1006 (w), 989 (w), 914 (m), 899 (m), 859 (w), 822 (m), 772 (m), 740 (m), 700 (s), 604 (m).

MS (DIP-EI, 70 eV): m/z (%)=408 ([M$^+$-tBu], 1), 392 (5), 380 (3), 368 (4), 352 (100), 306 (8), 253 (7), 230 (57), 211 (5), 199 (60), 181 (24), 168 (6), 140 (81), 121 (7), 105 (6), 96 (24), 77 (2), 57 (2).

HRMS (ESI, C$_{28}$H$_{39}$NNaO$_3$Si): calc.: 488.2597. found: 488.260.

[α]$_\lambda^{20}$=−34.0° (589 nm), −40.4° (546 nm), −83.5° (405 nm), −110.2° (365 nm), −142.2° (334 nm) (c=0.725, CHCl$_3$).

CHN analysis: calc.: C, 72.21%; H, 8.44%; N, 3.01%.
found: C, 71.78%; H, 8.50%; N, 2.88%.

(2S,3R)-1-(tert-Butoxycarbonyl)-2-(hydroxymethyl)-3-vinylpyrrolidine (165)

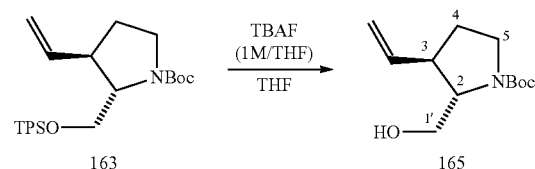

2.67 g of 163 (5.73 mmol) was dissolved in 35 ml of anhydrous THF, cooled to 0° C. and added with 8.60 ml of TBAF solution (8.60 mmol, 1.5 eq., 1 M/THF). After reacting at RT overnight, 0.5 ml of water was added, followed by stirring for 30 min. Thereafter, the batch was filtered together with a small amount of MTBE over a small amount of silica gel and concentrated. Column chromatography over silica gel (EE/CH 1:3) afforded 1.28 g of alcohol 165 (5.63 mmol, 98%) as a colorless oil.

M (C$_{12}$H$_2$, NO$_3$)=227.3001.

Rf=0.18 (SiO$_2$, EE/CH 1:3).

$^1$H-NMR (300 MHz, CDCl$_3$): δ (ppm)=5.72 (m, 1H, CH$_{olef.}$), 5.06 (ddd, 2H, J=8.7 Hz, J=4.9 Hz, J=3.8 Hz, CH$_{2,olef.}$), 3.71 (t, 1H, J=8.9 Hz, H-1'$_\alpha$), 3.54 (m, 3H, H-2, H-5$_\alpha$, H-1'$_\beta$), 3.20 (ddd, 1H, J=10.9 Hz, J=9.8 Hz, J=6.5 Hz, H-5$_\beta$), 2.31 (br, 1H, H-3), 1.91 (br, 1H, H-4$_\alpha$), 1.62 (m, 1H, H-4$_\beta$), 1.42 (s, 9H, OtBu).

$^{13}$C-NMR (75 MHz, CDCl$_3$): δ (ppm)=156.56 (C$_q$, C=O), 137.93 (CH$_{olef.}$), 116.32 (CH$_{2,olef.}$), 80.09 (Boc C$_q$), 65.54 (CH$_2$, C-1'), 64.94 (CH, C-2), 46.52 (CH$_2$, C-5), 45.87 (CH, C-3), 30.40 (CH$_2$, C-4), 28.25 (CH$_3$ OtBu).

IR (ATR): $\tilde{v}$ (cm$^{-1}$)=3407 (br), 3078 (w), 2973 (s), 2930 (m), 2879 (m), 1692 (vs), 1669 (vs), 1477 (s), 1453 (s), 1404 (vs), 1365 (vs), 1344 (m), 1253 (m), 1169 (vs), 1117 (s), 1086 (m), 1054 (m), 992 (m), 916 (m), 894 (w), 861 (w), 772 (m), 668 (w).

MS (GCMS-EI, 70 eV): m/z (%)=227 ([M$^+$], <1), 207 (<1), 196 (13), 154 (10), 140 (52), 96 (71), 81 (4), 67 (13), 57 (100).

HRMS (ESI, C$_{12}$H$_{27}$NNaO$_3$): calc.: 250.1419. found: 250.142.

[α]$_\lambda^{20}$=−52.5° (589 nm), −123.7° (405 nm), −159.2° (365 nm), −199.2° (334 nm), −62.0° (546 nm), (c=1.08, CHCl$_3$).

CHN analysis: C, 63.41%; H, 9.31%; N, 6.16%.
C, 63.22%; H, 9.48%; N, 6.28%.

(2S,3R)-1-(tert-Butoxycarbonyl)-3-vinylpyrrolidine-2-carboxylic acid (166)

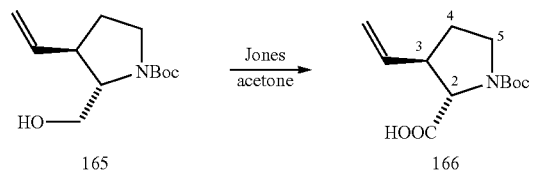

600 mg of alcohol 165 (2.64 mmol) was dissolved in 15 ml of acetone, cooled to 0° C. and added dropwise with 5 ml of Jones reagent (7.40 mmol, 2.8 eq.) (freshly prepared from 2 g of CrO$_3$, 2.7 g of conc. H$_2$SO$_4$, 12 ml of H$_2$O) and stirred for 2 h at RT, the course of the reaction being monitored using TLC (EE/CH 1:1). This was followed by addition of 4 ml of isopropanol, during which the orange color of the reaction mixture gradually turned green-brown. Filtration over Celite was followed by washing with 5 ml of an acetone/glacial acetic acid mixture (20:1) and concentrating to dryness. The remaining greenish residue was purified using silica gel column chromatography (CH$_2$Cl$_2$/MeOH 20:1), thereby obtaining 470 mg of vinylproline 166 (1.95 mmol, 74%) in the form of white crystals suitable for X-ray crystallographic analysis.

M (C$_{12}$H$_{19}$NO$_4$)=241.2836.

R$_f$=0.26 (SiO$_2$, CH$_2$Cl$_2$/MeOH 19:1).

m.p.: 116-118° C.

$^1$H-NMR (300 MHz, CDCl$_3$): (mixture of rotamers) δ (ppm)=10.70 (br, 1H, COOH), 5.81 (ddd, 1H, J=17.3 Hz, J=10.3 Hz, J=7.3 Hz, CH$_{olef.}$), 5.12 (m, 2H, CH$_{2,olef.}$), 4.09/3.95 (2d, 1H, J=5.6 Hz, H-2), 3.55 (m, 2H, H-5), 2.98 (m, 1H, H-3), 2.08 (m, 1H, H-4$_\alpha$), 1.77 (m, 1H, H-4$_\beta$), 1.45, 1.39 (2 s, 9H, OtBu).

$^{13}$C-NMR (75 MHz, CDCl$_3$): (mixture of rotamers) δ (ppm)=177.89, 176.37 (carboxylic C=O), 155.05, 153.73 (Boc C=O), 137.09, 136.84 (CH$_{olef.}$), 116.35, 116.01 (CH$_{2,olef.}$), 80.65, 80.55 (Boc C$_q$), 64.06, 63.73 (CH, C-2), 48.19, 45.76 (CH, C-3), 45.93, 45.64 (CH$_2$, C-5), 30.53, 30.24 (CH$_2$, C-4), 28.29, 28.15 (CH$_3$ OtBu).

IR (ATR): ṽ (cm$^{-1}$)=3085 (br), 2975 (s), 2873 (m), 2559 (br), 2245 (w), 1744 (vs), 1696 (br, vs), 1477 (s), 1391 (vs), 1365 (vs), 1242 (s), 1161 (vs), 1119 (vs), 989 (m), 913 (vs), 858 (m), 772 (m), 730 (s), 681 (m), 646 (w).

MS (DIP-EI, 70 eV): m/z (%)=241 ([M$^+$], <1), 207 (1), 196 (5), 168 (3), 140 (100), 126 (5), 110 (3), 96 (77), 87 (3), 79 (4), 68 (16), 57 (88).

ESI-MS (C$_{12}$H$_{19}$NNaO$_4$): calc.: 264.12. found: 264.30.

[α]$_\lambda^{20}$=−38.5° (589 nm), −45.6° (546 nm), −98.7° (405 nm), −133.4° (365 nm), absorption at 334 nm (c=0.765, CHCl$_3$).

CHN analysis: calc.: C, 59.73%; H, 7.94%; N, 5.81%.
found: C, 59.68%; H, 7.89%; N, 5.63%.

Crystal Data:

| | |
|---|---|
| Identification code: | jz101 |
| Empirical formula: | C$_{12}$H$_{19}$NO$_4$ |
| Formula weight: | 241.28 |
| Temperature: | 100(2) K |
| Wavelength: | 0.71973 Å |
| Crystal system, space group: | orthorhombic, P2$_1$2$_1$2$_1$ |
| Unit cell dimensions: | a = 9.2926(2) Å  α = 90° |
| | b = 11.8100(3) Å  β = 90° |
| | c = 12.1256(2) Å  γ = 90° |
| Volume: | 1330.73(5) Å$^3$ |
| Z, calculated density: | 4, 1.204 g/cm$^3$ |
| Absorption coefficient: | 0.090 mm |
| F(000): | 520 |
| Crystal size: | 0.1 × 0.1 × 0.2 mm |
| Theta range for data collection: | 2.44 to 27.00° |
| Limiting indices: | −11 ≦ h ≦ 11, −14 ≦ k ≦ 14, −15 ≦ l ≦ 15 |
| Reflections collected/unique: | 11042/2797 [R(int) = 0.0266] |
| Reflection observed [I > 2sigma(I)] | 2494 |
| Completeness to theta = 25.00 | 100% |
| Absorption correction: | none |
| Refinement method: | Full-matrix least squares on F$^2$ |
| Data/restraints/parameters: | 2797/0/230 |
| Goodness-of-fit on F$^2$: | 1.043 |
| Final R indices [I > 2sigma(I)]: | R$_1$ = 0.0306, wR$_2$ = 0.0751 |
| R indices (all data): | R$_1$ = 0.0368, wR$_2$ = 0.0784 |
| Absolute structure parameter: | −0.2(8) |
| Largest diff. peak/hole: | 0.155 and −0.158 eÅ$^3$ |

(2S)-1-(tert-Butoxycarbonyl)-5-oxopyrrolidine-2-carboxylic acid ethyl ester (167)

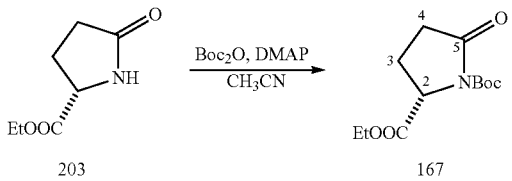

A solution of 7.00 g of pyroglutamic acid ethyl ester 203 (44.5 mmol) in 60 ml of anhydrous acetonitrile was cooled to 0° C. and added with 6.3 ml of NEt$_3$ (45.4 mmol, 1.02 eq.), a trace of DMAP and 10.5 ml of Boc$_2$O (49.1 mmol, 1.1 eq.). After stirring for 15 h at RT, the solvent was removed and the residue was purified using silica gel column chromatography (EE/CH 1:1). The yellowish solid product was further purified by recrystallization from Et$_2$O/pentane to obtain 11.0 g of 167 (42.9 mmol, 96%) in the form of white crystals.

M (C$_{12}$H$_{19}$NO$_5$)=257.2830.
R$_f$=0.31 (SiO$_2$, EE/CH 1:1).
m.p.: 53° C. Lit.: 50-51° C.

$^1$H-NMR (500 MHz, CDCl$_3$): δ (ppm)=4.57 (dd, 1H, J=9.5 Hz, J=2.9 Hz, H-2), 4.21 (q, 2H, J=7.1 Hz, ester CH$_2$), 2.60 (td, 1H, J=17.5 Hz, J=9.9 Hz, H-4$_α$), 2.46 (ddd, 1H, J=17.5 Hz, J=9.4 Hz, J=3.5 Hz, H-4$_β$), 2.29 (qd, 1H, J=13.3 Hz, J=9.7 Hz, H-3$_α$), 2.00 (tdd, 1H, J=13.0 Hz, J=9.6 Hz, J=3.2 Hz, H-3$_β$), 1.51 (s, 9H, OtBu), 1.27 (t, 1H, J=7.1 Hz, ester CH$_3$).

$^{13}$C-NMR (125 MHz, CDCl$_3$): δ (ppm)=173.31 (C=O), 171.30 (C=O), 83.54 (Boc C$_q$), 61.64 (ester CH$_2$), 58.93 (CH, C-2), 31.14 (CH$_2$, C-4), 27.86 (CH$_3$, OtBu), 21.53 (CH$_2$, C-3), 14.16 (CH$_3$, ester).

IR (ATR): ṽ (cm$^{-1}$)=2977 (m), 2932 (w), 1788 (vs), 1741 (vs), 1713 (vs), 1475 (m), 1457 (m), 1393 (m), 1367 (s), 1306 (vs), 1284 (vs), 1254 (vs), 1189 (vs), 1146 (vs), 1095 (m), 1042 (s), 1019 (vs), 958 (w), 914 (w), 883 (w), 842 (m), 819 (m), 777 (m), 746 (m), 639 (w).

MS (DIP-EI, 70 eV): m/z (%)=242 ([M$^+$−15], <1), 202 (1), 184 (10), 158 (9), 156 (8), 149 (1), 128 (2), 110 (8), 84 (83), 75 (3), 69 (4), 57 (100).

[α]$_D^{20}$=−34.9° (c=0.810, CHCl$_3$). Lit.: −32.3° (c=2.1, CHCl$_3$).

(2S,5R/S)-1-(tert-Butoxycarbonyl)-5-hydroxypyrrolidine-2-carboxylic acid ethyl ester (205)

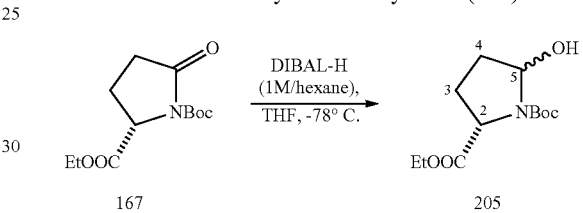

A solution of 10.0 g of 167 (38.9 mmol) in 100 ml of anhydrous THF was cooled to −78° C. and added very slow with 85.5 ml of DIBAL-H (85.5 mmol, 2.2 eq., 1 M/THF). After one hour, the reaction was terminated by adding 10 ml of isopropanol at low temperature, followed by addition of 240 ml of a K—Na tartrate solution (1.77 M), and the mixture was slowly thawed, initially to 0° C. and subsequently to RT. The resulting phases were separated, the organic phase was extracted with 3×200 ml of MTBE, and the combined organic phases were washed with 100 ml of saturated NaCl solution. After drying over MgSO$_4$, the solvent was removed to obtain 9.69 g of 205 (37.4 mmol, 96%) as a yellowish oily residue which was further reacted without purification. For analytical purposes, a small sample was purified using silica gel column chromatography (EE/CH 1:1).

M (C$_{12}$H$_{21}$NO$_5$)=259.2989.
Rf=0.27 (SiO$_2$, EE/CH of 1:1).

$^1$H-NMR (300 MHz, CDCl$_3$): (mixture of diastereomers/rotamers) δ (ppm)=5.40-5.70 (m, 1H, H-5), 4.06-4.40 (m, 3H, H-2 and ester CH$_2$), 3.40-3.75 (m, 1H, OH), 1.77-2.60 (m, 4H, H-3, H-4), 1.35-1.52 (m, 9H, tBu), 1.17-1.30 (m, 2H, ester CH$_3$).

$^{13}$C-NMR (75 MHz, CDCl$_3$): (mixture of diastereomers/rotamers) δ (ppm)=173.01, 172.75, 172.45, 172.18 (ester C=O), 154.03, 153.82, 153.15 (Boc C=O), 82.16, 81.91, 81.67 (CH, C-5), 80.96, 80.87, 80.71 (C$_q$, OtBu), 61.10, 60.90, 60.83 (ester CH$_2$), 59.43, 59.15, 59.00 (CH, C-2), 32.31, 31.77, 31.05 (CH$_2$, C-4), 28.27, 28.08 (CH$_3$, OtBu), 27.80, 27.69, 26.83, 26.77 (CH$_2$, C-3), 14.14, 13.99 (ester CH$_3$.

IR (ATR): ṽ (cm$^{-1}$)=3480 (br), 2976 (m), 1741 (s), 1696 (vs), 1476 (m), 1452 (m), 1364 (vs), 1323 (m), 1256 (m), 1156 (vs), 1123 (s), 1061 (m), 1025 (vs), 973 (m), 914 (m), 848 (m), 775 (m).

MS (DIP-EI, 70 eV): m/z (%)=258 ([M$^+$-H], <1), 242 (10), 208 (3), 202 (4), 186 (3), 158 (18), 142 (100), 130 (6), 114 (3), 86 (14), 68 (28), 57 (37).

(2S,5R/S)-1-(tert-Butoxycarbonyl)-5-methoxypyrrolidine-2-carboxylic acid ethyl ester (168)

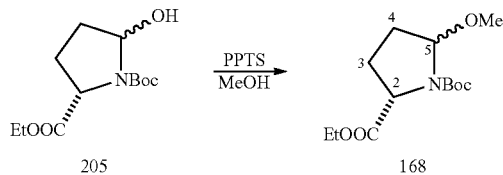

A solution of 9.69 g of 205 (37.4 mmol) in 100 ml of anhydrous MeOH was added with 200 mg of PPTS (0.80 mmol, 2.1 mole %) and stirred at RT overnight. Thereafter, the solvent was completely removed and the remaining residue was purified using silica gel column chromatography (EE/CH 1:3) to obtain 9.56 g of α-methoxycarbamate 168 (35.0 mmol, 94%) as a colorless oil (mixture of diastereomers).

M ($C_{13}H_{23}NO_5$)=273.3255.

$R_f$=0.26 (SiO$_2$, EE/CH 1:3).

$^1$H-NMR (500 MHz, CDCl$_3$): (mixture of diastereomers/rotamers) δ (ppm)=5.11-5.29 (m, 1H, H-5), 4.05-4.38 (m, 3H, ester CH$_2$, H-2), 3.37 (m, 3H, OCH$_3$), 1.65-2.50 (m, 4H, H-3, H-4), 1.39, 1.41, 1.46, 1.48 (4 s, 9H, Boc), 1.25 (m, 3H, ester CH$_3$).

$^{13}$C-NMR (125 MHz, CDCl$_3$): (mixture of diastereomers/rotamers) δ (ppm)=172.60, 172.28 (ester C=O), 154.15, 153.95, 153.81, 153.74 (Boc C=O), 89.16, 89.11, 88.34, 88.16 (CH, C-5), 80.52, 80.37, 80.30 (Boc C$_q$), 60.73 (ester CH$_2$), 59.50, 59.21, 58.88, 58.81 (CH, C-2), 56.00, 55.72, 55.11, 54.78 (CH$_3$, OCH$_3$), 32.78, 32.10, 30.92, 29.90 (CH$_2$, C-4), 28.15, 27.99 (Boc CH$_3$), 27.64, 26.93, 26.83 (CH$_2$, C-3), 14.10, 13.96 (ester CH$_3$).

IR (ATR): $\tilde{v}$ (cm$^{-1}$)=2976 (m), 2935 (m), 1746 (s), 1707 (vs), 1476 (m), 1456 (m), 1442 (m), 1375 (vs), 1329 (m), 1255 (m), 1185 (vs), 1116 (m), 1085 (vs), 1035 (m), 939 (m), 912 (m), 844 (m), 773 (m).

MS (GCMS-EI, 70 eV): m/z (%)=241 ([M$^+$-MeOH], 2), 200 (12), 172 (8), 142 (24), 100 (48), 68 (100), 57 (88), 41 (63).

(2S,5R/S)-5-Allyl-1-(tert-butoxycarbonyl)pyrrolidine-2-carboxylic acid ethyl ester (169)

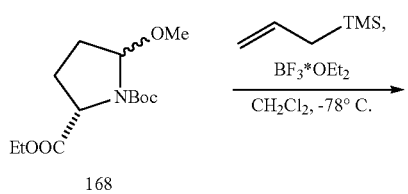

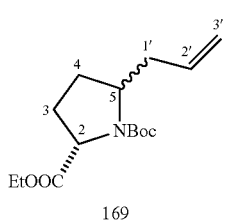

169

A solution of 9.25 g of α-methoxycarbamate 168 (33.8 mmol) in 100 ml of anhydrous CH$_2$Cl$_2$ was cooled to −78° C., added initially with 13.50 ml of allyltrimethylsilane (84.6 mmol, 2.5 eq.), followed by dropwise addition of 8.58 ml of BF$_3$.OEt$_2$ (67.7 mmol, 2 eq.) and stirring for one hour. Thereafter, 10 ml of H$_2$O and 30 ml of saturated NaHCO$_3$ solution were added at low temperature, the batch was allowed to come to 0° C., stirred for 30 min and thawed to RT. After separating the phases, the aqueous phase was extracted with 3×50 ml of CH$_2$Cl$_2$, the combined organic phases were washed with 30 ml of saturated NaCl solution and dried over MgSO$_4$. After removing the solvent, the residue was purified using silica gel column chromatography (EE/CH 1:6) to obtain 6.83 g of allyl substitution product 169 (24.1 mmol, 71%) as a colorless oil (mixture of epimers, cis/trans 4:1).

M ($C_{15}H_{25}NO_4$)=283.3633.

$R_f$=0.39 (SiO$_2$, EE/CH 1:3).

$^1$H-NMR (500 MHz, CDCl$_3$): (mixture of diastereomers/rotamers) δ (ppm)=5.70 (m, 1H, H-2'), 4.95 (m, 2H, H-3'), 4.00-4.28 (m, 3H, H-2, ester CH$_2$), 3.76, 3.87 (2br, 1H, H-5), 2.32-2.70 (m, 1H, H-1'$_\alpha$), 1.62-2.23 (m, 5H, H-1'$_\beta$), H-3, H-4), 1.35, 1.36, 1.41, 1.42 (4 s, 9H, OtBu), 1.21 (m, 3H, ester CH$_3$).

$^{13}$C-NMR (125 MHz, CDCl$_3$): (mixture of diastereomers/rotamers) δ (ppm)=173.31, 173.11, 172.72 (ester C=O), 153.49 (Boc C=O), 135.34, 135.06, 134.99 (CH$_{2,olef.}$, C-3'), 117.20, 117.12, 116.77 (CH$_{2,olef.}$, C-2'), 79.78 (Boc C$_q$), 60.77, 60.74 (ester CH$_2$), 60.15, 59.91, 59.84, 59.59 (CH, C-2), 58.00, 57.89, 57.46, 57.41 (CH, C-5), 39.01, 38.94, 38.10, 38.05 (CH$_2$, O-1'), 29.45, 28.72, 28.40 (CH$_2$, C-3/C-4), 28.32, 28.20 OtBu), 27.96, 27.75, 27.40, 26.75 (CH$_2$, C-3/C-4), 14.21, 14.17 (ester CH$_3$).

IR (ATR): $\tilde{v}$ (cm$^{-1}$)=3074 (w), 2974 (s), 2931 (m), 1746 (s), 1696 (vs), 1639 (w), 1477 (m), 1451 (m), 1388 (vs), 1365 (vs), 1329 (m), 1273 (m), 1256 (m), 1184 (vs), 1165 (vs), 1123 (s), 1105 (s), 1031 (m), 995 (m), 948 (m), 912 (m), 859 (m), 770 (m)

MS (GCMS-EI, 70 eV): m/z (%)=242 ([M$^+$-C$_3$H$_5$], 6), 210 (3), 182 (3), 154 (6), 142 (100), 114 (5), 110 (8), 96 (3), 68 (20) 57 (40).

[α]$_D^{20}$=−26.4° (c=1.025, CHCl$_3$).

(2S,5R/S)-1-(tert-Butoxycarbonyl)-5-(2-hydroxyethyl)pyrrolidine-2-carboxylic acid ethyl ester (170)

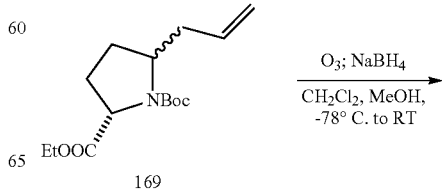

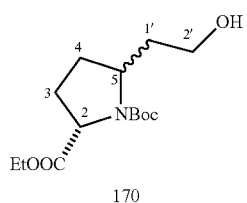

170

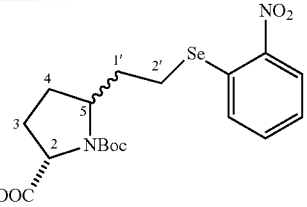

171

Ozone was passed at −78° C. through a solution of 1.00 g of 169 (3.53 mmol) in a mixture of 12 ml of MeOH and 6 ml of CH$_2$Cl$_2$ until the solution turned blue. The reaction was subsequently terminated and excess ozone removed by purging with oxygen. Thereafter, 270 mg of NaBH$_4$ (7.06 mmol, 2 eq.) was added and the mixture stirred overnight to allow warming to RT. After checking completion of the reaction by means of TLC (EE/CH 1:1), the batch was concentrated and the remaining residue taken up in 60 ml of CH$_2$Cl$_2$ and 40 ml of half-conc. NaCl solution. The aqueous phase was extracted with 3×20 ml of CH$_2$Cl$_2$, the combined organic phases were dried over MgSO$_4$ and concentrated. The residue was purified using silica gel column chromatography (EEICH 1:1) to obtain 691 mg (2.40 mmol, 68%) of alcohol 170 as a mixture of epimers (colorless oil).

M (C$_{14}$H$_{25}$NO$_5$)=287.3520.

R$_f$=0.20 (SiO$_2$, EE/CH 1:1).

$^1$H-NMR (300 MHz, CDCl$_3$): (mixture of diastereomers/rotamers) δ (ppm)=3.95-4.33 (m, 5H, H-2, H-5, ester CH$_2$, OH), 3.42-3.78 (m, 2H, CH$_2$), 1.45-2.33 (m, 6H, 3×CH$_2$), 1.43, 1.37 (2 s, 9H, OtBu), 1.22 (t, 3H, J=6 Hz, ester CH$_3$).

$^{13}$C-NMR (75 MHz, CDCl$_3$): (mixture of diastereomers/rotamers) δ (ppm)=173.24 (ester C=O), 155.54, 155.32 (Boc C=O), 80.75, 80.60 (Boc C$_q$), 60.90 (ester CH$_2$), 59.99 (CH, C-2), 59.01, 58.74 (CH$_2$), 54.47, 54.30 (CH, C-5), 38.78, 37.57 (CH$_2$), 30.52 (CH$_2$), 29.10, 28.77, 28.62 (CH$_2$), 28.11 (CH$_3$, Bu), 14.14 (ester CH$_3$).

IR (ATR): ṽ (cm$^{-1}$)=3444 (br), 2975 (m), 2873 (m), 1743 (s), 1674 (vs), 1476 (m), 1451 (m), 1390 (vs), 1364 (vs), 1299 (m), 1256 (m), 1156 (vs), 1116 (vs), 1069 (s), 1034 (s), 991 (m), 926 (w), 854 (m), 773 (m).

MS (DIP-EI, 70 eV): m/z (%)=287 ([M$^+$], 1), 231 (2), 214 (8), 186 (4), 158 (8), 142 (23), 128 (3), 114 (100), 96 (4), 82 (3), 68 (16), 57 (54).

[α]$_D^{20}$=−48.9° (c=0.885, CHCl$_3$).

(2S,5R/S)-1-(tert-Butoxycarbonyl)-5[2-(2-nitrophenylselanyl)ethyl]pyrrolidine-2-carboxylic acid ethyl ester (171)

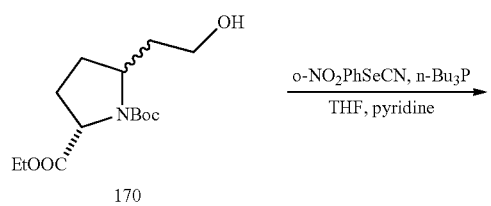

170

497 mg of alcohol 170 (1.73 mmol) was dissolved and 432 mg of ortho-nitrophenyl selenocyanate (1.90 mmol, 1.1 eq.) suspended in a solvent mixture consisting of 10 ml of anhydrous THF and 3 ml of anhydrous pyridine. This was followed by careful dropwise addition of 0.56 ml of tri-n-butylphosphine (2.25 mmol, 1.3 eq.) at 0° C. to obtain a dark-red solution. After one hour, the batch was diluted with 30 ml of MTBE, filtered over a small amount of silica gel and concentrated. The brown residue was purified using column chromatography over silica gel (EE/CH 1:3), thereby obtaining 685 mg of selenyl ether 171 (1.45 mmol, 84%) as an intensely yellow-colored oil.

M (C$_{20}$H$_{28}$N$_2$O$_6$Se)=471.4062.

R$_f$=0.26 (SiO$_2$, EE/CH 1:3).

$^1$H-NMR (250 MHz, CDCl$_3$): (mixture of diastereomers/rotamers) δ (ppm)=8.10-8.35 (m, 1H, H$_{ar}$), 7.20-7.70 (m, 3H, H$_{ar}$), 3.95-4.40 (m, 4H, C-2, C-5, ester CH$_2$), 2.75-3.12 (m, 2H, CH$_2$), 1.62-2.35 (m, 6H, 3×CH$_2$), 1.37-1.45 (m, 9H, OtBu), 1.19-1.28 (m, 3H, ester CH$_3$).

(2S,5R/S)-1-(tert-Butoxycarbonyl)-5-vinylpyrrolidine-2-carboxylic acid ethyl ester (172)

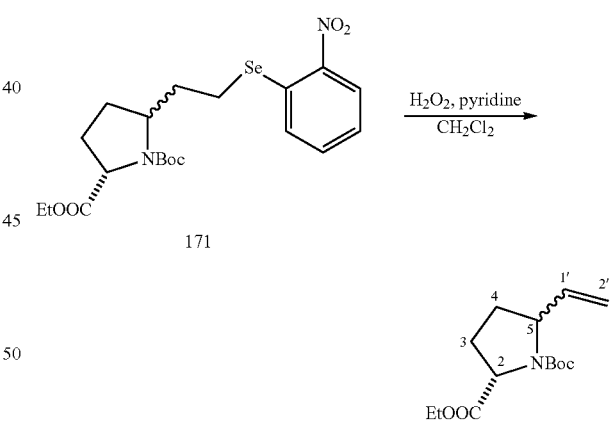

171

172

A solution of 576 mg of selenyl ether 171 (1.22 mmol) in 15 ml of anhydrous CH$_2$Cl$_2$ was cooled to 0° C., added with 0.4 ml of pyridine and 0.8 ml H$_2$O$_2$ (30%) and stirred overnight. The intensely orange-colored solution was subsequently concentrated and purified using silica gel column chromatography (CH$_2$Cl$_2$) to obtain 312 mg of vinylproline 172 (1.16 mmol, 95%) as a yellowish oil.

M (C$_{14}$H$_{23}$NO$_4$)=269.3368.

R$_f$=0.10 (SiO$_2$, CH$_2$Cl$_2$).

$^1$H-NMR (300 MHz, CDCl$_3$): (mixture of diastereomers/rotamers) δ (ppm)=5.60-5.90 (m, 1H, CH$_{olef}$, H-1'), 4.92-5.38 (m, 2H, CH$_{2,olef}$, H-2'), 4.02-4.55 (m, 4H, H-2, H5, ester CH$_2$), 1.66-2.25 (m, 4H, H-3, H-4), 1.35, 1.34 (2 s, 9H, OtBu), 1.22 (t, 3H, J=9 Hz, ester CH$_3$).

$^{13}$C-NMR (75 MHz, CDCl$_3$): (mixture of diastereomers/rotamers) δ (ppm)=172.98, 172.91, 172.79 (ester C=O), 153.47, 153.28, 153.27 (Boc C=O), 138.90, 138.32, 138.12, 137.79 (CH$_{olef}$, C-1'), 114.90, 114.64, 113.90, 113.69 (CH$_{2,olef}$, C-2'), 79.86, 79.81, 79.70 (Boc C$_q$), 60.74 (ester CH$_2$), 60.52, 60.22, 59.91, 59.61, 59.53, 59.33, 59.18 (2×CH, C-2, C-5), 31.47, 31.01, 30.84, 30.69, 30.46, 30.11, 29.83, 29.03, 28.79, 27.21 (2×CH$_2$, C-3, C-4), 28.18 (CH$_3$, OtBu), 14.17, 14.07 (ester CH$_3$).

IR (ATR): ṽ (cm$^{-1}$)=3078 (w), 2975 (m), 2928 (m), 1744 (vs), 1692 (vs), 1643 (w), 1477 (m), 1454 (m), 1383 (vs), 1364 (vs), 1284 (s), 1254 (s), 1157 (vs), 1110 (vs), 1068 (m), 1031 (s), 991 (m), 913 (s), 859 (s), 769 (s), 680 (w).

MS (GCMS-EI, 70 eV): m/z (%)=269 ([M$^+$], <1), 213 (4), 196 (11), 168 (8), 140 (60), 96 (100), 79 (8), 67 (8), 57 (77).

[α]$_D^{20}$=−56.2° (c=1.13, CHCl$_3$).

(2S,5R/S)-5-Vinylpyrrolidine-2-carboxylic acid ethyl ester (174)

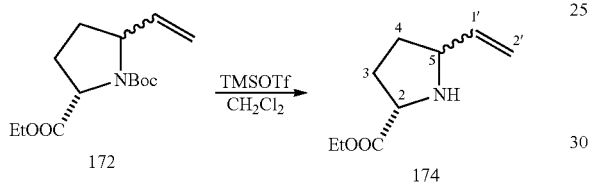

130 mg of 172 (0.46 mmol) was dissolved in 3 ml of anhydrous CH$_2$Cl$_2$, cooled to 0° C. and added dropwise with 90 ml of TMSOTf (0.466 mmol, 1.01 eq.). After 15 min, this was added with 0.5 ml of saturated NaHCO$_3$ solution, 0.5 ml of H$_2$O and 10 ml of Et$_2$O, and the batch was allowed to come to RT. Following phase separation, the organic phase was dried over MgSO$_4$, filtered and concentrated. The resulting crude product was purified using silica gel column chromatography (DCM/MeOH 25:1) to isolate 54 mg of amine 174 (0.32 mmol, 70%) as a slightly yellowish oil (mixture of diastereomers, cis/trans=4:1).

M (C$_9$H$_{15}$NO$_2$)=169.2209.

R$_f$=0.19 (SiO$_2$, CH$_2$Cl$_3$/MeOH 25:1).

$^1$H-NMR (300 MHz, CDCl$_3$): (mixture of diastereomers) δ (ppm)=5.67-5.88 (m, 1H, H-1'), 5.07-5.18 (m, 1H, H-2'$_α$), 4.93-5.02 (m, 1H, H-2'$_β$), 4.08-4.17 (m, 2H, ester CH$_2$), 3.77-3.84 (m, 0.2H, H-2), 3.65-3.76 (m, 1H, H-2, H-5), 3.50-3.61 (m, 0.8H, H-5), 2.22 (br, 1H, NH), 1.98-2.18 (m, 1H, H-3$_α$), 1.75-1.96 (m, 2H, H-3$_β$), H-4$_α$), 1.36-1.56 (m, 1H, H-4$_β$), 1.22 (t, 3H, J=7.1 Hz, ester CH$_3$).

$^{13}$C-NMR (75 MHz, CDCl$_3$): (mixture of diastereomers) δ (ppm)=174.98 (ester C=O), 140.83, 140.07 (CH$_{olef}$, C-1'), 115.04, 114.39 (CH$_{2,olef}$, C-2'), 62.11, 60.77 (CH, C-5), 60.88, (ester CH$_2$), 59.93, 59.15 (CH, C-2), 31.79 (CH$_2$, C-4), 30.00, 29.37 (CH$_2$, C-3), 14.12 (ester CH$_3$).

IR (ATR): ṽ (cm$^{-1}$)=3344 (br), 3078 (w), 2977 (m), 2866 (w), 1730 (vs), 1639 (w), 1446 (m), 1369 (m), 1276 (m), 1208 (s), 1100 (m), 1035 (m), 993 (m), 918 (m), 861 (m), 759 (w).

MS (GCMS-EI, 70 eV): m/z (%)=169 ([M$^+$], 1), 142 (1), 96 (100), 79 (12), 68 (11), 54 (3).

HRMS (EI, C$_9$H$_{15}$NO$_2$): calc.: 169.1103. found: 169.109.

[α]$_D^{20}$=−39.8° (c=1.065, CHCl$_3$).

(2S,2'S,3'R,5R/S)-1-[1'-((tert-Butoxycarbonyl)-3'-vinylpyrrolidin-2'-yl)carbonyl]-5-vinylpyrrolidine-2-carboxylic acid ethyl ester (180)

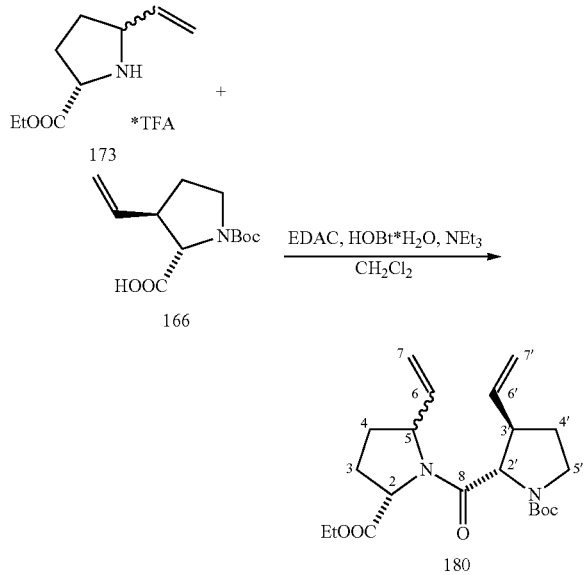

A solution of 34 mg of the carboxylic acid 166 (141 μmol) in 2 ml of anhydrous CH$_2$Cl$_2$ was added with 23 mg of HOBt.H$_2$O (170 μmol, 1.2 eq.) and 33 mg of EDAC (170 μmol, 1.2 eq.) at 0° C., and the mixture was stirred for 15 min to dissolve the HOBt. Thereafter, 50 mg of the ammonium salt 173 (177 μmol, 1.25 eq.) and 25 μl of NEt$_3$ (170 μmol, 1.2 eq.) were added, and the batch was stirred overnight. For work-up, the reaction mixture was diluted with 10 ml of MTBE, washed with a small amount of saturated NH$_4$Cl solution, and the organic phase was dried over MgSO$_4$. After concentrating, the residue was purified using silica gel column chromatography (EE/CH 1:1) to obtain 40 mg (101 μmol, 72%) of dipeptide 180 as a colorless oil.

M (C$_{21}$H$_{32}$N$_2$O$_5$)=392.4893.

R$_f$=0.35 (SiO$_2$, EE/CH 1:1).

$^1$H-NMR (250 MHz, CDCl$_3$): (mixture of diastereomers/rotamers) δ (ppm)=5.82-6.03 (m, 1H, CH$_{olef}$), 5.62-5.82 (m, 1H, CH$_{olef}$), 5.37-5.49 (m, 1H, CH$_{2,olef}$), 4.89-5.20 (m, 3H, CH$_{2,olef}$), 4.42-4.63 (m, 1H), 4.10-4.28 (m, 3H), 3.32-3.73 (m, 2H), 2.76-2.93 (br, 1H), 1.60-2.50 (m, 7H), 1.40, 1.39 (2 s, 9H, OtBu), 1.24 (dt, 3H, J=7.1 Hz, J=3.1 Hz, ester CH$_3$).

(3aS,5S,7aR/S,9aR)-3-(tert-Butoxycarbonyl)-4-oxo-1,3a,4,5,6,7,7a,9a-octahydro-2H-3,4a-diazacyclopenta[f]azulene-5-carboxylic acid ethyl ester (181)

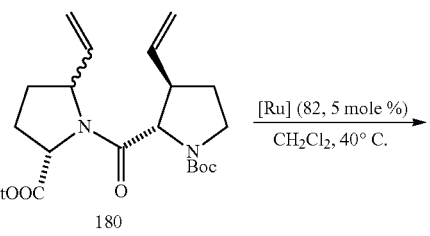

-continued

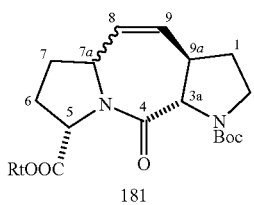

181

18 mg of dipeptide 180 (45.8 μmol) was dissolved in 2 ml of anhydrous CH$_2$Cl$_2$, added with 2.0 mg of [Ru]$_{gr}$ (3.0 μmol, about 6 mole %) and refluxed at 40° C. overnight. After checking completion of the reaction by means of TLC (EE/CH 2:1), the solution was allowed to come to RT, concentrated, and the brown residue was purified using silica gel column chromatography (EE/CH 2:1) to obtain 11 mg of the metathesis product 181 (30.2 μmol, 66%) as a slightly brownish oil.

M (C$_{19}$H$_{28}$N$_2$O$_5$)=364.4361.
Rf=0.17 (SiO$_2$, EE/CH 2:1).
$^1$H-NMR (500 MHz, CDCl$_3$): (mixture of diastereomers/rotamers) δ (ppm)=5.80 (dd, 1H, J=11.2 Hz, J=1.7 Hz, H-8), 5.53 (dd, 1H, J=11.2 Hz, J=1.6 Hz, H-7), 4.77 (dd, 0.6H, J=7.2 Hz, J=3.1 Hz, H-5), 4.67 (br, 1.4H, H-5, H-7a), 4.34 (d, 0.7H, J=10.8 Hz, H-3a), 4.28 (d, 0.3H, J=10.7 Hz, H-3a), 4.10 (m, 2H, ester CH$_2$), 3.73 (dd, 0.4H, J=10.6 Hz, J=8.2 Hz, H-2$_α$), 3.65 (dd, 0.6H, J=10.6 Hz, J=8.1 Hz, H-2$_α$), 3.36 (ddd, 1H, J=15.5 Hz, J=10.6 Hz, J=4.8 Hz, H-2$_β$), 2.28 (br, 1H, H-6/H-7), 2.02 (m, 3H, H-1$_α$, H-6/H-7), 1.86 (m, 1H, H-6/H-7), 1.61 (m, 1H, H-1$_β$), 1.44, 1.38 (2 s, 9H, OtBu), 1.21 (m, 3H, ester CH$_3$).
$^{13}$C-NMR (125 MHz, CDCl$_3$): δ (ppm)=171.98 (C=O), 169.43 (C=O), 146.91 (Boc C=O), 129.43, 129.17 (CH$_{olef.}$, C-9), 129.05, 128.70 (CH$_{olef.}$, C-8), 79.69 (Boc C$_q$), 62.31, 62.09 (CH, C-3a), 61.17, 61.03 (ester CH$_2$), 59.61, 59.53 (CH, C-5), 57.26, 57.17 (CH, C-7a), 46.87, 46.27 (CH$_2$, C-2), 33.09 (CH$_2$, C-6/C-7), 31.29, 30.81 (CH$_2$, C-1), 28.44, 28.15 (CH$_3$, tBu), 27.21, 27.06 (CH$_2$, C-6/C-7), 14.10 (ester CH$_3$).

(2S)-5-Oxopyrrolidine-2-carboxylic acid tert-butyl ester (206)

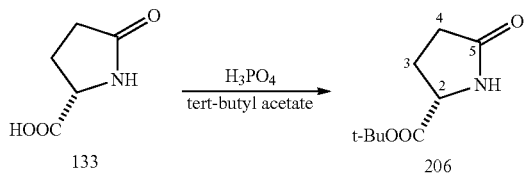

30.0 g of L-pyroglutamic acid 133 (232 mmol) was suspended in 500 ml of tert-butyl acetate and added with 12 ml of 60% perchloric acid. After stirring for 15 h at RT, the resulting clear solution was cooled to 0° C. and adjusted to a pH value of 4-5 by adding 30.0 g of solid NaHCO$_3$. After removing the solid by filtration, the filtrate was concentrated to dryness, thereby obtaining 25.4 g (136 mmol, 58%) of the tert-butyl ester 206 as a white solid that was reacted without further purification. An analytical sample was obtained by column chromatography over silica gel (eluant: EE).

M (C$_9$H$_{15}$NO$_3$)=185.2203.
R$_f$=0.25 (SiO$_2$, EE).
m.p.: 97-98° C. Lit.: 98-99° C.
$^1$H-NMR (300 MHz, CDCl$_3$): δ (ppm)=6.13 (br, 1H, NH), 4.06-4.14 (m, 1H, H-2), 2.22-2.43 (m, 3H, H-3$_α$, H-4) 2.04-2.20 (m, 1H, H-3$_β$), 1.44 (s, 9H, OtBu).

$^{13}$C-NMR (75 MHz, CDCl$_3$): δ (ppm)=177.97 (lactam C=O), 171.07 (ester C=O), 82.18 (Boc C$_q$), 56.07 (CH, C-2), 29.34 (CH$_2$, C-4), 27.87 (CH$_3$ OtBu), 24.75 (CH$_2$, C-3).
IR (ATR): ṽ (cm$^{-1}$)=3239 (br), 2976 (s), 2934 (m), 1731 (vs), 1695 (vs), 1457 (s), 1419 (s), 1392 (s), 1366 (vs), 1227 (vs), 1147 (vs), 1037 (m), 1009 (m), 971 (m), 953 (m), 885 (w), 845 (s), 810 (s).
MS (GCMS-EI, 70 eV): m/z (%)=186 ([MH$^+$], <1), 142 (<1), 84 (100), 57 (38).

(2S)-1-(tert-Butoxycarbonyl)-5-oxopyrrolidine-2-carboxylic acid tert-butyl ester (44)

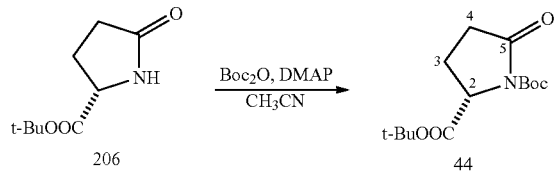

A solution of 20.0 g of lactam 206 (108 mmol) in 200 ml of anhydrous acetonitrile was added with 25.6 ml of Boc$_2$O (120 mmol, 1.1 eq.) and 100 mg of DMAP (0.81 mmol, 0.75 mole %) at 0° C. and subsequently stirred at RT overnight, during which time the solution assumed an intense orange color. For work-up, the solution was concentrated to dryness, and the remaining residue was taken up in 250 ml of a 1:1 mixture of ethyl acetate/cyclohexane and filtered over a short silica gel column. Removal of solvent under vacuum afforded a yellowish oily residue that was made to crystallize from diethyl ether/pentane to obtain 25.9 g of N-Boc-lactam 44 (90.7 mmol, 84%) in the form of small white crystals.

M (C$_{14}$H$_{23}$NO$_5$)=285.3362.
R$_f$=0.20 (SiO$_2$, EE/CH 1:2).
m.p.: 52-53° C. Lit.: 55-56° C.
$^1$H-NMR (300 MHz, CDCl$_3$): δ (ppm)=4.45 (dd, 1H, J=9.3 Hz, J=2.6 Hz, H-2), 2.17-2.66 (m, 3H, H-3$_α$, H-4), 1.9-2.0 (m, 1H, H-3$_β$), 1.48 (s, 9H, OtBu), 1.46 (s, 9H, OtBu).
$^{13}$C-NMR (75 MHz, CDCl$_3$): δ (ppm)=173.27 (lactam C=O), 170.07 (ester C=O), 148.94 (Boc C=O), 82.84 (C$_q$, tBu), 81.86 (C$_q$, tBu), 59.25 (CH, C-2), 30.78 (CH$_2$, C-4), 27.59 (CH$_3$, OtBu), 21.30 (CH$_2$, C-3).
IR (ATR): ṽ (cm$^{-1}$)=2977 (s), 2931 (m), 1790 (vs), 1738 (vs), 1715 (vs), 1476 (m), 1457 (m), 1392 (m), 1367 (vs), 1307 (vs), 1285 (vs), 1254 (vs), 1223 (s), 1148 (vs), 1045 (m), 1021 (m), 962 (w), 912 (w), 842 (s), 774 (m), 643 (w).
MS (GCMS-EI, 70 eV): m/z (%)=270 ([M$^+$-CH$_3$], 6), 239 (4), 227 (9), 207 (4), 185 (3), 171 (6), 153 (2), 143 (15), 129 (5), 101 (4), 97 (7), 87 (72), 74 (100), 57 (12), 55 (14).
[α]$_D^{20}$=−35.3° (c=1.167, CHCl$_3$). Lit.: −35.7° (c=0.9, CHCl$_3$).

(2S,5R/S)-1-(tert-Butoxycarbonyl)-5-hydroxypyrrolidine-2-carboxylic acid tert-butyl ester (207)

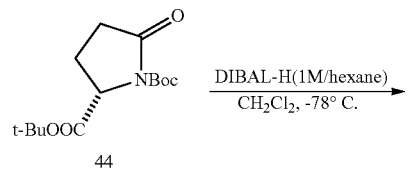

-continued

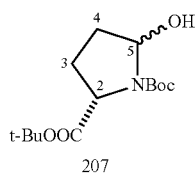

207

A solution of 13.0 g (45.6 mmol) of 44 in 150 ml of anhydrous THF was added dropwise with 100 ml of DIBAL-H (1 M/hexane, 100 mmol, 2.2 eq.) at −78° C. over a period of 30 min, and after completed addition the solution was stirred for two more hours. Thereafter, excess reagent was destroyed by adding 7 ml of isopropanol (evolution of hydrogen). This was added with 200 ml of K—Na tartrate solution (1.77 M), followed by slow thawing to RT overnight. The batch was subsequently transferred into a separating funnel and diluted with 300 ml of MTBE and 100 ml of water. After phase separation, the aqueous phase was extracted with 2×100 ml of MTBE, and the combined organic phases were subsequently dried over MgSO$_4$. Following filtration over a short silica gel column, the solvent was removed under vacuum to obtain 12.2 g of α-hydroxycarbamate 207 (42.3 mmol, 93%) as a colorless oil that was reacted without further purification. An analytical sample was obtained by column chromatography over silica gel (EE/CH 1:2).

M ($C_{14}H_{25}NO_3$)=287.3520.

$R_f$=0.14/0.28 (SiO$_2$, EE/CH 1:2), 2 diastereomers.

$^1$H-NMR (300 MHz, CDCl$_3$): (mixture of diastereomers/rotamers) δ (ppm)=5.37-5.60 (m, 1H, H-5), 4.02-4.25 (m, 1H, H-2), 3.75 (br, 0.4H, OH), 3.52 (br, 0.4H, OH), 3.14 (br, 0.2H, OH), 1.73-2.48 (m, 4H, H-3, H-4), 1.35-1.45 (m, 18M, 2×tBu).

$^{13}$C-NMR (75 MHz, CDCl$_3$): (mixture of diastereomers/rotamers) δ (ppm)=172.06, 171.53 (ester C=O), 154.21, 15383 (Boc C=O), 82.38, 82.09, 81.78 (CH, C-5), 81.15, 80.94, 80.61, 80.55 ($C_q$, 2×tBu), 59.91, 59.82 (CH, C-2), 33.51, 32.17, 31.74, 30.87 (C-4), 28.33, 28.18, 27.87 (CH$_3$, 2×tBu), 27.77, 26.99, 26.81 (CH$_2$, C-3).

IR (ATR): $\tilde{v}$ (cm$^{-1}$)=3460 (br), 2974 (m), 2928 (w), 1740 (s), 1701 (vs), 1477 (m), 1454 (m), 1365 (m), 1325 (m), 1255 (m), 1220 (m), 1149 (vs), 1080 (m), 1061 (m), 1042 (m), 1009 (m), 973 (m), 914 (m), 843 (m), 774 (m), 758 (m).

MS (GCMS-EI, 70 eV): m/z (%)=186 (2), 158 (2), 130 (12), 86 (18), 68 (7), 57 (43), 41 (100).

(2S,5R/S)-1-(tert-Butoxycarbonyl)-5-ethoxypyrrolidine-2-carboxylic acid tert-butyl ester (45)

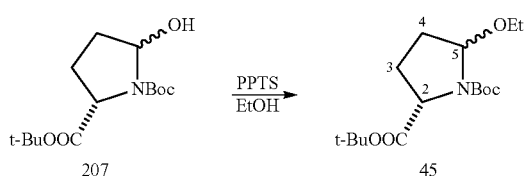

A solution of 12.1 g of 207 (42.1 mmol) in 100 ml of anhydrous EtOH was added with 200 mg of PPTS (0.80 mmol, 1.9 mole %) and stirred at RT overnight. Thereafter, the solvent was completely removed under vacuum, and the residue was taken up in 250 ml of a 1:2 mixture of EE/CH. After filtration over a short silica gel column, the eluate was concentrated to obtain 12.8 g of α-methoxycarbamate 45 (40.5 mmol, 96%) as a slightly yellowish oil. An analytical sample was obtained by column chromatography over silica gel (EE/CH 1:2).

M ($C_{16}H_{29}NO_3$)=315.4052.

$R_f$=0.39/0.52 (SiO$_2$, EE/CH 1:2), two diastereomers.

$^1$H-NMR (300 MHz, CDCl$_3$): (mixture of diastereomers/rotamers) δ (ppm)=5.34 (d, 0.35H, J=4.7 Hz, H-5), 5.30 (d, 0.35H, J=4.7 Hz, H-5), 5.21 (d, 0.1H, J=4.4 Hz, H-5), 5.14 (d, 0.2H, J=4.9 Hz, H-5), 4.02-4.23 (m, 1H, H-2), 3.38-3.80 (m, 2H, ethyl CH$_2$), 1.58-2.48 (m, 4H, H-3, H-4), 1.35-1.45 (m, 18H, 2×OtBu), 1.08-1.16 (m, 3H, ethyl CH$_3$).

$^{13}$C-NMR (75 MHz, CDCl$_3$): (mixture of diastereomers/rotamers) δ (ppm)=171.77, 171.68, 171.49 (ester C=O), 154.44, 154.17, 153.79 (Boc C=O), 87.86, 86.96, 86.84 (CH, C-5), 80.86, 80.57, 80.25, 80.16 ($C_q$, 2×tBu), 64.10, 63.47, 62.83, 62.27 (ethyl CH$_2$), 60.31, 59.95, 59.82 (CH, C-2), 33.07, 32.38, 31.33, 30.39, 27.04, 26.92 (CH$_2$, C-3, C-4), 28.26, 28.18, 28.14, 27.92, 27.84 (CH$_3$, 2×tBu), 15.41, 15.18 (ethyl CH$_3$).

IR (ATR): $\tilde{v}$ (cm$^{-1}$)=2973 (s), 2929 (m), 2873 (w), 1739 (s), 1700 (vs), 1477 (m), 1455 (m), 1363 (vs), 1326 (s), 1255 (s), 1219 (s), 1150 (vs), 1121 (vs), 1078 (vs), 1031 (m), 997 (m), 971 (s), 945 (m), 892 (w), 842 (s), 772 (m).

MS (GCMS-EI, 70 eV): m/z (%)=270 ([M$^+$-OEt], 2), 214 (12), 186 (4), 170 (6), 158 (15), 142 (4), 114 (100), 96 (2), 84 (2), 68 (40), 57 (79).

(2S,5R/S)-5-Allyl-1-(tert-butoxycarbonyl)pyrrolidine-2-carboxylic acid tert-butyl ester (46)

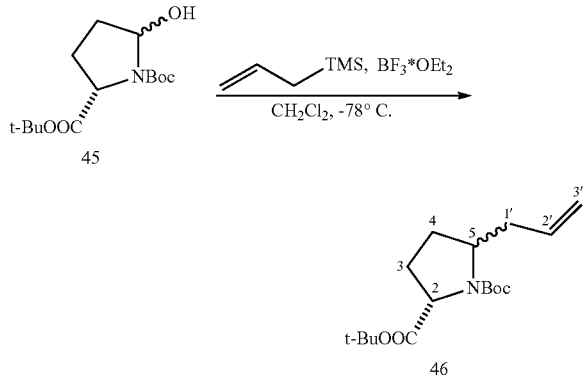

A solution of 12.6 g of the α-methoxycarbamate 45 (40.0 mmol) and 16.0 ml of allyltrimethylsilane (100 mmol, 2.5 eq.) in 100 ml of anhydrous CH$_2$Cl$_2$ was cooled to −78° C. and added dropwise with 10.1 ml of BF$_3$.OEt$_2$ (80.0 mmol, 2 eq.). After completed addition, stirring was continued for 30 min, and completion of the reaction was checked by means of TLC (EE/CH 1:9). Thereafter, 10 ml of a saturated NaHCO$_3$ solution was added, and the batch was allowed to come to RT. After transferring into a separating funnel together with 200 ml of MTBE, the phases were separated and the aqueous phase was extracted with 2×100 ml of MTBE. The combined organic phases were washed with 100 ml of half-conc. NaCl solution, dried over MgSO$_4$ and concentrated. The residue was purified using silica gel column chromatography (EE/CH 1:9), thereby obtaining 9.62 g of allyl substitution product 46 (30.9 mmol, 77%) as a colorless oil (mixture of epimers, cis/trans 75:25).

M ($C_{17}H_{29}NO_4$)=311.4165.

$R_f$=0.30 (SiO$_2$, EE/CH 1:9).

¹H-NMR (300 MHz, CDCl₃): (mixture of diastereomers/rotamers) δ (ppm)=5.72 (m, 1H, H-2$_{olef.}$) 5.01 (m, 2H, H 3'$_{olef.}$) 4.08 (m, 1H, H-2/H-5), 3.82 (br, 1H, H-2/H-5), 2.31-2.76 (m, 1H, H-1'$_\alpha$), 1.55-2.22 (m, 5H, H-1'$_\beta$, H-3, H-4), 1.40 (m, 18H, 2×tBu).

¹³C-NMR (75 MHz, CDCl₃): (mixture of diastereomers/rotamers) δ (ppm)=172.33, 172.13, 172.04 (eater C=O), 154.24, 153.90, 153.75, 153.63 (Boc C=O), 135.48, 135.19, 135.12 (CH$_{olef.}$, C-2'), 117.04, 116.99, 116.63 (CH$_{2,olef.}$, C-3'), 80.72, 80.66 (C$_q$, tBu), 79.62, 79.50 (C$_q$, tBu), 60.74, 60.58 (CH, C-2/C-5), 58.06, 57.42 (CH, C-2/C-5), 39.11, 38.97, 38.14, 38.10 (CH₂, C-1'), 29.34, 28.80, 28.42 (CH₂, C-3/C-4), 28.31, 28.25 (CH₃, tBu), 27.93, 27.86 (CH₃, tBu), 27.42, 26.62 (CH₂, C-3/C-4).

IR (ATR): ṽ (cm⁻¹)=3075 (w), 2973 (s), 2929 (m), 1739 (vs), 1695 (vs), 1639 (m), 1477 (s), 1454 (s), 1387 (vs), 1363 (vs), 1294 (s), 1255 (s), 1216 (s), 1149 (vs), 1103 (vs), 1031 (s), 995 (s), 969 (s), 948 (s), 910 (vs), 856 (s), 842 (s), 771 (s), 633 (m).

MS (GCMS-EI, 70 eV): m/z (%)=270 ([M⁺-C₃H₅], 8), 210 (5), 182 (8), 170 (29), 154 (61), 114 (100), 110 (40), 96 (3), 68 (21), 57 (81).

[α]$_D^{20}$=−34.6° (c=0.985, CHCl₃). Lit.: cis: −24.3° (c=4.36, CHCl₃), trans: −69.3° (c=1.07, CHCl₃).

(2S,5R/S)-1-(tert-Butoxycarbonyl)-5-(2-hydroxyethyl)pyrrolidine-2-carboxylic acid tert-butyl ester (184)

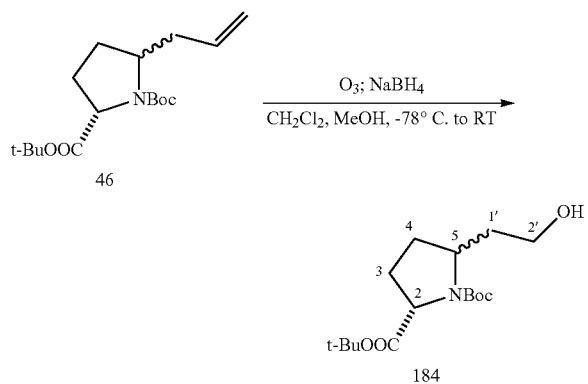

Ozone was passed at −78° C. through a solution of 4.50 g of 46 (14.5 mmol) in a mixture of 38 ml of CH₂Cl₂ and 75 ml of MeOH until a recognizable blue color appeared. The reaction was subsequently terminated and excess ozone removed by purging with oxygen. Thereafter, the colorless reaction solution was added with 1.10 g of NaBH₄ (28.9 mmol, 2 eq.) and stirred overnight to allow thawing to RT. After checking completion of the reaction by means of a thin-layer chromatogram (EE/CH 1:2), the batch was concentrated to dryness, taken up in 200 ml of MTBE and filtered over a small amount of silica gel. The concentrated residue was purified using chromatography on silica gel (EE/CH 1:2), thereby isolating 3.96 g of alcohol 184 (12.6 mmol, 87%) as a colorless oil (mixture of epimers).

M (C₁₆H₂₉NO₅)=315.4052.

R$_f$=0.22 (SiO₂, EE/CH 1:2).

¹H-NMR (300 MHz, CDCl₃): (mixture of diastereomers/rotamers) δ (ppm)=3.92-4.34 (m, 3H, H-2, H-5, OH), 3.45-3.80 (m, 2H, H-2'), 1.49-2.39 (6H, m, H-3, H-4, H-1'), 1.40, 1.41, 1.42, 1.43 (4 s, 18H, 2×tBu).

¹³C-NMR (75 MHz, CDCl₃): (mixture of diastereomers/rotamers) δ (ppm)=172.21 (ester C=O), 155.86, 155.54 (Boc C=O), 81.03, 80.98, 80.67, 80.49 (Boc C$_q$), 60.76, 60.68 (CH, C-2), 59.05, 58.85 (CH₂, C-2'), 54.58, 54.20 (CH, C-5), 39.11, 37.54 (CH₂, C-3/C-4), 30.41, 29.07, 28.94, 28.77 (CH₂, C-3/C-4), 28.23, 27.96 (CH₃, 2×tBu).

IR (ATR): ṽ (cm⁻¹)=3452 (br), 2973 (s), 2934 (m), 2877 (m), 1737 (vs), 1673 (vs), 1477 (s), 1454 (s), 1390 (vs), 1364 (vs), 1340 (s), 1297 (s), 1255 (s), 1215 (s), 1150 (vs), 1116 (vs), 1069 (s), 987 (s), 928 (m), 899 (m), 884 (m), 854 (m), 840 (m), 772 (m), 736 (m).

MS (DIP-EI, 70 eV): m/z (%)=315 ([M⁺], <1), 214 (13), 186 (4), 158 (10), 114 (100), 68 (8), 57 (49).

[α]$_D^{20}$=−43.3° (c=0.915, CHCl₃). Lit.: cis: −48.2° (c=0.51, CHCl₃), trans: −31.2° (c=1.12, CHCl₃).

(2S,5R/S)-1-(tert-Butoxycarbonyl)-5[2-(2-nitrophenylselanyl)ethyl]pyrrolidine-2-carboxylic acid tert-butyl ester (47)

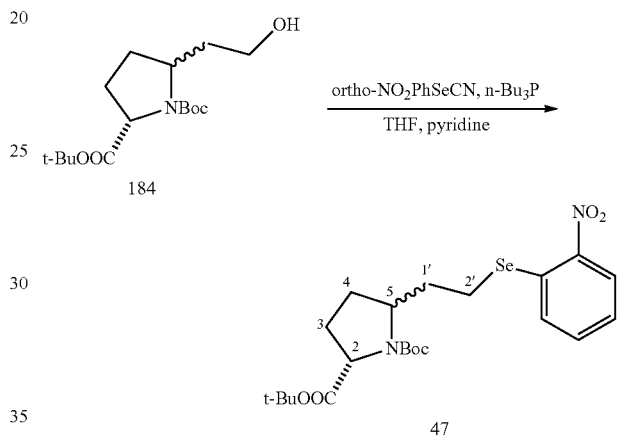

A solution of 4.18 g of alcohol 184 (13.3 mmol) in 50 ml of anhydrous THF and 17 ml of anhydrous pyridine was added with 3.31 g of ortho-nitrophenyl selenocyanate (14.6 mmol, 1.1 eq.). Slow dropwise addition of 4.30 ml of tri-n-butylphosphine (17.3 mmol, 1.3 eq.) with cooling in an ice bath resulted in a dark-red solution. After stirring for 30 min at RT, the batch was diluted with 200 ml of MTBE and filtered over a small amount of silica gel. Concentrating the filtrate afforded a brownish-yellow residue that was purified using silica gel column chromatography (EE/CH 1:4), thereby isolating 6.06 g of the selenyl ether 47 (12.1 mmol, 92%) as an intensely yellow colored oil.

M (C₂₂H₃₂N₂O₆Se)=499.4594.

R$_f$=0.14 (SiO₂, EE/CH 1:4).

¹H-NMR (300 MHz, CDCl₃): (mixture of diastereomers/rotamers) δ (ppm)=8.20-8.28 (m, 1H, PhH), 7.43-7.67 (m, 2H, PhH), 7.20-7.33 (m, 1H, PhH), 3.92-4.33 (m, 2H, H-2, H-5), 2.73-3.12 (m, 2H, H-1'/H-2'), 1.60-2.32 (m, 6H, H-3, H-4, H-1'/H-2'), 1.44, 1.43, 1.42, 1.40 (4 s, 18H, 2×tBu).

¹³C-NMR (75 MHz, CDCl₃): (mixture of diastereomers/rotamers) δ (ppm)=172.28, 171.94 (ester C=O), 154.19, 154.15 (Boc C=O), 146.68 (C$_q$,ar), 133.82 (C$_{q,ar}$), 133.60 (CH$_{ar}$), 129.95, 129.85, 129.21, 128.99, 128.67 (CH$_{ar}$), 126.29, 125.22, 125.06 (CH$_{ar}$), 80.99, 80.91 (C$_q$, tBu), 80.09, 79.94, 79.86 (C$_q$, tBu), 60.60, 60.43 (CH, C-2/C-5), 58.62, 58.29, 57.83 (CH, C-2/C-5), 34.00, 33.55, 33.34 (CH₂), 30.33, 29.93 (CH₂), 28.99, 28.74 (CH₂), 28.40, 28.29 (CH₃, tBu), 27.96 (CH₃, tBu), 27.83, 27.64 (CH₂), 22.95, 22.75, 22.53 (CH₂).

(2S,5R/S)-1-(tert-Butoxycarbonyl)-5-vinylpyrrolidine-2-carboxylic acid tert-butyl ester (185)

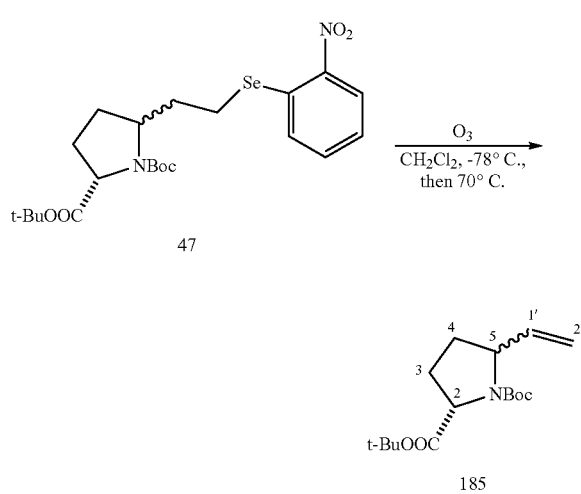

Ozone was passed at −78° C. through a solution 5.80 g of selenyl ether 47 (11.6 mmol) in 150 ml of CH$_2$Cl$_2$ until a recognizable green color appeared. The reaction was subsequently terminated and excess ozone removed by addition of 1-hexene (30 ml in total), during which the color changed from green to yellow. Without thawing to room temperature, the batch was subsequently added dropwise to 200 ml of hexane at 50° C., followed by heating to reflux for 30 min. The orange solution was concentrated and the remaining, intensely orange-colored residue was purified by double column chromatography (CH$_2$Cl$_2$/MeOH 100:1, then EE/CH 1:7) to obtain 3.14 g of the olefin 185 (10.6 mmol, 90%) as a yellowish oil (mixture of epimers).

M (C$_{16}$H$_{27}$NO$_4$)=297.3899.

R$_f$=0.24 (SiO$_2$, EE/CH 1:7).

$^1$H-NMR (300 MHz, CDCl$_3$): (mixture of diastereomers/rotamers) δ (ppm)=5.62-5.94 (m, 1H, H-1'), 4.96-5.42 (m, 2H, H-2'), 4.05-4.55 (m, 2H, H-2, H-5), 1.60-2.22 (m, 4H, H-3, H-4), 1.45, 1.43 (2 s, 9H, tBu), 1.41 (br, 9H, tBu).

$^{13}$C-NMR (75 MHz, CDCl$_3$): (mixture of diastereomers/rotamers) δ (ppm)=172.05, 171.99, 171.92 (ester C=O), 154.24, 154.08, 153.66, 153.54 (Boc C=O), 139.21, 138.60, 138.46, 138.03 (CH$_{olef.}$, C-1'), 114.88, 114.52, 113.77, 113.60 (CH$_{2,olef.}$, C-2'), 80.79, 79.80, 79.67 (Boc C$_q$), 60.95, 60.49, 60.30, 60.14, 59.58, 59.32 (CH, C-2, C-5), 31.51, 30.81, 29.88, 28.95 (CH$_2$C-3/C-4), 28.28 (CH$_3$, tBu), 27.94 (CH$_3$, tBu), 27.29 (CH$_2$, C-3/C-4).

IR (ATR): ṽ (cm$^{-1}$)=3077 (w), 2974 (s), 2928 (m), 2873 (w), 1739 (vs), 1696 (vs), 1643 (w), 1477 (m), 1454 (m), 1387 (vs), 1364 (vs), 1325 (m), 1293 (m), 1255 (s), 1214 (s), 1150 (vs), 1067 (m), 1024 (w), 988 (m), 957 (m), 912 (s), 875 (w), 856 (m), 843 (m), 770 (m), 685 (w).

MS (GCMS-EI, 70 eV): m/z (%)=297 ([M$^+$], <1), 241 (2), 224 (1), 196 (28), 168 (9), 140 (100), 114 (2), 96 (82), 79 (5), 67 (6), 57 (83).

[α]$_D^{20}$=−54.6° (c=0.935, CHCl$_3$). Lit.: cis: −56.0° (c=1.1, CHCl$_3$), trans: −50.6° (c=0.77, CHCl$_3$).

(2S,5R)-5-Vinylpyrrolidine-2-carboxylic acid tert-butyl ester (186a)

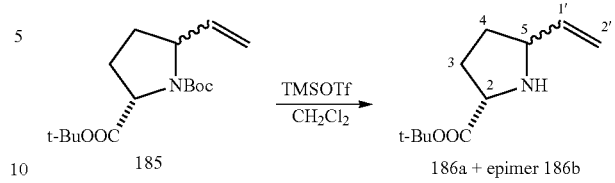

A solution of 800 mg of 185 (2.69 mmol) in 10 ml of anhydrous CH$_2$Cl$_2$ was added dropwise with 0.53 ml of TMSOTf (2.74 mmol, 1.01 eq.) at 0° C. Completion of the reaction was checked after 5 min using TLC (CH$_2$Cl$_2$/MeOH 25:1), and the reaction solution was quenched by adding 2 ml of a saturated NaHCO$_3$ solution. For work-up, the organic phase was diluted with 50 ml of Et$_2$O, separated from the aqueous phase, dried over MgSO$_4$ and concentrated. The residue was purified by careful chromatography on silica gel (CH$_2$Cl$_2$/MeOH of 25:1), where the trans isomer eluted first, closely followed by the desired cis isomer. 104 mg of a mixed fraction (0.53 5 mmol, 20%) and 270 mg of pure cis isomer (1.37 mmol, 51%) were isolated, each in the form of a slightly yellowish oil.

M (C$_{11}$H$_{19}$NO$_2$)=197.2741.

R$_f$=0.16/0.22 (cis/trans isomer, SiO$_2$, CH$_2$Cl$_2$/MeOH 25:1).

$^1$H-NMR (500 MHz, CDCl$_3$): δ (ppm)=5.82 (ddd, 1H, J=17.2 Hz, J=10.2 Hz, J=7.1 Hz, H-1'), 5.13 (d, 1H, J=17.1 Hz, H-2'$_\alpha$), 4.99 (d, 1H, J=10.0 Hz, H-2'$_\beta$), 3.61 (dd, 1H, J=7.4 Hz, J=5.8 Hz, H-2), 3.54 (dd, 1H, J=14.0 Hz, J=7.0 Hz, H-5), 2.10 (s, 1H, NH), 1.98-2.08 (m, 1H, H-3$_\alpha$), 1.81-1.91 (m, 2H, H-3$_\beta$, H-4$_\alpha$) 1.44 (s, 10H, H-4$_\beta$, tBu).

$^{13}$C-NMR (125 MHz, CDCl$_3$): δ (ppm)=174.46 (C=O), 140.23 (CH$_{olef.}$, C-1'), 114.97 (CH$_{2,olef.}$, C-2'), 80.97 (C$_q$, tBu), 62.24 (CH, C-5), 60.76 (CH, C-2), 31.92 (CH$_2$, C-4), 30.39 (C-3), 28.03 (CH$_3$ tBu).

IR (ATR): ṽ (cm$^{-1}$)=3075 (w), 2974 (m), 2870 (w), 1726 (vs), 1640 (w), 1477 (w), 1457 (w), 1425 (w), 1391 (w), 1367 (s), 1282 (w), 1226 (s), 1156 (vs), 1102 (m), 1034 (w), 991 (m), 917 (m), 848 (m), 757 (m).

MS (GCMS-EI, 70 eV): m/z (%)=197 ([M$^+$], <1), 114 (1), 96 (100), 79 (12), 68 (7), 57 (6).

HRMS (ESI, C$_{11}$H$_{19}$NO$_2$) calc.: 198.1494. found: 198.149.

[α]$_\lambda^{20}$=−35.8° (589 nm), −41.6° (546 nm), −81.7° (405 nm), −104.2° (365 nm), −130.4° (334 nm) (c=1.025, CHCl$_3$).

(2S,2'S,3'R,5R)-5-Vinyl-1-[1'-((tert-butoxycarbonyl)-3'-vinylpyrrolidin-2-yl)carbonyl]pyrrolidine-2-carboxylic acid tert-butyl ester (187)

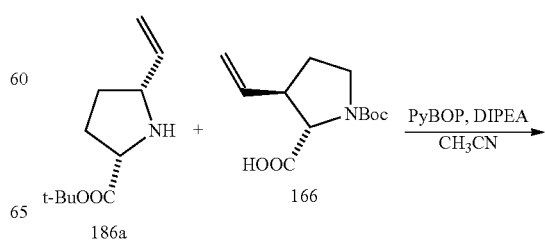

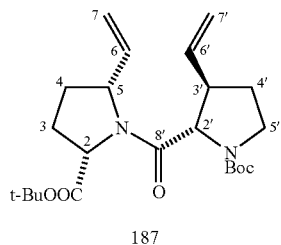

187

A solution of 200 mg of the carboxylic acid 166 (0.83 mmol, 1 eq.) and 200 mg of the amine 186a (1.01 mmol, 1.24 eq.) in 5 ml of anhydrous acetonitrile was added with a solution of 512 mg of PyBOP (0.98 mmol, 1.19 eq.) in 5 ml of anhydrous acetonitrile at 0° C., followed by 180 μl of DIPEA (1.03 mmol, 1.24 eq.). After stirring at room temperature overnight, the solvent was completely removed and the remaining residue was taken up in 20 ml of MTBE and 5 ml of water. After phase separation, the aqueous phase was additionally extracted with MTBE (3×3 ml), and the combined organic phases were dried over MgSO$_4$. Column chromatography over silica gel afforded 282 mg of dipeptide 187 (0.67 mmol, 81%) as a colorless oil.

M ($C_{23}H_{36}N_2O_3$)=420.5424.

$R_f$=0.19 (SiO$_2$, EE/CH 1:3).

$^1$H-NMR (500 MHz, CDCl$_3$): (mixture of rotamers) δ (ppm)=5.91 (m, 1H, H-6), 5.70 (m, 1H, H-6'), 5.40 (dd, 1H, J=17.2 Hz, J=5.4 Hz, H-7$_α$), 5.11 (m, 1H, H-7$_β$), 4.99 (m, 2H, H-7'), 4.87 (t, 0.6H, J=6.3 Hz, H-5), 4.54 (t, 0.4H, J=6.3 Hz, H-5), 4.36 (t, 1H, J=8.0 Hz, H-2), 4.24 (d, 0.6H, J=2.1 Hz, H-2'), 4.15 (s, br, 0.4H, H-2'), 3.66 (m, 0.4H, H-5$_α$'), 3.53 (m, 0.6H, H-5$_α$'), 3.37 (m, 1H, H-5$_β$'), 2.82 (m, 1H, H-3'), 2.37 (m, 1H, H-4$_α$'), 1.72-2.23 (m, 4H, H-3, H-4), 1.66 (m, 1H, H-4$_β$'), 1.44, 1.43 (2 s, 9H, tBu), 1.39, 1.38 (2 s, 9H, tBu).

$^{13}$C-NMR (75 MHz, CDCl$_3$): (mixture of rotamers) δ (ppm)=172.26, 172.15 (C=O), 171.30, 171.05 (C=O), 154.45, 153.63 (Boc C=O), 139.05 (CH$_{olef.}$, C-6), 138.68 (CH$_{olef.}$, C-6'), 116.76/116.37 (CH$_{2,olef.}$, C-7), 114.64, 114.61 (CH$_{2,olef.}$, C-7'), 81.17, 80.85 (C$_q$), 79.58, 79.34 (C$_q$), 61.79, 61.57 (CH, C-2'), 61.04 (CH, C-2), 60.91, 60.80 (CH, C-5), 46.95, 46.18 (CH, C-3), 45.90, 45.56 (CH$_2$, C-5'), 32.81, 32.58 (CH$_2$, C-3/C-4), 29.66 (CH$_2$, C-4), 28.52, 28.47 (CH$_3$ tBu), 28.37 (CH$_2$, C-4), 27.96 (CH$_3$ tBu), 26.99, 26.96 (CH$_2$, C-3/C-4).

IR (ATR): ṽ (cm$^{-1}$)=3079 (w), 2973 (s), 2930 (m), 2876 (m), 1737 (s), 1690 (vs), 1656 (vs), 1477 (m), 1390 (vs), 1364 (vs), 1320 (m), 1301 (m), 1255 (m), 1212 (m), 1155 (vs), 1116 (s), 1067 (m), 1030 (m), 987 (m), 911 (s), 864 (m), 841 (m), 770 (m), 734 (m).

MS (DIP-EI, 70 eV): m/z (%)=420 ([M$^+$], <1), 347 (4), 308 (3), 291 (2), 263 (5), 222 (5), 196 (11), 168 (6), 140 (100), 124 (3), 96 (94), 79 (7), 67 (8), 57 (58).

HRMS (EI, O$_{23}$H$_{36}$N$_2$O$_5$) calc.: 420.2624. found: 420.262.

[α]$_λ^{20}$=−6.7° (589 nm), −8.3° (546 nm), −18.1° (405 nm), −24.7° (365 nm), −34.0° (334 nm) (c=0.710, CHCl$_3$).

(3aS,5S,7aR,9aR)-3-(tert-Butoxycarbonyl)-4-oxo-1,2,3,3a,4,5,6,7,7a,9a-decahydro-3,4a-diazacyclopenta[f]azulene-5-carboxylic acid tert-butyl ester (188)

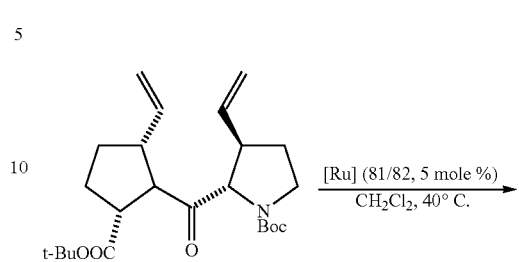

A solution of 250 mg of dipeptide 187 (0.59 mmol) and 25 mg of [Ru] (81) (29.45 μmol, 5 mol %) in 8 ml of anhydrous CH$_2$Cl$_2$ was heated at reflux under argon protection atmosphere overnight until the reaction was complete according to TLC (EE/CH 1:1). After cooling to RT, the reaction was initially added with 1 ml of ethyl vinyl ether and stirred for 30 min. Thereafter, 365 mg of tris(hydroxymethyl)phosphine (2.94 mmol, 100 eq., based on catalyst) and 200 ml of DIPEA were added, resulting in a visible color change of the solution from brown to bright-yellow. For work-up, 50 ml of MTBE and 5 ml of water were added, the phases were separated, and the organic phase was dried over MgSO$_4$. Purification using silica gel column chromatography (EE/CH 1:1) afforded 210 mg of tricyclic 188 (0.54 mmol, 92%) as a colorless oil which gradually solidified to form small colorless crystals.

M ($C_{21}H_{32}N_2O_5$)=392.4893.

$R_f$=0.20 (SiO$_2$, EE/CH 1:1).

m.p.: 147-149° C.

$^1$H-NMR (500 MHz, CDCl$_3$): (mixture of rotamers) δ (ppm)=5.84 (d, 1H, J=11.2 Hz, H-8), 5.58 (d, 1H, J=11.1 Hz, H-9), 4.68 (m, 2H, H-5, H-7a), 4.37 (d, 0.6H, J=10.8 Hz, H-3a), 4.32 (d, 0.4H, J=10.7 Hz, H-3a), 3.69 (m, 1H, H-2$_α$), 3.43 (m, 1H, H-2$_β$), 2.98 (m, 1H, H-9a), 2.32 (m, 1H, H-6/H-7), 2.07 (m, 3H, H1, H-6/H-7)), 1.88 (m, 1H, H-6/H-7), 1.66 (m, 1H, H-1$_β$), 1.48, 1.47 (2 s, 9H, OtBu), 1.44, 1.42 (2 s, 9H, OtBu).

$^{13}$C-NMR (125 MHz, CDCl$_3$): (mixture of rotamers) δ (ppm)=171.11, 170.94 (C=O), 169.49, 169.30 (C=O), 154.68, 154.18 (Boc C=O), 129.53, 129.32 (CH$_{olef.}$, C-9), 128.95, 128.60 (CH$_{olef.}$, C-8), 81.34, 81.13 (C$_q$, OtBu), 79.67, 79.60 (C$_q$, OtBu), 62.27, 62.05 (CH, C-3a), 60.22, 60.15 (CH, C-5/C-7a), 57.22, 57.11 (CH, C-5/C-7a), 46.90, 46.28 (CH$_2$, C-2), 41.96, 41.35 (CH, C-9a), 33.01 (CH$_2$, C-6/C-7), 31.32, 30.85 (CH$_2$, C-1), 28.43, 28.14, 27.90 (CH$_3$, OtBu), 27.41, 27.24 (CH$_2$, C-6/C-7).

IR (ATR): ṽ (cm$^{-1}$)=2972 (m), 2928 (m), 2866 (w), 2245 (w), 1738 (s), 1700 (vs), 1677 (vs), 1476 (m), 1408 (vs), 1389 (vs), 1364 (vs), 1340 (s), 1327 (s), 1255 (s), 1218 (s), 1159 (vs), 1121 (s), 1072 (m), 920 (m), 833 (m), 771 (m), 730 (s), 654 (w).

MS (DIP-EI, 70 eV): m/z (%)=392 ([M$^+$], 3), 336 (4), 319 (9), 291 (13), 263 (10), 235 (84), 207 (25), 193 (8), 163 (28), 146 (15), 134 (7), 120 (12), 94 (9), 82 (12), 69 (9), 57 (100).

HR-MS (EI, $C_{21}H_{32}N_2O_5$) calc.: 392.2311. found: 392.231.

$[\alpha]_\lambda^{20}$=−212.6° (589 nm), −252.1° (546 nm), −514.6° (405 nm), −672.6° (365 nm), −860.7° (334 nm) (c=301.015, $CHCl_3$).

(3aS,5S,7aR,9aR)-3-(Fluorenyl-9-methoxycarbonyl)-4-oxo-1,3a,4,5,6,7,7a,9a-octahydro-2H-3,4a-diazacyclopenta[f]azulene-5-carboxylic acid (85)

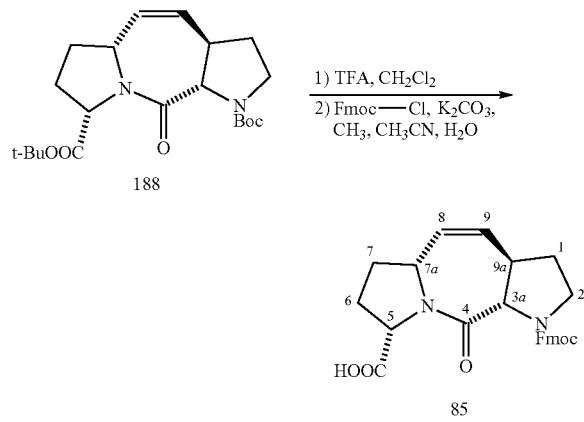

150 mg of metathesis product 188 (0.38 mmol) was dissolved in 2 ml of $CH_2Cl_2$, cooled to 0° C. and added dropwise with 2 ml of TFA (99%). Thereafter, the batch was allowed to come to RT and stirred for one hour. Any volatile components were subsequently removed under vacuum to obtain a yellowish residue which gradually solidified under oil pump vacuum.

The crude product was taken up in a mixture of 4 ml of acetonitrile and 3 ml of 10% $K_2CO_3$ solution, cooled to 0° C. in an ice bath and added with a solution of 200 mg of Fmoc-Cl (0.77 mmol, 2 eq.) in 2 ml of acetonitrile. After stirring overnight, the batch was cooled to 0° C. again, diluted with 50 ml of $CH_2Cl_2$ and cautiously adjusted to pH 4 using 1 M HCl. After phase separation, the aqueous phase was extracted with 3×10 ml of $CH_2Cl_2$, and the combined organic phases were dried over $MgSO_4$ and concentrated. The residue was purified by chromatography using a fairly short silica gel column ($CH_2Cl_2$/MeOH 9:1, optionally using a gradient to 8:2) to obtain 150 mg of the Fmoc-protected diproline 85 (0.33 mmol, 86%) in the form of a yellowish solid.

M ($C_{27}H_{26}N_2O_3$)=458.5058.

$R_f$=0.16 ($SiO_2$, $CH_2Cl_2$/MeOH 9:1).

m.p.: 163° C. (decomposition).

$^1$H-NMR (300 5 Hz, $CDCl_3$): (mixture of rotamers) δ (ppm)=7.76-7.82 (m, 2H, $H_{ar}$), 7.48-7.65 (m, 2H, $H_{ar}$), 7.25-7.43 (m, 4H, $H_{ar}$), 5.75 (d, 0.4H, J=11.1 Hz, H-8), 5.66 (d, 0.6H, J=11.0 Hz, H-8), 5.55 (d, 0.4H, J=11.0 Hz, H-9), 5.47 (d, 0.6H, J=11.1 Hz, H-9), 4.73 (dd, 0.6H, J=10.8 Hz, J=5.3 Hz, $CH_{2,Fmoc}$), 4.65 (br, 0.4H, H-7a), 4.16-4.58 (m, 3.6H, $CH_{2,Fmoc}$, H-5, H-3a, H-7a, $CH_{Fmoc}$), 4.12 (t, 0.7H, J=4.4 Hz, $CH_{Fmoc}$), 3.80 (d, 0.7H, J=10.4 Hz, H-3a), 3.61 (dd, 0.6H, J=8.1 Hz, J=10.1 Hz, H-2$_\alpha$), 3.54 (m, 0.4H, H-2$_\alpha$), 3.13-3.30 (m, 1H, H-2$_\beta$), 2.75-2.95 (br, 1H, H-9a), 2.21-2.32 (m, 1H, H-7$_\alpha$), 1.90-2.14 (m, 3H, H-6, H-1$_\alpha$), 1.70-1.90 (br, 1H, H-7$_\beta$), 1.45-1.56 (m, 0.4H, H-1$_\beta$), 1.25-1.40 (m, 0.6H, H-1$_\beta$).

$^{13}$C-NMR (125 MHz, $CDCl_3$): (mixture of rotamers) δ (ppm)=178.12, 178.01 (carboxyl C=O), 172.69, 172.37 (C=O), 156.97, 156.80 (Fmoc C=O), 145.94, 145.51, 145.10, 144.93, 142.78, 142.71, 142.59 ($C_{q,ar}$), 130.56, 130.32 ($CH_{olef.}$), 129.43, 129.37 ($CH_{olef.}$), 128.85, 128.81, 128.71 ($CH_{ar}$), 128.24, 128.17, 128.10 ($CH_{ar}$), 126.19, 126.11, 125.96, 125.81 ($CH_{ar}$), 120.99, 120.90, 120.80 ($CH_{ar}$), 68.57, 67.29 ($CH_{2,Fmoc}$), 63.60, 63.34 (CH, C-3a), 59.16, 59.05 (CH, C-7a), 49.33, (CH, $CH_{Fmoc}$), 48.50 (CH, C-5), 48.22, 48.13 ($CH_2$, C-2), 43.09, 42.46 (CH, C-9a), 34.13, 33.97 ($CH_2$, C-7), 32.17, 31.62 ($CH_2$, C-1), 28.31 ($CH_2$, C-6).

IR (ATR): $\tilde{\nu}$ ($cm^{-1}$)=3419 (br), 2956 (m), 2880 (m), 2364 (w), 2238 (w), 1681 (vs, br), 1449 (vs), 1416 (vs), 1350 (s), 1327 (s), 1300 (m), 1240 (m), 1220 (m), 1169 (s), 1120 (s), 1021 (m), 985 (m), 908 (s), 839 (m), 759 (vs), 736 (vs).

MS (DIP-EI, 70 eV): m/z (%)=236 ([M$^+$-Fmoc], <1), 178 (fluorene, 100), 152 (42), 126 (6), 98 (5), 89 (55), 76 (67), 63 (18), 51 (6).

HR-MS (ESI, $C_{27}H_{26}N_2O_5$) calc.: 481.1740. found: 481.173.

$[\alpha]_\lambda^{20}$=−135.5° (589 nm), −160.4° (546 nm), −318.3° (405 nm), −406.0° (365 nm), absorbs at 334 nm (c=0.86, MeOH).

The compounds specified above exhibit a surprisingly good affinity to proteins having the Src homology 3 domains, WW domains, Ena/VASP homology 1 domains, GYF domains, UEV domains and/or profilin. This surprisingly good affinity can be utilized in the diagnosis or treatment of viral or bacterial diseases involving proteins having the above-mentioned domains. Apart from the quoted infectious diseases, such proteins are also involved in neurodegenerative diseases and tumor diseases. Experiments in test organisms show good tolerability of the compounds according to the invention, even when used in combination with other molecules.

| Abbreviations | |
|---|---|
| eq. | equivalent(s) |
| Ar | aryl |
| ATR | Attenuated Total Internal Reflectance |
| 9-BBN | 9-borabicyclononane |
| calc. | calculated |
| Bn | Benzyl |
| Boc | tert-butoxycarbonyl |
| $Boc_2O$ | di-tert-butyl dicarbonate (Boc anhydride) |
| CH | cyclohexane |
| Cy | cyclohexyl |
| TLC | thin-layer chromatogram |
| DCE | dichloroethane (1,2-) |
| DCM | dichloromethane |
| DIBAL-H | diisobutylaluminum hydride |
| DIC | diisopropylcarbodiimide |
| DIP | Direct Inlet Probe (mass spectrometry) |
| DIPEA | diisopropylethylamine |
| DMAP | 4-N,N-dimethylaminopyridine |
| DMF | N,N-dimethylformamide |
| DMP | 2,2-dimethoxypropane |
| DMS | 2,2-dimethylsulfide |
| DMSO | dimethyl sulfoxide |
| dr | diastereomeric ratio |
| EE | ethyl acetate |
| ee | enantiomeric excess |
| EI | Electron Impact Ionization |
| ESI | Electron Spray Ionization |
| Et | ethyl |
| $Et_2O$ | diethyl ether |
| EtOH | ethanol |
| EVH1 | Ena/VASP homology 1 domain |
| FGI | functional group inversion |
| Fmoc | fluoroenyl-9-methoxycarbonyl |
| FMP | Forschungsinstitut für Molekulare Pharmakologie (Berlin-Buch) |
| GC-MS | gas chromatography connected to mass spectrometry |

Abbreviations

| | |
|---|---|
| HPLC | High Performance Liquid Chromatography |
| HRMS | High-Resolution Mass Spectrometry |
| IR | Infrared spectroscopy |
| conc. | concentrated |
| LiHMDS | lithium hexamethyldisilazide |
| M | molar mass |
| MCPBA | meta-chloroperbenzoic acid |
| Me | methyl |
| MeOH | methanol |
| Ms | mesyl (methanesulfonyl) |
| M | mass spectrometry |
| MTBE | methyl tert-butyl ether |
| NaHMDS | sodium hexamethyldisilazide |
| NME | N-methylephedrine |
| NMR | nuclear magnetic resonance spectroscopy |
| NOE | Nuclear Overhauser Effect |
| o | ortho |
| Ph | phenyl |
| PPII | polyproline helix type II |
| POM-Cl | chloromethyl pivaloate |
| PPTS | pyridinium para-toluenesulfonate |
| RCM | ring closure metathesis |
| Rf | retention factor |
| $[Ru]_{II}$ | Grubbs II catalyst 81 |
| $[RU]_{gr}$ | modified (green) Grubbs-Hoveyda catalyst according to Ble-chert, 82 |
| s | secondary |
| m.p. | melting point |
| Su | succinimide |
| TBAF | tetrabutylammonium fluoride |
| TBS | tert-butyldimethylsilyl |
| t-Bu | tert-butyl |
| Tf | trifluoromethanesulfonyl |
| TFA | trifluoroacetic acid |
| THF | tetrahydrofuran |
| TMEDA | tetramethylethylenediamine |
| TMS | trimethylsilyl |
| TMSOTf | trimethylsilyl trifluoromethanesulfonate |
| TPS | tert-butyldiphenylsilyl |
| Ts | tosyl (para-toluenesulfonyl) |
| TsOH | para-toluenesulfonic acid |
| Z | benzyloxycarbonyl (also: Cbz) |

Single-Letter Code and Three-Letter Code of Natural Proteinogenic Amino Acids:

| | | |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

The invention claimed is:

1. Compounds according to general formula 1

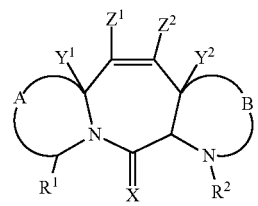

with a unsaturated central seven-membered ring, wherein X is O and/or S;

A, B are ring bridges and wherein variable A and B independently re resent —$CH_2$—, —O—, —S and/or NH and NR with R=H, alkyl or acyl;

$Y^1$, $Y^2$ are H, alkyl, fluoroalkyl, aryl and/or heteroaryl;

$Z^1$, $Z^2$ are H, carbonyl, OH, O-alkyl, O-acyl, $NR^1R^2$ with $R^1$ and/or $R^2$=H, alkyl, acyl, sulfonyl, alkyl, acyl, fluoroalkyl, aryl and/or heteroaryl;

$R^1$ is alkyl, acyl, alkoxycarbonyl, aryloxycarbonyl and/or aminocarbonyl ($CONH_2$, CONHR, CONH peptidyl, (with R));

$R^2$ is H, alkyl, aryl, alkylcarbonyl, arylcarbonyl, alkoxycarbonyl, aminocarbonyl, aryloxycarbonyl, alkylsulfonyl, arylsulfonyl, aminoacyl and/or peptidyl.

2. The compounds according to claim 1, wherein

A and/or B are 5 and/or 6 ring atoms and ring members represented by A and B are selected from the group comprising C, O, S and/or N atoms.

3. The compounds according to claim 1 in accordance with general formula 2

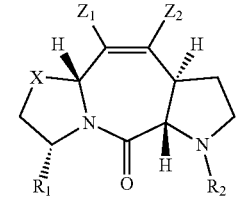

with $Z^1$, $Z^2$ as represented in said general formula 1 and with a configuration shown in formula 2;

with $R^1$, $R^2$=alkyl, acyl, hetaryl and/or sulfonyl, with X=—$CH_2$—, —O—, —S— and/or —NH— and —N(R)—, with R=H, alkyl or acyl.

4. The compounds according to claim 3, wherein the compound corresponds to structures shown in formula 3:

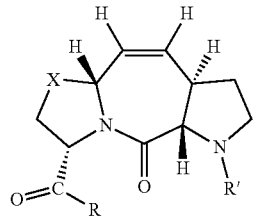

with X=$CH_2$—, —O— and/or —S—;
with R=NHR", —OR", with R"=peptidyl, substituted alkyls, hetaryl;
with R'=acyl, peptidyl and/or sulfonyl.

5. The compounds according to claim 1, wherein said compounds are pharmaceutical active substances.

6. A pharmaceutical agent comprising a compound according to claim 1, optionally together with a pharmaceutically tolerable carrier.

7. The pharmaceutical agent according to claim 6, wherein the pharmaceutical carriers are selected from the group comprising fillers, diluents, binders, humectants, dissolution retarders, disintegrants, absorption enhancers, wetting agents, absorbents and/or lubricants.

8. A method for providing ligands comprising providing compounds of claim 1, wherein said compounds are employed as ligand for a domain selected from the group comprising Src homology 3 domains, WW domains, Ena/VASP homology 1 domains, GYF domains, UEV domains and/or profilin.

9. The method of claim 8, wherein the compounds are employed as polyproline mimetics.

10. A method of producing a drug comprising providing the pharmaceutical agents of claim 6, wherein the drug is used for treatment of diseases associated with a modification of intracellular signal transduction processes mediated by polyproline helical structures, said diseases being selected from the group comprising bacterial and/or viral infectious diseases, neurodegenerative diseases and/or tumor diseases.

11. A method for treating bacterial and/or viral infectious diseases, neurodegenerative diseases and/or tumor diseases comprising administering to a patient in need thereof the compound of claim 1 in a treating bacterial and/or viral infectious diseases, neurodegenerative diseases and/or tumor diseases effective amount, wherein the compound is optionally administered orally, subcutaneously, intravenously, intramuscularly, intraperitoneally and/or topically.

12. The method of claim 11, wherein the bacterial diseases are induced by bacteria selected from the group comprising legionellas, streptococci, staphylococci, klebsiellas, *Haemophilis influenzae*, rickettsiae (typhoid fever), mycobacteria, mycoplasmas, ureaplasmas, neisseriae (meningitis, Waterhouse-Friedrichsen syndrome, gonorrhea), pseudomonads, bordetellas (pertussis), corynebacteria (diph-theria), chlamydiae, campylobacteria (diarrhea), *Escherichia coli*, proteus, salmonellas, shigellas, yersiniae, vibrions, enterococci, clostridiae, borre-liae, *Treponema pallidum*, brucellas, francisellas and/or *Leptospira*, particularly listeriae.

13. The method of claim 12, wherein the listeriae are selected from the group comprising *L. monocytogenes* Sv1/2a, *L. monocytogenes* Sv4b F2365, *L. monocytogenes* Sv4b H7858, 178 contigs, *L. monocytogenes* Sv1/2a F6854, 133 contigs, *L. monocytogenes* Sv4b, *L. monocytogenes* Sv4a, *L. innocua* Sv6a, *L. welshimeri* Sv6b, *L. seeligeri* Sv1/2b and/or *L. ivanovii* Sv5.

14. The method of claim 11, wherein the neurodegenerative disease is selected from the group comprising Alzheimer's disease, Parkinson's disease, Huntington's disease and/or amyotrophic lateral sclerosis (ALS).

15. The method of claim 11, wherein the viral infectious disease is a hepatitis and/or an HIV disease.

16. The method of claim 11, wherein the tumor disease is a carcinoma, a sarcoma, a neuroendocrine tumor, a hemooncologic tumor, a dysontogenetic tumor and/or a mixed tumor.

17. The method of claim 11, wherein the tumor disease is selected from the group comprising tumors of the ear-nose-throat region, comprising tumors of the inner nose, nasal sinus, nasopharynx, lips, oral cavity, oropharynx, larynx, hypopharynx, ear, salivary glands, and paragangliomas, tumors of the lungs comprising non-parvicellular bronchial carcinomas, parvicellular bronchial carcinomas, tumors of the mediastinum, tumors of the gastrointestinal tract, comprising tumors of the esophagus, stomach, pancreas, liver, gallbladder and biliary tract, small intestine, colon and rectal carcinomas and anal carcinomas, urogenital tumors comprising tumors of the kidneys, ureter, bladder, prostate gland, urethra, penis and testicles, gynecological tumors comprising tumors of the cervix, vagina, vulva, uterine cancer, malignant trophoblast disease, ovarial carcinoma, tumors of the uterine tube (Tuba Faloppii), tumors of the abdominal cavity, mammary carcinomas, tumors of the endocrine organs, comprising tumors of the thyroid, parathyroid, adrenal cortex, endocrine pancreas tumors, carcinoid tumors and carcinoid syndrome, multiple endocrine neoplasias, bone and soft-tissue sarcomas, mesotheliomas, skin tumors, melanomas comprising cutaneous and intraocular melanomas, tumors of the central nervous system, tumors during infancy, comprising retinoblastoma, Wilms tumor, neurofibromatosis, neuroblastoma, Ewing sarcoma tumor family, rhabdomyosarcoma, lymphomas comprising non-Hodgkin lymphomas, cutaneous T cell lymphomas, primary lymphomas of the central nervous system, Hodgkin's disease, leukemias comprising acute leukemias, chronic myeloid and lymphatic leukemias, plasma cell neoplasms, myelodysplasia syndromes, paraneoplastic syndromes, metastases with unknown primary tumor (CUP syndrome), peritoneal carcinomatosis, immunosuppression-related malignancy comprising AIDS-related malignancy such as Kaposi sarcoma, AIDS-associated lymphomas, AIDS-associated lymphomas of the central nervous system, AIDS-associated Hodgkin's disease and AIDS-associated anogenital tumors, transplantation-related malignancy, metastasized tumors comprising brain metastases, lung metastases, liver metastases, bone metastases, pleural and pericardial metastases, and malignant ascites.

18. The method of claim 10 in the production of a drug for the modulation of oncogenic protein activity or modulation of signal transduction pathways.

19. The method of claim 10, wherein the pharmaceutical agent is prepared and used in form of a gel, poudrage, powder, tablet, sustained-release tablet, premix, emulsion, brew-up formulation, drops, concentrate, granulate, syrup, pellet, bolus, capsule, aerosol, spray and/or inhalant.

20. The method of claim 10,
wherein the pharmaceutical agent is present in a preparation at a concentration of from 0.1 to 99.5, preferably from 0.5 to 95.0, and more preferably from 20.0 to 80.0 wt. %.

21. The method of claim 11,
wherein
said compound is employed in total amounts of from 0.05 to 500 mg per kg, preferably from 5 to 100 mg per kg body weight per 24 hours.

22. The method of claim 21,
wherein said compound is administered orally, via injection, topically, vaginally, rectally and/or nasally.

23. A method of identifying an inhibitor of binding between a first molecule which comprises a domain selected from the group comprising Src homology 3 domains, WW domains, Ena/VASP homology 1 domains, GYF domains, UEV domains and/or profilin and a second molecule which binds to said domain, the second molecule being an agent comprising at least one compound according to claim 1, said method comprising incubation of one or more agents, among which selection of such an inhibitor is desired, with the first molecule and the second molecule under conditions suitable for binding and detection of one or more compounds which inhibit binding of the first molecule to the second molecule.

24. A method of identifying a compound which influences binding of a molecule comprising a domain selected from the group comprising Src homology 3 domains, WW domains, Ena/VASP homology 1 domains, GYF domains, UEV domains and/or profilin with a compound according to claim 1, said method comprising:

(a) contacting the Src homology 3 domains, WW domains, Ena/VASP homology 1 domains, GYF domains, UEV domains and/or profilin with said compound under conditions suitable for binding in presence of a candidate compound and measuring an extent of binding between the domain and the compound; and (b) comparing the extent of binding measured in (a) with an extent of binding which is known or has been determined to exist between the domain and the compound in the absence of a candidate compound, a difference between the extent of binding measured in (a) and the extent of binding which is known or has been determined to exist between the domain and the ligand in the absence of a candidate compound indicating that the candidate compound is a compound that influences binding between the domain and the compound according to claim 1.

25. A kit comprising in one container, at least one compound according to claim 1 and/or a pharmaceutical agent comprising said compound together with a pharmaceutically tolerable carrier, optionally, in a second container, information for combining the contents of the kit.

26. The kit of claim 25, further comprising instructions for using the compound and/or pharmaceutical agent in the prophylaxis or therapy of neurodegenerative diseases, bacterial infectious diseases or tumor diseases.

\* \* \* \* \*

UNITED STATES PATENT AND TRADEMARK OFFICE
CERTIFICATE OF CORRECTION

PATENT NO. : 8,242,105 B2
APPLICATION NO. : 12/442681
DATED : August 14, 2012
INVENTOR(S) : Kuehne et al.

It is certified that error appears in the above-identified patent and that said Letters Patent is hereby corrected as shown below:

Column 68, please correct issued claim 1 as follows:

-- 1. Compounds according to general formula 1

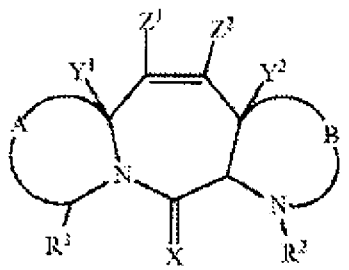

with a unsaturated central seven-membered ring, wherein X is O and/or S;

A, B are ring bridges and wherein variable A and B independently ~~re resent~~ represent $-CH_2-$, $-O-$, $-S-$, and/or NH and N(R) with R =H, alkyl or acyl;
$Y^1$, $Y^2$ are H, alkyl, fluoroalkyl, aryl and/or heteroaryl;
$Z^1$, $Z^2$ are H, carbonyl, OH, O-alkyl, O-acyl, $NR^1R^2$ with $R^1$ and/or $R^2$ = H, alkyl, acyl, sulfonyl, alkyl, acyl, fluoroalkyl, aryl and/or heteroaryl;
$R^1$ is alkyl, acyl, alkoxycarbonyl, aryloxycarbonyl and/or aminocarbonyl ($CONH_2$, CONHR, CONH peptidyl, (with R));
$R^2$ is H, alkyl, aryl, alkylcarbonyl, arylcarbonyl, alkoxycarbonyl, aminocarbonyl, aryloxycarbonyl, alkylsulfonyl, arylsulfonyl, aminoacyl and/or peptidyl. --

Signed and Sealed this
Thirtieth Day of April, 2013

Teresa Stanek Rea
*Acting Director of the United States Patent and Trademark Office*